US 7,582,122 B2

(12) United States Patent
Daubresse et al.

(10) Patent No.: US 7,582,122 B2
(45) Date of Patent: Sep. 1, 2009

(54) MIXED CATIONIC DYES COMPRISING AT LEAST ONE ANTHRAQUINONE CHROMOPHORE AND THEIR USE IN METHODS OF HAIR DYEING

(75) Inventors: Nicolas Daubresse, La Celle St. Cloud (FR); Andrew Greaves, Montevrain (FR)

(73) Assignee: L'Oreal S.A., Paris (FR)

( * ) Notice: Subject to any disclaimer, the term of this patent is extended or adjusted under 35 U.S.C. 154(b) by 252 days.

(21) Appl. No.: 11/510,698

(22) Filed: Aug. 28, 2006

(65) Prior Publication Data

US 2007/0125261 A1 Jun. 7, 2007

(30) Foreign Application Priority Data

Aug. 26, 2005 (FR) .................................. 05 08793

(51) Int. Cl.
*A61Q 5/10* (2006.01)
*C09B 1/16* (2006.01)

(52) U.S. Cl. .................. 8/405; 8/406; 8/426; 8/437; 8/451; 8/565; 8/566; 8/567; 8/570; 8/571; 8/638; 8/639; 8/643; 8/662; 8/670; 552/255

(58) Field of Classification Search .................. 8/405, 8/406, 426, 437, 451, 565, 566, 567, 570, 8/571, 639, 643, 675, 638, 662, 670; 552/255
See application file for complete search history.

(56) References Cited

U.S. PATENT DOCUMENTS

| 3,100,739 A | 8/1963 | Kaiser et al. |
| 3,271,383 A | 9/1966 | Yamaya et al. |
| 3,423,427 A | 1/1969 | Anthony et al. |
| 3,467,483 A | 9/1969 | Bugaut et al. |
| 3,524,842 A | 8/1970 | Grossmann et al. |
| 3,578,386 A | 5/1971 | Kaliopissis et al. |
| 3,578,387 A | 5/1971 | Zviak et al. |
| 3,617,163 A | 11/1971 | Kalopissis et al. |
| 3,652,556 A | 3/1972 | Kühlthau et al. |
| 3,817,698 A | 6/1974 | Kalopissis et al. |
| 3,867,456 A | 2/1975 | Kalopissis et al. |
| 3,955,918 A | 5/1976 | Lang |
| 3,985,499 A | 10/1976 | Lang et al. |
| 3,995,088 A | 11/1976 | Garner et al. |
| 4,025,301 A | 5/1977 | Lang |
| 4,054,718 A | 10/1977 | Garner et al. |
| 4,151,162 A | 4/1979 | Lang et al. |
| 4,153,065 A | 5/1979 | Lang |
| 4,226,784 A | 10/1980 | Kalopissis et al. |
| 4,394,310 A | 7/1983 | Fuchs et al. |
| 4,537,844 A | 8/1985 | Hashimoto |
| 4,661,115 A | 4/1987 | Orth et al. |
| 4,670,385 A | 6/1987 | Babb et al. |
| 4,823,985 A | 4/1989 | Grollier et al. |
| 4,886,517 A | 12/1989 | Bugaut et al. |
| 5,094,688 A | 3/1992 | Eckstein et al. |
| 5,097,034 A | 3/1992 | Eckstein |
| 5,122,605 A | 6/1992 | Pedrazzi |
| 5,132,438 A | 7/1992 | Bach et al. |
| 5,139,997 A | 8/1992 | Bach et al. |
| 5,674,299 A | 10/1997 | Kaiser |
| 5,708,151 A | 1/1998 | Mückli |
| 5,821,347 A | 10/1998 | Dannheim |
| 5,831,039 A | 11/1998 | Schumacher |
| 5,879,413 A | 3/1999 | Pengilly et al. |
| 5,888,252 A | 3/1999 | Mockli |
| 5,919,273 A | 7/1999 | Rondeau et al. |
| 5,980,587 A | 11/1999 | Samain |
| 5,993,490 A | 11/1999 | Rondeau et al. |
| 6,045,591 A | 4/2000 | Deneulenacre |
| 6,136,042 A | 10/2000 | Maubru |
| 6,140,478 A | 10/2000 | Geiwiz et al. |
| 6,179,881 B1 | 1/2001 | Henrion et al. |
| 6,297,362 B1 | 10/2001 | Kunde et al. |
| 6,368,360 B2 | 4/2002 | Samain |
| 6,416,770 B1 | 7/2002 | Leduc et al. |
| 6,437,149 B1 * | 8/2002 | Genet et al. ............... 548/335.1 |
| 6,458,167 B1 | 10/2002 | Genet et al. |
| 6,468,316 B1 | 10/2002 | Genet et al. |
| 6,492,502 B2 | 12/2002 | Henrion et al. |
| 6,530,959 B1 | 3/2003 | Lang et al. |
| 6,547,834 B1 | 4/2003 | Matsunaga et al. |
| 6,592,634 B1 | 7/2003 | Reichert et al. |
| 6,712,861 B2 | 3/2004 | Rondeau |
| 6,797,013 B1 | 9/2004 | Lang et al. |
| 6,863,883 B1 | 3/2005 | Tsujino et al. |

(Continued)

FOREIGN PATENT DOCUMENTS

BE    702 239    2/1968

(Continued)

OTHER PUBLICATIONS

STIC Search Report dated Oct. 8, 2008.*

(Continued)

*Primary Examiner*—Eisa B Elhilo
(74) *Attorney, Agent, or Firm*—Finnegan, Henderson, Farabow, Garrett & Dunner, LLP

(57) ABSTRACT

Disclosed herein is a mixed cationic direct dye comprising at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage. Also disclosed herein is a dyeing composition comprising at least one mixed cationic direct dye. Further disclosed herein is a method of dyeing of keratin fibers, for example, keratin fibers, comprising applying said dyeing composition to the keratin fibers. Still further disclosed herein is a multi-compartment kit comprising at least one compartment comprising at least one dye composition and at least one second compartment comprising at least one oxidizing agent.

67 Claims, No Drawings

U.S. PATENT DOCUMENTS

| | | | |
|---|---|---|---|
| 6,884,265 B2 | 4/2005 | Vidal et al. |
| 7,056,346 B1 | 6/2006 | Maubru |
| 7,172,633 B2 | 2/2007 | Samain et al. |
| 7,201,779 B2 | 4/2007 | Samain et al. |
| 7,261,743 B2 | 8/2007 | Plos et al. |
| 7,288,121 B2 | 10/2007 | Greaves et al. |
| 7,300,471 B2 | 11/2007 | Greaves et al. |
| 2001/0001332 A1 | 5/2001 | Henrion et al. |
| 2001/0001333 A1 | 5/2001 | Samain |
| 2001/0044975 A1 | 11/2001 | Matsunaga et al. |
| 2002/0002748 A1 | 1/2002 | Rondeau |
| 2002/0004956 A1 | 1/2002 | Rondeau |
| 2002/0165368 A1 | 11/2002 | Henrion et al. |
| 2003/0000023 A9 | 1/2003 | Rondeau |
| 2003/0066143 A1 | 4/2003 | Mockli |
| 2003/0163879 A1 | 9/2003 | Brennan et al. |
| 2003/0233713 A1 | 12/2003 | Quinn et al. |
| 2004/0187225 A1 | 9/2004 | Vidal et al. |
| 2005/0039268 A1 | 2/2005 | Plos et al. |

FOREIGN PATENT DOCUMENTS

| | | | |
|---|---|---|---|
| DE | 1 254 118 | | 11/1967 |
| DE | 25 27 638 | | 5/1976 |
| DE | 25 38 363 | | 5/1976 |
| DE | 33 35 956 | A1 | 4/1985 |
| DE | 41 28 490 | A1 | 3/1993 |
| DE | 41 37 005 | A1 | 5/1993 |
| DE | 42 20 388 | A1 | 12/1993 |
| DE | 198 02 940 | C2 | 8/1999 |
| DE | 198 45 640 | A1 | 4/2000 |
| DE | 101 44 881 | A1 | 3/2003 |
| EP | 0 318 294 | | 5/1989 |
| EP | 0 696 619 | B1 | 2/1996 |
| EP | 0 714 954 | | 6/1996 |
| EP | 0 714 954 | A2 | 6/1996 |
| EP | 0 758 547 | A1 | 2/1997 |
| EP | 0758 547 | A1 * | 2/1997 |
| EP | 0 810 851 | | 12/1997 |
| EP | 0 850 636 | A1 | 7/1998 |
| EP | 0 850 637 | A1 | 7/1998 |
| EP | 0 918 053 | A1 | 5/1999 |
| EP | 0 920 856 | A1 | 6/1999 |
| EP | 0 962 219 | | 12/1999 |
| EP | 1 022 016 | A2 | 7/2000 |
| EP | 1 062 940 | A1 | 12/2000 |
| EP | 1 133 975 | | 9/2001 |
| EP | 1 133 976 | A2 | 9/2001 |
| EP | 1 153 598 | B1 | 11/2001 |
| EP | 1 153 599 | | 11/2001 |
| EP | 1 175 893 | A2 | 1/2002 |
| FR | 1 221 122 | | 5/1960 |
| FR | 1 516 943 | | 3/1968 |
| FR | 1 540 423 | | 9/1968 |
| FR | 1 560 664 | | 3/1969 |
| FR | 1 567 219 | | 5/1969 |
| FR | 1 584 965 | | 1/1970 |
| FR | 2 189 006 | | 1/1974 |
| FR | 2 213 968 | | 8/1974 |
| FR | 2 275 462 | | 1/1976 |
| FR | 2 285 851 | | 4/1976 |
| FR | 2 570 946 | A1 | 4/1986 |
| FR | 2 586 913 | A1 | 3/1987 |
| FR | 2 741 798 | | 6/1997 |
| FR | 2 757 385 | A1 | 6/1998 |
| FR | 2 788 433 | A1 | 7/2000 |
| FR | 2 825 625 | A1 | 12/2002 |
| GB | 738 585 | | 10/1955 |
| GB | 769 163 | | 2/1957 |
| GB | 822 846 | | 11/1959 |
| GB | 1 047 796 | | 11/1966 |
| GB | 1 139 408 | | 1/1969 |
| GB | 1 163 385 | | 9/1969 |
| GB | 1 195 386 | | 6/1970 |
| GB | 1 199 641 | | 7/1970 |
| GB | 1 491 930 | | 11/1977 |
| GB | 1 514 466 | | 6/1978 |
| JP | A S40-021144 | | 9/1965 |
| JP | A S41-004102 | | 3/1966 |
| JP | A S53-139636 | | 12/1978 |
| JP | 60-215882 | | 10/1985 |
| JP | 61-218512 | | 9/1986 |
| JP | 2-292370 | | 12/1990 |
| JP | A H05-345862 | | 12/1993 |
| JP | A H09-111137 | | 4/1997 |
| JP | A H05-318938 | | 12/1997 |
| JP | 10-502946 | | 3/1998 |
| JP | 2000-505841 | | 5/2000 |
| JP | 2000-204026 | | 7/2000 |
| JP | 2000-281921 | | 10/2000 |
| JP | 2001-316231 | | 11/2001 |
| JP | A 2001-316230 | | 11/2001 |
| JP | 2002-37718 | | 2/2002 |
| JP | 2002-47153 | | 2/2002 |
| JP | A 2002-080332 | | 3/2002 |
| JP | 2003-300847 | | 10/2003 |
| WO | WO 95/01772 | | 1/1995 |
| WO | WO 95/15144 | | 6/1995 |
| WO | WO 97/44004 | | 11/1997 |
| WO | WO 99/48465 | | 9/1999 |
| WO | WO 00/71622 | A1 | 11/2000 |
| WO | WO 01/66646 | A1 | 9/2001 |
| WO | WO 02/30374 | | 4/2002 |
| WO | WO 02/31056 | A1 | 4/2002 |
| WO | WO 02/078596 | A2 | 10/2002 |
| WO | WO 03/006554 | | 1/2003 |
| WO | WO 03/018021 | A1 | 3/2003 |
| WO | WO 03/029359 | A1 | 4/2003 |
| WO | WO 03/030909 | A1 | 4/2003 |
| WO | WO 03/060015 | A1 | 7/2003 |
| WO | WO 2004/072183 | A1 | 8/2004 |

OTHER PUBLICATIONS

French Search Report for FR 0508793 (French priority application for the present application), dated Aug. 4, 2006, Examiner M. Ketterer.

Katsuhira Yoshida et al., "Butylamination of 1-Aminohalogenoanthraquinones Promoted by Metal Ions," Dyes and Pigments, vol. 2, pp. 125-132 (1981).

Todor G. Deligeorgiev et al., "One-pot Synthesis of 1,3-Dimethyl-2-[4-N(N,N-disubstitutedamino)phenylazo]imidazolium Cationic Dyes," Dyes and Pigments, vol. 31, No. 3, pp. 219-224 (1996).

French Search Report for FR 0450380 (French priority application for U.S. Appl. No. 11/066,459, issued as US-7,300,471), dated Oct. 6, 2004, Examiner J-M Yon.

French Search Report for French Application No. 03 07185 (Priority Application for U.S. Appl. No. 10/980,900, issued as US-7,201,799) dated Mar. 15, 2004, Examiner Irwin.

French Search Report for French Application No. 03 07186 (Priority Application for U.S. Appl. No. 10/980,899, issued as US-7,172,633) dated Mar. 11, 2004, Examiner Vayssié.

French Search Report for FR 04/50381 (French priority application for U.S. Appl. No. 11/066,467, issued as US-7,288,121) dated Oct. 14, 2004, Examiner J-M Yon.

English language abstract of DE 12 54 118, Nov. 16, 1967.
English language abstract of DE 25 27 638, May 6, 1976.
English language abstract of DE 33 35 956 A1, Apr. 18, 1985.
English language abstract of DE 41 28 490 A1, Mar. 4, 1993.
English language abstract of DE 41 37 005 A1, May 13, 1993.
English language abstract of DE 42 20 388 A1, Dec. 23, 1993.
English language abstract of DE 198 02 940 C2, Aug. 5, 1999.
English language abstract of JP A S40-021144, (1965).
English language abstract of JP A S41-004102, (1966).
English Language Derwent Abstract for JP A S53-139 636, (1978).
English language abstract of JP 60-215882, Oct. 29, 1985.

English language abstract of JP 2002-47153, Feb. 12, 2002.
Derwent Abstract of JP 55 022638 A.
Chemical Abstracts Service, Accession No. 72:134134 (XP0021880108) of JP 45 004332, (1970).
Chemical Abstracts Service, Accession No. 70:12645 (XP002188107).
Non-Final Office Action mailed Mar. 29, 2007, in U.S. Appl. No. 11/066,459, issued as US-7,300,471, filed Feb. 28, 2005.
Notice of Allowability mailed Dec. 27, 2004, in U.S. Appl. No. 10/473,624, filed Oct. 1, 2003, issued as US-6,884,265.
Notice of Allowability mailed Apr. 24, 2007, in U.S. Appl. No. 10/480,384, filed Oct. 14, 2004, issued as US-7,261,743.
Office Action mailed Aug. 18, 2006, in U.S. Appl. No. 10/480,384, filed Oct. 14, 2004, issued as US-7,261,743.
Notice of Allowability mailed Aug. 15, 2006, in U.S. Appl. No. 10/980,899, filed Jun. 16, 2004, issued as US-7,172,633.
Notice of Allowability mailed Dec. 12, 2006, in U.S. Appl. No. 10/980,900, filed Jun. 16, 2004, issued as US-7,201,779.
Office Action mailed Aug. 15, 2006, in U.S. Appl. No. 10/980,900, filed Jun. 16, 2004, issued as US-7,201,779.
Office Action mailed Mar. 29, 2007, in U.S. Appl. No. 11/066,459, filed Feb. 28, 2005, issued as US-7,300,471.
Notice of Allowability mailed Jul. 10, 2007, in U.S Appl. No. 11/066,459, filed Feb. 28, 2005, issued as US-7,300,471.
Supplemental Notice of Allowance mailed Sep. 7, 2007, in U.S. Appl. No. 11/066,459, filed Feb. 28, 2005, issued as US-7,300,471.
Notice of Allowability mailed Jul. 10, 2007, in U.S. Appl. No. 11/066,467, filed Feb. 28, 2005, issued as US-7,288,121.
Office Action mailed Mar. 29, 2007, in U.S. Appl. No. 11/066,467, filed Feb. 28, 2005, issued as US-7,288,121.
V.V. Stashkevich et al., "Bisformazans and Bistetrazolium Salts, Derivatives of Quaternary Salts of Quinaldine," Journal of General Chemistry of the USSR, Consultants Bureau, New York, vol. 40, No. 1, pp. 178-183, 1970.
G. Alberti, "Ricerche Sui Coloranti Cationici Per Fibra Agrilica,"La Chimica E L'Industria, vol. 56, No. 9, pp. 600-602 (1974).
Guido Alberti et al., "Cationic Dyes for Acrylic Fibres. V. Cationic Dyes Derived from Several Heterocyclic Amines with Two or More Heteroatoms," Annali di Chimica, vol. 65, pp. 305-314 (1975).
Guido Alberti et al., "Thermodynamic Features in Acrylic Fiber Dyeing with Basic Dyes," Textile Research Journal, vol. 54, pp. 105-107 (1984).
Alexandru T. Balaban et al., "Reactions of Pyrylium Salts with Nucleophiles, XX. Synthesis of 4-(n-pyridinium)-4'-dialkylaminoazobenzene and of 4-(4-dialkylaminophenylazo)-4'-(n-pyridinium)-biphenyl Derivatives," Revue Roumaine de Chmie, vol. 33, No. 4, pp. 377-383 (1988).
"Dyes and Dye Intermediate," *Kirk Othmer Encyclopedia of Chemical Technology*, 7$^{th}$ ed., Wiley and Sons (1993).
Holla et al., "Studies on Nitrofuran Heterocycles, Part I," Rev. Roum. Chim., vol. 33(No. 4), pp. 277-282 (1998).
Khim Tekhnol., vol. 22(No. 5) pp. 548-553 (1979).
A.F. Kuzentsova et al., "The Determination of Thickness of a Histological Section by Interference Microscopy," Tsitologiya, vol. 10, No. 3, pp. 403-405 (1968).
Von Alfred Kreutzberger et al., "Antikonvulsiva, IV, 2,4,6-Gemischtfunktionell substituierte 1,3,5-Triazine," Chemiker-Zeitung, vol. 111, pp. 241-245 (1987).
Lihua Jianyan, Huaxue Fence, vol. 29, No. 4, pp. 233-234 (1993).
Richard Neidlein et al, "Synthese von substituierten Pyridiniumsalzen," Monatshefte für Chemie, vol. 106, pp. 643-648 (1975).
Piero Savarino et al., "Disperse and Cationic Dyes from Aminophenyl-X-Axolo-Pyridines," Dyes and Pigments, vol. 11, pp. 163-172 (1989).
Robert M. Schelkun, "Subtype-Selective N-Methyl-D-aspartate Receptor Antagonists: Benzimidazalone and Hydantoin as Phenol Replacements," Journal of Medicinal Chemistry, vol. 43, No. 9, pp. 1892-1897 (2000).
Seidler et al., "The qualification of different ditetrazolium salts as indicators in the oxido-reductase historchemistry," Acta Histochem. vol. 61(1), pp. 48-52 (1978).
STIC Search Report dated Mar. 21, 2007, in U.S. Appl. No. 11/066,467, filed Feb. 28, 2005, issued as US-7,288,121.
STIC Search Report dated Mar. 21, 2007, in U.S. Appl. No. 11/066,459, filed Feb. 28, 2005, issued as US-7,300,471.
STIC Search Report dated Jun. 23, 2006, in U.S. Appl. No. 10/980,899, filed Jun. 16, 2004, issued as US-7,172,633.
Hsien-Ju Tien et al., "Synthesis of New Azo Dyestuff Containing a Sydnone Ring," Journal of the Chinese Chemical Society, vol. 45, pp. 209-211 (1998).
Guido Viscardi et al., "Disperse and Cationic Azo Dyes from Heterocyclic Intermediates," Dyes and Pigments, vol. 19, pp. 69-79 (1992).
K. Venkateraman, *The Chemistry of Synthetic Dye*, vol. 1 to 7 Academic Press (1952).
Feng-Wen Yen et al., "The Design and Synthesis of Bisazo Series Compound Used in Organophotoconductor," MRL Bull. Res. Dev., vol. 6, No. 2, pp. 21-27 (1992).

* cited by examiner

MIXED CATIONIC DYES COMPRISING AT LEAST ONE ANTHRAQUINONE CHROMOPHORE AND THEIR USE IN METHODS OF HAIR DYEING

This application claims benefit of priority under 35 U.S.C. § 119 to French Patent Application No. 05/08793, filed Aug. 26, 2005, the contents of which are incorporated herein by reference.

Disclosed herein are novel mixed cationic dyes comprising at least one anthraquinone chromophore and at least one cationic chromophore chosen from cationic azo chromophores and cationic hydrazone chromophores. Also disclosed herein are compositions for the dyeing of keratin fibers, for example, human keratin fibers such as the hair, comprising at least one mixed cationic dye as defined herein. Further disclosed herein are methods of dyeing keratin fibers comprising applying at least one composition of the present disclosure to the fibers. Still further disclosed herein are kits comprising at least one compartment containing at least one composition of the present disclosure.

The dyeing of keratin fibers, for instance, human hair, with dyeing compositions comprising direct dyes is known. These compounds comprise colored and coloring molecules possessing affinity for the fibers. For example, the use of direct dyes chosen from benzene nitro dyes, anthraquinone dyes, nitropyridine dyes, azo dyes, xanthene dyes, acridine dyes, azine dyes, and triarylmethane dyes is known.

Conventionally, these dyes are applied to the fibers, optionally in the presence of an oxidizing agent, if the user wishes to obtain a simultaneous effect of lightening of the fibers. After a waiting time, the fibers are rinsed, optionally washed and dried.

The coloring that results from the use of direct dyes is temporary or semipermanent coloring, since the interactions that bind the direct dyes to the keratin fiber, and their desorption from the surface and/or from the core of the fiber are responsible for their low coloring power and their relatively poor resistance to washing and/or sweat.

Keratin fibers such as the hair can be dyed in chromatic shades, such as red or orange, simultaneously with lightening of the natural color of the hair. Mixed together, the chromatic direct dyes may make it possible to obtain, also in lightening conditions, aesthetic natural shades. However, changes of the dyes over time, for example, due to successive shampooings, may alter the color, causing an undesirable change from the natural color to a more chromatic color.

Thus, the present disclosure provides direct dyes that may make it possible to obtain natural shades without at least one of the drawbacks of the existing direct dyes.

Disclosed herein are direct dyes with which varied shades may be obtained without the problem of color change over time, that may be resistant notably to shampooing, and may be non-selective, in lightening or non-lightening formulas.

Also disclosed herein are novel mixed cationic direct dyes comprising at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage.

The dyes disclosed herein may overcome at least one of the problems that are encountered in the prior art dyes. For example, they may make it possible to obtain dyeing in natural colors, in lightening conditions, which is uniform and is resistant, notably to shampooing.

Further disclosed herein is a composition for the oxidation dyeing of keratin fibers, for example, human keratin fibers such as the hair, comprising, in a medium suitable for dyeing, at least one mixed cationic dye as defined herein.

Still further disclosed herein is a method of dyeing of keratin fibers comprising applying at least one dyeing composition of the present disclosure to the fibers.

Also disclosed herein is a method of lightening dyeing of keratin fibers comprising applying at least one dyeing composition of the present disclosure and at least one oxidizing composition to the fibers.

Further disclosed herein are kits comprising at least one compartment containing at least one composition of the present disclosure.

Other characteristics, aspects, objects, and advantages of the present disclosure will become clearer upon reading the description and the examples given below.

As used herein, and unless a more precise indication is given:

An alkyl radical or the alkyl portion of a radical is said to be 'substituted' when it comprises at least one substituent chosen from:

hydroxyl groups,
$C_1$-$C_4$ alkoxy groups and $C_2$-$C_4$ (poly)-hydroxyalkoxy groups,
$C_1$-$C_2$ alkylcarbonylamino groups,
$C_1$-$C_4$ alkoxycarbonyl groups,
$C_1$-$C_4$ alkylsulphinyl groups,
$C_1$-$C_4$ alkylsulphonyl groups, and
amino groups and amino groups substituted with at least one $C_1$-$C_4$ alkyl group, which may be identical or different, optionally bearing at least one group, which may be identical or different, chosen from hydroxyl groups and $C_1$-$C_2$ alkoxy groups, wherein said alkyl radicals may form, together with the nitrogen atom to which they are attached, a heterocycle comprising 5 or 6 ring members, which may be saturated or unsaturated, optionally aromatic, chosen, for example, from pyrrolidine, piperazine, homopiperazine, pyrrole, imidazole, and pyrazole rings, and optionally comprising at least one other heteroatom which may or may not be nitrogen.

An aryl or heteroaryl radical or the aryl or heteroaryl portion of a radical is said to be 'substituted' when it comprises at least one substituent carried by a carbon atom, chosen from:

$C_1$-$C_{16}$, for example, $C_1$-$C_8$, alkyl radicals, optionally substituted with at least one radical chosen from hydroxy radicals, $C_1$-$C_2$ alkoxy radicals, $C_2$-$C_4$ (poly)-hydroxyalkoxy radicals, acylamino radicals, and amino radicals substituted with two $C_1$-$C_4$ alkyl radicals, which may be identical or different, optionally bearing at least one hydroxyl group, or the two radicals may form, together with the nitrogen atom to which they are attached, a heterocycle comprising 5, 6, or 7 ring members, for example, 5 or 6 ring members, and optionally comprising another heteroatom identical which may or may not be nitrogen;

halogen atoms such as chlorine, fluorine, and bromine;
hydroxyl groups;
$C_1$-$C_4$ alkoxy radicals and $C_2$-$C_4$ (poly)-hydroxyalkoxy radicals;
amino radicals and amino radicals substituted with one or two $C_1$-$C_4$ alkyl radicals, which may be identical or different, optionally bearing at least one group chosen from hydroxyl groups and amino groups optionally substituted with two optionally substituted $C_1$-$C_2$ alkyl radicals, or substituted with an optionally substituted aryl group;

carbamoyl radicals $(R_{53})_2N$—CO—, wherein the radicals $R_{53}$, which may be identical or different, are chosen from hydrogen and $C_1$-$C_4$ alkyl radicals optionally bearing at least one hydroxyl group;

alkylsulphonylamino radicals $R_{54}SO_2$—$NR_{55}$—, wherein the radical $R_{54}$ is chosen from $C_1$-$C_4$ alkyl radicals optionally bearing at least one hydroxyl group, phenyl radicals optionally bearing at least one radical chosen from $C_1$-$C_4$ alkyl radicals, hydroxyl radicals, and the radical $R_{55}$ is chosen from $C_1$-$C_4$ alkyl radicals and phenyl radicals;

aminosulphonyl radicals $(R_{56})_2N$—$SO_2$—, wherein the radicals $R_{56}$, which may be identical or different, are chosen from hydrogen and $C_1$-$C_4$ alkyl radicals optionally bearing at least one hydroxyl group, and alkylcarbonylamino groups $R_{57}CO$—$NR_{58}$—, wherein the radical $R_{57}$ is chosen from $C_1$-$C_4$ alkyl radicals and the radical $R_{58}$ is chosen from hydrogen and $C_1$-$C_4$ alkyl radicals.

This definition applies, for example, to aromatic rings present on an anthraquinone unit.

The cyclic or heterocyclic portion of a non-aromatic radical is said to be substituted when it comprises at least one substituent carried by a carbon atom, chosen from:

hydroxyl groups, $C_1$-$C_4$ alkoxy groups and $C_2$-$C_4$ (poly)-hydroxyalkoxy groups, alkylcarbonylamino groups ($R_{57}CO$—$NR_{58}$—), wherein the radical $R_{57}$ is chosen from $C_1$-$C_4$ alkyl radicals optionally bearing at least one hydroxyl group and the radical $R_{58}$ is chosen from hydrogen and $C_1$-$C_4$ alkyl radicals, and amino groups substituted with two $C_1$-$C_4$ alkyl groups, which may be identical or different, optionally bearing at least one hydroxyl group, wherein said alkyl radicals may form, together with the nitrogen atom to which they are attached, a heterocycle comprising 5 to 7 ring members, and optionally comprising at least one other heteroatom which may or may not be nitrogen.

In at least one embodiment, when a ring does not have the maximum number of substituents, the unsubstituted position(s) carry a hydrogen atom.

Furthermore, as the mixed dyes according to the present disclosure are cationic, their counter-ion(s) may be chosen from cosmetically acceptable anions and mixtures of anions, of organic or inorganic character. Examples of anions include halides, such as chlorides and bromides; hydroxides; sulphates; hydrogensulphates; carbonates; perchlorates, tetrafluoroborates, hydrogencarbonates, acetate; citrate; tartrate; alkylsulphates for which the alkyl portion, which may be linear or branched, comprises from 1 to 6 carbon atoms, such as methylsulphate and ethylsulphate ions; alkylsulphonates for which the alkyl portion, which may be linear or branched, comprises from 1 to 6 carbon atoms; arylsulphonates for which the aryl, for example, phenyl, portion is optionally substituted with at least one $C_1$-$C_4$ alkyl radical; and mixtures thereof.

Mixed Cationic Dyes

As discussed above, the mixed cationic dyes comprise at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage.

As used herein, chromophore means a radical from a dye, i.e., a radical of a molecule absorbing in the visible range from 400 to 800 nm. It is to be understood that this absorbance of the dye requires neither prior oxidation of the latter, nor combination with another chemical species.

According to one embodiment of the present disclosure, the mixed dye comprises two or three chromophores.

As used herein, a chromophore is said to be cationic when it comprises at least one quaternized nitrogen atom.

According to at least one embodiment, the cationic charge of the at least one chromophore may or may not be comprised in a ring.

According to another embodiment of the present disclosure, the mixed dye is chosen from compounds of formulas (Ia) and (Ib):

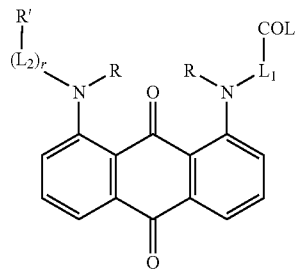

(Ia)

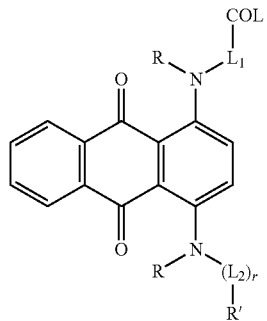

(Ib)

wherein:

$L_1$ is a linkage, which may be cationic or non-cationic, binding the first nitrogen atom of the anthraquinone to the group COL by means of an atom chosen from carbon, oxygen, and nitrogen, which may be optionally quaternized;

$L_2$ is a linkage, which may be cationic or non-cationic, binding the second nitrogen of the anthraquinone to the group R' by means of an atom chosen from carbon, oxygen, and nitrogen, which may be optionally quaternized;

r is equal to 0 or 1;

the groups R, which may be identical or different, are chosen from hydrogen and optionally substituted $C_1$-$C_4$ alkyl radicals; wherein at least one of the groups R may be optionally inserted in a saturated or unsaturated ring, optionally aromatic, comprising from 5 to 7 ring members, with $L_1$ or $L_2$;

R' is chosen from:

hydrogen, linear or branched $C_1$-$C_{12}$ hydrocarbon chains, which may be optionally substituted, optionally interrupted or terminated by at least one group chosen from amino groups, optionally substituted mono- or dialkylamino groups, optionally substituted alkyl groups, optionally substituted arylammonium groups, heterocycles comprising 5 or 6 ring members, which may be saturated or unsaturated, comprising at least one quaternized nitrogen atom inserted in said heterocycle, and a group COL;

COL is a coloring radical chosen from the cationic azo and cationic hydrazone families, when COL is a cationic azo radical, it is chosen from compounds of formula (IIa):

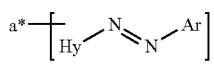

(IIa)

when COL is a cationic hydrazone radical, it is chosen from compounds of formula (IIb):

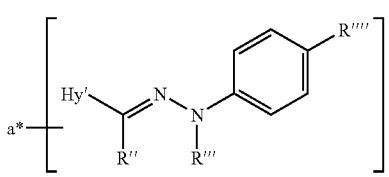

(IIb)

a* is a bond joining COL to L₁;

Hy is a cationic heterocycle chosen from compounds of formulas (IIIa) and (IIIb):

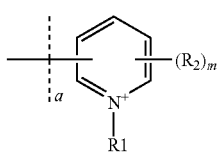

(IIIa)

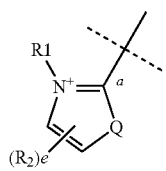

(IIIb)

Hy' is a cationic heterocycle chosen from compounds of formula (IIIa);

$R_1$, which may be identical or different, is chosen from linear or branched $C_1$-$C_{16}$ hydrocarbon chains, saturated or unsaturated, which may optionally form at least one carbon ring comprising from 5 to 7 ring members, optionally condensed with the aromatic ring, optionally substituted, optionally interrupted by at least one group chosen from heteroatoms such as oxygen, nitrogen, and sulphur, and carbonyl groups; wherein $R_1$ does not have a function chosen from nitro, nitroso, peroxide, and diazo functions, and wherein $R_1$ is directly attached to the nitrogen atom, which may be optionally quaternized, of the heteroaromatic ring by means of a carbon atom.

$R_2$, which may be identical or different, is chosen from:

linear or branched $C_1$-$C_{16}$ hydrocarbon chains, which may be saturated or unsaturated, aromatic or non-aromatic, which may optionally form at least one carbon ring comprising from 5 to 6 ring members, which may be optionally substituted, optionally interrupted by at least one entity chosen from heteroatoms and groups bearing at least one heteroatom, chosen, for example, from oxygen, nitrogen, and sulphur, such as —CO— and —SO₂—, and combinations thereof, hydroxyl groups, $C_1$-$C_4$ alkoxy groups and $C_2$-$C_4$ (poly)-hydroxyalkoxy groups, alkoxycarbonyl groups $R_{11}O$—CO—, wherein $R_{11}$ is chosen from $C_1$-$C_4$ alkyl radicals, alkylcarbonyloxy radicals $R_{12}CO$—O—, wherein $R_{12}$ is chosen from $C_1$-$C_4$ alkyl radicals, amino groups and amino groups substituted with one or two $C_1$-$C_4$ alkyl radicals, which may be identical or different, optionally bearing at least one hydroxyl group, wherein the two alkyl radicals may optionally form, together with the nitrogen atom to which they are attached, a heterocycle comprising 5 or 6 ring members and optionally bearing another heteroatom which may or may not be nitrogen, for example oxygen and sulphur;

alkylcarbonylamino groups $R_{13}CO$—$NR_{14}$—, wherein the radicals $R_{13}$ and $R_{14}$, which may be identical or different, are chosen from $C_1$-$C_4$ alkyl radicals, carbamoyl groups $(R_{15})_2N$—CO, wherein the radicals $R_{15}$, which may be identical or different, are chosen from hydrogen and $C_1$-$C_4$ alkyl radicals, ureido groups $(R_{16})_2N$—CO—$NR_{17}$—, wherein the radicals $R_{16}$ and $R_{17}$, which may be identical or different, are chosen from hydrogen and $C_1$-$C_4$ alkyl radicals;

sulphonamide groups $(R_{18})_2N$—$SO_2$—, wherein the radicals $R_{18}$, which may be identical or different, are chosen from hydrogen and $C_1$-$C_4$ alkyl radicals, alkylsulphonylamino groups $R_{19}SO_2$—$NR_{20}$—, wherein the radicals $R_{19}$ and $R_{20}$, which may be identical or different, are chosen from hydrogen and $C_1$-$C_4$ alkyl radicals;

guanidinium groups $(R_{21})_2N$—$C(=NH_2^+)$—$NR_{22}$—, wherein the radicals $R_{21}$, and $R_{22}$, which may be identical or different, are chosen from hydrogen and $C_1$-$C_4$ alkyl radicals;

alkylsulphonyl groups $R_{23}$—$SO_2$—, wherein $R_{23}$ is chosen from $C_1$-$C_4$ alkyl radicals;

nitro groups; cyano groups; and halogen atoms, for example, chlorine and fluorine; and optionally substituted phenyl groups;

two radicals $R_2$, carried by adjacent carbon atoms may form, together with the carbon atom to which each is attached, an optionally substituted condensed aromatic ring;

m is an integer ranging from 0 to 4; when m is less than 4, the unsubstituted carbon atom(s) of the heterocycle carry a hydrogen atom;

e is an integer ranging from 0 to 2; when e is less than 2, the unsubstituted carbon atom(s) of the heterocycle carry a hydrogen atom;

Q is chosen from $NR_1$, O, and S; and bond a in formulas (IIIa) and (IIIb) joins group Hy to the azo group —N=N—Ar of formula (IIa) or group Hy' to the hydrazone group —CR"=N—NR'"' of formula (IIb);

in the case of formulas (IIIa) or (IIIb), and when two radicals $R_2$ carried by two adjacent carbon atoms form an aromatic ring, bond a can join group Hy to the azo group —N=N— of formula (IIa) or group Hy' to the hydrazone group —CR"=N—NR'"'— of formula (IIb) by means of said aromatic ring;

Ar is an aromatic ring chosen from compounds of the following formula:

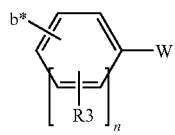

wherein:
b* is a bond joining Ar to NR''' of formula (IIb) or to the azo function of formula (IIa);
n is an integer ranging from 0 to 4; when n is less than 4, the unsubstituted carbon atom(s) of the aromatic ring carry a hydrogen atom;
$R_3$, which may be identical or different, is chosen from:
  $C_1$-$C_{16}$ alkyl radicals, optionally substituted, optionally interrupted by at least one entity chosen from heteroatoms and groups comprising at least one heteroatom, chosen, for example, from oxygen, nitrogen, and sulphur, such as —CO—, —$SO_2$—, and combinations thereof;
  hydroxyl groups;
  $C_1$-$C_4$ alkoxy groups and $C_2$-$C_4$ (poly)-hydroxyalkoxy groups;
  alkoxycarbonyl groups $R_{31}$O—CO—, wherein $R_{31}$ is chosen from $C_1$-$C_4$ alkyl radicals;
  alkylcarbonyloxy radicals $R_{32}$CO—O—, wherein $R_{32}$ is chosen from $C_1$-$C_4$ alkyl radicals;
  alkylcarbonyl radicals $R_{33}$—CO—, wherein $R_{33}$ is chosen from $C_1$-$C_4$ alkyl radicals;
  amino groups and amino groups substituted with one or two $C_1$-$C_4$ alkyl radicals, which may be identical or different, optionally bearing at least one hydroxyl group; wherein the two alkyl radicals may optionally form, together with the nitrogen atom to which they are attached, a heterocycle comprising from 1 to 3 heteroatoms, for example, from 1 to 2 heteroatoms, chosen, for example, from N, O, S, and in at least one embodiment, N, comprising from 5 to 7 ring members, which may be saturated or unsaturated, aromatic or non-aromatic, and optionally substituted;
  alkylcarbonylamino groups $R_{34}$CO—$NR_{35}$—, wherein the radical $R_{34}$ is chosen from $C_1$-$C_4$ alkyl radicals and the radical $R_{35}$ is chosen from hydrogen and $C_1$-$C_4$ alkyl radicals;
  aminocarbonyl groups $(R_{36})_2$N—CO—, wherein the radicals $R_{36}$, which may be identical or different, are chosen from hydrogen and $C_1$-$C_4$ alkyl radicals;
  ureido groups $N(R_{37})_2$—CO—$NR_{38}$—, wherein the radicals $R_{37}$ and $R_{38}$, which may be identical or different, are chosen from hydrogen and $C_1$-$C_4$ alkyl radicals;
  aminosulphonyl groups $(R_{39})_2$N—$SO_2$—, wherein the radicals $R_{39}$, which may be identical or different, are chosen from hydrogen and $C_1$-$C_4$ alkyl radicals;
  alkylsulphonylamino groups $R_{40}SO_2$—$NR_{41}$—, wherein the radicals $R_{40}$ and $R_{41}$, which may be identical or different, are chosen from hydrogen and $C_1$-$C_4$ alkyl radicals;
  thiol groups HS—;
  alkylthio groups $R_{42}$S—, wherein the radical $R_{42}$ is chosen from $C_1$-$C_4$ alkyl radicals;
  alkylsulphinyl groups $R_{43}$—SO—, wherein $R_{43}$ is chosen from $C_1$-$C_4$ alkyl radicals;
  alkylsulphonyl groups $R_{44}$—$SO_2$—, wherein $R_{44}$ is chosen from $C_1$-$C_4$ alkyl radicals;
  nitro groups;
  cyano groups;
  halogen atoms, for example, chlorine and fluorine;
when n is greater than or equal to 2, two adjacent radicals $R_3$ may form, together with the carbon atoms to which they are attached, a secondary ring, which may optionally be aromatic, comprising 6 ring members, and optionally substituted;
W is chosen from:
  hydrogen,
  halogen atoms chosen, for example, from bromine, chlorine, and fluorine, and it at least one embodiment, from chlorine and fluorine,
  —$NR_5R_6$, —$OR_7$, —$NR_4$-Ph-$NR_5R_6$, —$NR_4$-Ph-$OR_7$, —O-Ph-$OR_7$, —O-Ph-$NR_5R_6$, —$SO_2$—$NR_5R_6$, and —$SO_2$—$R_5$ groups; wherein:
  $R_4$ and $R_7$, which may be identical or different, are chosen from hydrogen, optionally substituted $C_1$-$C_{20}$, for example, $C_1$-$C_{16}$, alkyl radicals, and optionally substituted $C_6$-$C_{30}$ aryl and aralkyl radicals;
  $R_5$ and $R_6$, which may be identical or different, are chosen from hydrogen, optionally substituted $C_1$-$C_{20}$, for example, $C_1$-$C_{16}$, alkyl radicals, optionally substituted phenyl radicals, optionally substituted $C_6$-$C_{30}$ aryl and aralkyl radicals, and alkylcarbonyl radicals $R_{45}$—CO—, wherein $R_{45}$ is chosen from optionally substituted $C_1$-$C_4$ alkyl radicals;
  $R_5$ and $R_6$ may optionally form, together with the nitrogen atom to which they are attached, a heterocycle comprising from 1 to 3 heteroatoms chosen, for example, from N, O, and S, and in at least one embodiment, N, comprising from 5 to 7 ring members, saturated or unsaturated, aromatic or non-aromatic, and optionally substituted;
  $R_5$ and $R_6$, independently of one another, may form, together with the carbon atom of the aromatic ring adjacent to that to which —N $R_5R_6$ is attached, a saturated heterocycle with 5 or 6 ring members;
Ph is an optionally substituted phenyl radical;
R'' is chosen from:
  hydrogen,
  $C_1$-$C_{16}$ alkyl radicals, optionally substituted, optionally interrupted by at least one entity chosen from heteroatoms and groups comprising at least one heteroatom, chosen, for example, from oxygen, nitrogen, and sulphur, such as —CO— and —$SO_2$—, and combinations thereof;
  $C_6$-$C_{30}$ aryl and aralkyl radicals, such as phenyl and benzyl, the aryl portion being optionally substituted, for example, with at least one group, which may be identical or different, chosen, for example, from chlorine, amino groups, hydroxyl groups, $C_1$-$C_2$ alkoxy groups, amino groups which are mono- or disubstituted with two alkyl radicals, which may be identical or different, optionally bearing at least one hydroxyl group;
R''' is chosen from:
  hydrogen,
  $C_1$-$C_{16}$ alkyl radicals, optionally substituted, optionally interrupted by at least one entity chosen from heteroatoms and groups comprising at least one heteroatom, chosen, for example, from oxygen, nitrogen, and sulphur, such as —CO— and —$SO_2$—, and combinations thereof;

$C_6$-$C_{30}$ aryl and aralkyl radicals, such as phenyl and benzyl, the aryl portion being optionally substituted, for example, with at least one group, which may be identical or different, chosen, for example, from chlorine, amino groups, hydroxyl groups, $C_1$-$C_2$ alkoxy groups, amino groups mono- or disubstituted with two alkyl radicals, which may be identical or different, optionally bearing at least one hydroxyl group;

R'''' is chosen from hydrogen and halogen atoms chosen from bromine, chlorine, and fluorine, and in at least one embodiment, chlorine and fluorine, and —$OR_7$ groups.

bond a* may be located in a position chosen from:
  on one of the nitrogen atoms, optionally quaternized, of formulas (IIIa) and (IIIb),
  on one of the carbon atoms of the heterocycles of formulas (IIIa) and (IIIb),
  on one of the carbon atoms of the aromatic ring Ar,
  on the carbon atom bearing R'' or R''',
  on the nitrogen atom bearing the radicals $R_5$ and $R_6$, and
  on the oxygen atom bearing $R_7$,
  in which case the radical $R_1$, $R_2$, $R_3$, R'', R''', $R_5$, $R_6$, or $R_7$ in question is replaced by a single bond joining $L_1$ to COL;
  in the case when R' is the radical COL, $L_2$ is identical to $L_1$ and is joined in the same way to R' as $L_1$ to COL;
  the aromatic rings of the anthraquinone chromophores of formulas (Ia) and (Ib) may optionally be substituted;
  the electroneutrality of the compounds being provided by at least one, identical or different, cosmetically acceptable anion An-.

According to at least one embodiment, the groups R are chosen from hydrogen and $C_1$-$C_2$ alkyl radicals.

In another embodiment, R' is chosen from:
hydrogen,
linear or branched $C_1$-$C_6$ hydrocarbon chains, optionally substituted, which may optionally be interrupted or terminated by at least one group chosen from: amino, mono- or di-alkylamino, optionally substituted, and COL radicals.

According to yet another embodiment, $R_1$, which may be identical or different, is chosen from linear or branched $C_1$-$C_{10}$ hydrocarbon chains, which may be saturated or unsaturated, and which may form at least one carbon ring comprising 5 or 6 ring members, optionally condensed with the aromatic ring, and optionally substituted.

In a further embodiment, $R_2$, which may be identical or different, may be chosen from:
  linear or branched $C_1$-$C_{10}$ hydrocarbon chains, which may be saturated or unsaturated, which may form at least one carbon ring comprising 5 or 6 ring members, optionally substituted with at least one group, which may be identical or different, chosen, for example, from hydroxyl and $C_1$-$C_2$ alkoxy groups;
  hydroxyl groups,
  $C_1$-$C_4$ alkoxy groups,
  alkoxycarbonyl groups $R_{11}$O—CO—, wherein $R_{11}$ is chosen from $C_1$-$C_2$ alkyl radicals,
  alkylcarbonyloxy radicals $R_{12}$CO—O—, wherein $R_{12}$ is chosen from $C_1$-$C_2$ alkyl radicals;
  amino groups and amino groups substituted with one or two $C_1$-$C_4$ alkyl radicals, which may be identical or different, optionally bearing at least one hydroxyl group, wherein the two alkyl radicals may optionally form, together with the nitrogen atom to which they are attached, a heterocycle comprising 5 or 6 ring members optionally bearing another heteroatom, which may or may not be nitrogen, for example, oxygen and sulphur;
  alkylcarbonylamino groups $R_{13}$CO—$NR_{14}$—, wherein the radicals $R_{13}$ and $R_{14}$, which may be identical or different, are chosen from $C_1$-$C_2$ alkyl radicals;
  carbamoyl groups $(R_{15})_2$N—CO, wherein the radicals $R_{15}$, which may be identical or different, are chosen from hydrogen and $C_1$-$C_2$ alkyl radicals;
  ureido groups $(R_{16})_2$N—CO—$NR_{17}$—, wherein the radicals $R_{16}$ and $R_{17}$, which may be identical or different, are chosen from hydrogen and $C_1$-$C_4$ alkyl radicals;
  sulphonamide groups $(R_{18})_2$N—$SO_2$—, wherein the radicals $R_{18}$, which may be identical or different, are chosen from hydrogen and $C_1$-$C_4$ alkyl radicals;
  guanidinium groups $(R_{21})_2$N—C($=NH_2^+$)—$NR_{22}$—, wherein the radicals $R_{21}$ and $R_{22}$, which may be identical or different, are chosen from hydrogen and $C_1$-$C_4$ alkyl radicals;
  alkylsulphonyl groups $R_{23}$—$SO_2$—, wherein $R_{23}$ is chosen from $C_1$-$C_4$ alkyl radicals;
  cyano groups;
  halogen atoms, for example, chlorine and fluorine; and optionally substituted phenyl groups.

According to still a further embodiment, the radicals $R_2$, which may be identical or different, are chosen from methyl, ethyl, 2-hydroxyethyl, 2-methoxyethyl, methylsulphonyl ($CH_3SO_2$—), methylcarbonylamino ($CH_3CONH$—), hydroxyl, amino, methylamino, dimethylamino, 2-hydroxyethylamino, bis(2-hydroxyethyl)amino, methoxy, ethoxy, and phenyl radicals.

According to another embodiment, the radicals of formulas (IIIa) and (IIIb) carry two radicals $R_2$, and these radicals $R_2$ form, together with the carbon atoms to which they are attached, a secondary ring, which is aromatic and comprises 6 ring members, optionally substituted with at least one group, which may be identical or different, chosen from hydroxyl radicals, $C_1$-$C_4$ alkyl radicals, $C_1$-$C_4$ alkoxy radicals, amino radicals, amino radicals substituted with one or two $C_1$-$C_4$ alkyl radicals, which may be identical or different, and optionally bearing at least one group chosen from hydroxyl and methylcarbonylamino groups.

In yet another embodiment, the two radicals $R_2$ may form, together with the carbon atoms to which they are attached, a secondary ring, which is aromatic and comprises 6 ring members, and optionally substituted with one or more groups chosen from hydroxyl, methoxy, ethoxy, amino, 2-hydroxyethylamino, dimethylamino, and bis(2-hydroxyethyl)amino groups.

According to a further embodiment, m is an integer ranging from 0 to 2.

In a still further embodiment, e ranges from 0 to 2, and in at least one embodiment, e is equal to 0.

According to another embodiment, the radicals $R_3$, which may be identical or different, are chosen from:
  optionally substituted $C_1$-$C_{16}$ alkyl radicals,
  hydroxyl groups,
  $C_1$-$C_2$ alkoxy groups and $C_2$-$C_4$ (poly)-hydroxyalkoxy groups;
  alkoxycarbonyl groups $R_{31}$O—CO—, wherein $R_{31}$ is chosen from $C_1$-$C_4$ alkyl radicals;
  alkylcarbonyloxy radicals $R_{32}$CO—O—, wherein $R_{32}$ is chosen from $C_1$-$C_4$ alkyl radicals;
  alkylcarbonyl radicals $R_{33}$—CO—, wherein $R_{33}$ is chosen from $C_1$-$C_4$ alkyl radicals;
  amino groups and amino groups substituted with one or two $C_1$-$C_4$ alkyl radicals, which may be identical or different, optionally bearing at least one hydroxyl group; wherein the two alkyl radicals may optionally form, together with the nitrogen atom to which they are attached, a heterocycle comprising from 1 to 3 heteroatoms, for example, 1 to 2 heteroatoms, chosen from N, O, and S, and in at least one embodiment, N, comprising from 5 to 7 ring members, saturated or unsaturated, aromatic or non-aromatic, and optionally substituted;

alkylcarbonylamino groups $R_{34}CO$—$NR_{35}$—, wherein the radical $R_{34}$ is chosen from $C_1$-$C_4$ alkyl radicals and the radical $R_{35}$ is chosen from hydrogen and $C_1$-$C_4$ alkyl radicals;

aminocarbonyl groups $(R_{36})_2N$—CO—, wherein the radicals $R_{36}$, which may be identical or different are chosen from hydrogen and $C_1$-$C_4$ alkyl radicals;

ureido groups $N(R_{37})_2$—CO—$NR_{38}$—, wherein the radicals $R_{37}$ and $R_{38}$, which may be identical or different, are chosen from hydrogen and $C_1$-$C_4$ alkyl radicals;

aminosulphonyl groups $(R_{39})_2N$—$SO_2$—, wherein the radicals $R_{39}$, which may be identical or different, are chosen from hydrogen and $C_1$-$C_4$ alkyl radicals;

alkylsulphonylamino groups $R_{40}SO_2$—$NR_{41}$—, wherein the radicals $R_{40}$ and $R_{41}$, which may be identical or different, are chosen from hydrogen and $C_1$-$C_4$ alkyl radicals;

thiol groups HS—;

alkylthio groups $R_{42}S$—, wherein the radical $R_{42}$ is chosen from $C_1$-$C_4$ alkyl radicals;

alkylsulphonyl groups $R_{44}$—$SO_2$—, wherein $R_{44}$ is chosen from $C_1$-$C_4$ alkyl radicals;

cyano groups; and halogen atoms such as chlorine and fluorine.

According to a further embodiment, the radicals $R_3$, which may be identical or different, are chosen from:

$C_1$-$C_4$ alkyl radicals optionally substituted with at least one radical, which may be identical or different, chosen from hydroxyl radicals, $C_1$-$C_2$ alkylcarbonylamino radicals, and amino radicals substituted with two $C_1$-$C_2$ alkyl radicals, which may be identical or different, optionally bearing at least one group, which may be identical or different, chosen from hydroxyl and $C_1$-$C_2$ alkoxy groups; wherein these two alkyl radicals may optionally form, together with the nitrogen atom to which they are attached, a heterocycle comprising 5 or 6 ring members, which may be saturated or unsaturated, and optionally aromatic, chosen, for example, from pyrrolidine, piperazine, homopiperazine, pyrrole, imidazole, and pyrazole rings;

$C_1$-$C_4$ alkyl radicals optionally interrupted by at least one entity chosen from heteroatoms and groups comprising at least one heteroatom, chosen, for example, from oxygen, nitrogen, and sulphur, such as —CO— and —$SO_2$—, and combinations thereof $C_2$-$C_4$ hydroxyalkoxy radicals;

halogen atoms chosen from chlorine and fluorine;

amino radicals;

amino radicals substituted with one or two $C_1$-$C_2$ alkyl radicals, which may be identical or different, optionally bearing at least one hydroxyl group;

methylcarbonylamino radicals;

methylsulphonylamino radicals;

hydroxyl radicals;

$C_1$-$C_2$ alkoxy radicals; and methylsulphonyl radicals.

According to another embodiment, the radicals $R_3$, which may be identical or different, are chosen from:

methyl, ethyl, propyl, and 2-hydroxyethyl radicals;

methoxy and ethoxy radicals;

2-hydroxyethyloxy and 3-hydroxypropyloxy radicals;

2-methoxyethyl radicals;

methylsulphonylamino radicals;

amino, methylamino, dimethylamino, and 2-hydroxyethylamino radicals;

methylcarbonylamino radicals;

hydroxyl radicals;

chlorine; and methylsulphonyl radicals.

In at least one embodiment, when the coefficient n is greater than or equal to 2, two adjacent radicals $R_3$ may form, together with the carbon atoms to which they are attached, a secondary aromatic ring comprising 6 ring members, optionally substituted with at least one group, which may be identical or different, chosen from hydroxyl radicals, $C_1$-$C_4$ alkyl radicals, $C_1$-$C_4$ alkoxy radicals, $C_2$-$C_4$ (poly)-hydroxyalkoxy radicals, $C_1$-$C_4$ alkylcarbonylamino radicals, amino radicals, amino radicals substituted with one or two radicals, which may be identical or different, $C_1$-$C_4$ alkyl radicals optionally bearing at least one hydroxyl, and aryl groups.

According to another embodiment, two adjacent radicals $R_3$ may form, together with the carbon atoms to which they are attached, a secondary aromatic ring comprising 6 ring members, optionally substituted with at least one group chosen from hydroxyl radicals, methoxy radicals, ethoxy radicals, 2-hydroxyethyloxy radicals, amino radicals, methylcarbonylamino radicals, (di)2-hydroxyethylamino radicals, —NH-Ph groups, —NH-Ph-$NH_2$ groups, —NH-Ph-NH-$COCH_3$ groups, —NH-Ph-OH groups, and —NH-Ph-$OCH_3$ groups.

In yet another embodiment, n is an integer ranging from 0 to 2.

According to yet another embodiment, $R_4$ and $R_7$, which may be identical or different, are chosen from:

hydrogen;

$C_1$-$C_6$ alkyl radicals optionally substituted with at least one group, which may be identical or different, chosen, for example, from hydroxyl and $C_1$-$C_2$ alkoxy groups; and aryl and aralkyl radicals, such as phenyl and benzyl, the aryl portion being optionally substituted with at least one group, which may be identical or different, chosen, for example, from chlorine, amino groups, hydroxyl groups, $C_1$-$C_2$ alkoxy groups, amino groups mono- or disubstituted with two alkyl radicals, which may be identical or different, and optionally bearing at least one hydroxyl group;

In a further embodiment, the radicals $R_4$ and $R_7$, which may be identical or different, are chosen from:

hydrogen;

$C_1$-$C_3$ alkyl radicals, optionally substituted, such as methyl, ethyl, 2-hydroxyethyl, and 2-methoxyethyl radicals; and phenyl radicals, optionally substituted with at least one radical, which may be identical or different, chosen from hydroxyl radicals, $C_1$-$C_2$ alkoxy radicals, amino radicals, amino radicals substituted with at least one $C_1$-$C_4$ alkyl group optionally bearing at least one hydroxyl group.

According to a still further embodiment, the radicals $R_4$ and $R_7$, which may be identical or different, are chosen from:

hydrogen;

methyl, ethyl, and 2-hydroxyethyl radicals; and phenyl radicals, optionally substituted with at least one radical, which may be identical or different, chosen from hydroxyl, methoxy, amino, (di)methylamino, and (di) (2-hydroxyethyl)amino radicals.

In at least one embodiment, $R_5$ and $R_6$, which may be identical or different, are chosen from:
hydrogen;
alkylcarbonyl radicals $R_{45}$—CO—, wherein $R_{45}$ is chosen from optionally substituted $C_1$-$C_4$ alkyl radicals,
$C_1$-$C_6$ alkyl radicals optionally substituted with at least one group, which may be identical or different, chosen from hydroxyl, $C_1$-$C_2$ alkoxy, amino, and $C_1$-$C_4$ (di-)alkyl amino groups; wherein the alkyl radical may be substituted with at least one group, which may be identical or different, chosen from $C_1$-$C_4$ alkylsulphonyl, $C_1$-$C_4$ alkylsulphinyl, and $C_1$-$C_4$ alkylcarbonyl groups, and
aryl and aralkyl radicals such as phenyl and benzyl, the aryl portion being optionally substituted, for example, with at least one entity chosen from chlorine, amino groups, hydroxyl groups, $C_1$-$C_4$ alkoxy groups, amino groups mono- or di-substituted with two radicals, which may be identical or different, chosen from $C_1$-$C_4$ alkyl radicals optionally bearing at least one hydroxyl group.

In another embodiment, the radicals $R_5$ and $R_6$, which may be identical or different, are chosen from:
hydrogen;
methylcarbonyl, ethylcarbonyl, and propylcarbonyl radicals;
optionally substituted $C_1$-$C_3$ alkyl radicals, such as methyl, ethyl, 2-hydroxyethyl, and 2-methoxyethyl radicals; and
phenyl radicals, optionally substituted with at least one radical, which may be identical or different, chosen from hydroxyl radicals, $C_1$-$C_2$ alkoxy radicals, amino radicals, amino radicals substituted with at least one $C_1$-$C_4$ alkyl group optionally bearing at least one hydroxyl group.

According to yet another embodiment of the present disclosure, the radicals $R_5$ and $R_6$, which may be identical or different, are chosen from:
hydrogen;
methyl, ethyl, and 2-hydroxyethyl radicals;
methylcarbonyl, ethylcarbonyl, and propylcarbonyl radicals; and
phenyl radicals, optionally substituted with at least one radical chosen from hydroxyl, methoxy, amino, (di)methylamino, and (di)(2-hydroxyethyl)amino radicals.

According to a further embodiment, the radicals $R_5$ and $R_6$ may form, together with the nitrogen atom to which each is attached, a heterocycle comprising from 1 to 2 heteroatoms, chosen from N, O, and S, and in at least one embodiment, N, comprising from 5 to 7 ring members, saturated or unsaturated, aromatic or non-aromatic, and optionally substituted.

In at least one embodiment, the heterocycle comprising from 5 to 7 ring members is chosen from piperidine, piperazine, homopiperazine, pyrrole, imidazole, and pyrazole heterocycles, optionally substituted with at least one radical, which may be identical or different, chosen, for example, from hydroxyl radicals, $C_1$-$C_2$ alkoxy radicals, amino radicals, and amino radicals substituted with at least one $C_1$-$C_4$ alkyl group optionally bearing at least one hydroxyl group.

According to another embodiment, the radicals $R_5$ and $R_6$ may form, together with the nitrogen atom to which each is attached, a heterocycle comprising from 5 to 7 ring members, chosen from piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxy piperazine, homopiperazine, 1-methyl-1,4-perhydrodiazepine, pyrrole, 1,4-dimethylpyrrole, 1-methyl-4-ethylpyrrole, and 1-methyl-4-propylpyrrole.

In yet another embodiment, the radicals $R_5$ and $R_6$ may form, together with the carbon atom of the aromatic ring optionally substituted with a hydroxyl and adjacent to that to which —$NR_5R_6$ is attached, a saturated heterocycle comprising 5 or 6 ring members or saturated condensed heterocycles with 5 or 6 ring members.

According to a further embodiment, when W is —$NR_5R_6$ and bond b* is in the position para to —$NR_5R_6$, the group —$NR_5R_6$, with the aromatic nucleus optionally substituted with a hydroxyl is chosen from:

wherein:
t is equal to 0 or 1,
$R_5$ is as defined above, and
b* is as defined above.

According to a further embodiment, R" is chosen from hydrogen and optionally substituted $C_1$-$C_{10}$ alkyl radicals.

In another embodiment, R'" is chosen from hydrogen and optionally substituted $C_1$-$C_{10}$ alkyl radicals.

In at least one embodiment, bond a* is located in a position chosen from:
on one of the nitrogen atoms, quaternized or not, of formulas (IIIa) and (IIIb),
on the nitrogen atom bearing the radicals $R_5$ and $R_6$, and
on one of the atoms of the group $R_5$, $R_6$, or $R_7$.

According to one embodiment, at least one of the linkages $L_1$ and $L_2$ is a nonionic linkage.

In another embodiment, $L_1$ and $L_2$, which may be identical or different, are chosen from:
$C_1$-$C_{20}$ alkylene radicals, optionally substituted, optionally interrupted by a saturated or unsaturated (hetero)cycle, aromatic or non-aromatic, comprising from 3 to 7 ring members, optionally substituted, optionally condensed; said alkylene radical being optionally interrupted by at least one entity chosen from heteroatoms and groups comprising at least one heteroatom, for example, oxygen, nitrogen, and sulphur, such as —CO— and —$SO_2$—, and combinations thereof; the linkage $L_1$ and/ or $L_2$ not comprising a function chosen from azo, nitro, nitroso, and peroxo functions, wherein
$L_2$ is a covalent bond, when R' is different from COL.
$L_1$ and $L_2$, which may be identical or different, may also be chosen from alkylene radicals chosen from methylene, ethylene, linear or branched propylene, linear or branched butylene, linear or branched pentylene, linear or branched hexylene, optionally substituted and/or interrupted by at least one entity chosen from heteroatoms and groups comprising at least one heteroatom, chosen, for example, from oxygen, nitrogen, and sulphur, such as —CO— and —$SO_2$—, and combinations thereof; the linkage $L_1$ and/or $L_2$ not comprising a function chosen from azo, nitro, nitroso, and peroxo functions.

In yet another embodiment, $L_1$ and $L_2$, which may be identical or different, are chosen from alkylene radicals substituted with at least one group, which may be identical or different, chosen from hydroxyl, $C_1$-$C_2$ alkoxy, $C_1$-$C_2$ dialkylamino, alkyl($C_1$-$C_4$)carbonyl, and alkyl($C_1$-$C_4$)sulphonyl groups.

In a further embodiment, the cycle or heterocycle, saturated or unsaturated, aromatic or non-aromatic, which may interrupt the alkylene radical of the linkage $L_1$ and/or $L_2$ is chosen from phenylene, naphthylene, phenanthrylene, triazinyl, pyrimidinyl, pyridinyl, pyridazinyl, quinoxalinyl, and cyclohexyl.

According to still a further embodiment, $L_1$ and $L_2$, which may be identical or different are chosen from:

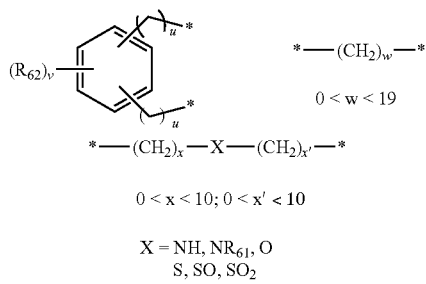

$0 < x < 10; 0 < x' < 10$ $X = NH, NR_{61}, O$
$S, SO, SO_2$ wherein:
u is equal to 0 or 1;
v is an integer ranging from 0 to 4;
$R_{61}$ is chosen from $C_1$-$C_4$ alkyl radicals optionally substituted with at least one radical, which may be identical or different, chosen from hydroxyl, $C_1$-$C_2$ alkoxy, $C_2$-$C_4$ (poly)-hydroxyalkoxy, amino, $C_1$-$C_2$ (di-) alkylamino, and aryl radicals, which may be optionally substituted
$R_{62}$ has the same definition as $R_3$; and
* is the end of the linkages $L_1$ and/or $L_2$;

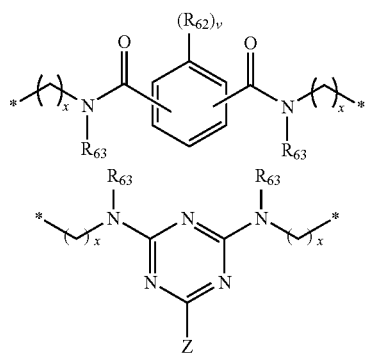

wherein:
x is an integer ranging from 0 to 6;
v is an integer ranging from 0 to 4;
Z is chosen from OH and $NR_{64}R_{65}$;
$R_{62}$ has the same definition as $R_3$;
$R_{63}$, which may be identical, are chosen from hydrogen and $C_1$-$C_4$ alkyl radicals;
$R_{64}$ and $R_{65}$, which may be identical or different, are chosen from hydrogen and $C_1$-$C_8$ alkyl radicals optionally substituted with at least one radical, which may be identical or different, chosen from hydroxyl, $C_1$-$C_2$ alkoxy, $C_2$-$C_4$ (poly)-hydroxyalkoxy, amino, $C_1$-$C_2$ (di-) alkylamino, and aryl radicals, which may be optionally substituted, and

* is the end of the linkages $L_1$ and/or $L_2$; and

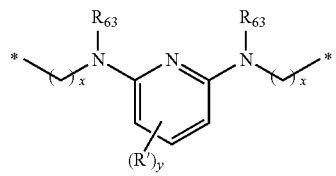

wherein:
x is an integer ranging from 0 to 6;
y is an integer ranging from 0 to 3;
R' has the same definition as $R_3$;
$R_{63}$, which may be identical, are chosen from hydrogen and $C_1$-$C_4$ alkyl radicals; and
* is the end of the linkages $L_1$ and/or $L_2$.

According to another embodiment of the present disclosure, at least one of the linkages $L_1$ and $L_2$ is a linkage carrying at least one cationic charge.

In yet another embodiment, $L_1$ and $L_2$, which may be identical or different, are chosen from $C_2$-$C_{40}$ alkylene radicals, carrying at least one cationic charge, optionally substituted and/or optionally interrupted by at least one (hetero) cycle, saturated or unsaturated, aromatic or non-aromatic, identical or different, comprising from 5 to 7 ring members and/or optionally interrupted by at least one entity chosen from heteroatoms and groups comprising at least one heteroatom, for example, oxygen, nitrogen, and sulphur, —CO— and —SO$_2$—, and combinations thereof; the linkage $L_1$ and/or $L_2$ not comprising a function chosen from azo, nitro, nitroso, and peroxo functions.

According to a further embodiment, the at least one cationic charge is carried by at least one quaternized nitrogen atom, optionally inserted in a heterocycle comprising from 5 to 6 ring members, saturated or unsaturated, substituted or unsubstituted, and optionally comprising at least one heteroatom chosen from oxygen, sulphur, and nitrogen, and in at least one embodiment, nitrogen.

In still a further embodiment, the cationic linkage $L_1$ and/or $L_2$ is chosen from $C_2$-$C_{20}$ alkyl radicals:
interrupted by at least one group chosen from:

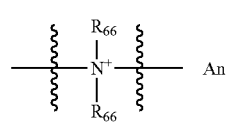

(a)

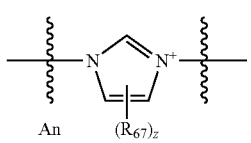

(b)

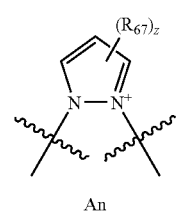

(c)

-continued

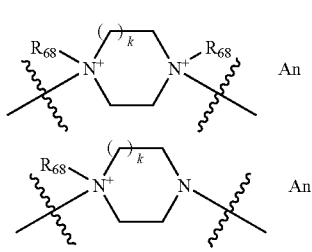

(d)

wherein:
$R_{66}$ and $R_{68}$, which may be identical or different, are chosen from $C_1$-$C_8$ alkyl radicals; $C_1$-$C_6$ monohydroxyalkyl radicals; $C_2$-$C_6$ polyhydroxyalkyl radicals; $C_1$-$C_6$ alkoxy($C_1$-$C_6$)alkyl radicals; aryl radicals, such as phenyl, optionally substituted; aralkyl radicals, such as benzyl, optionally substituted; $C_1$-$C_6$ aminoalkyl radicals; $C_1$-$C_6$ aminoalkyl radicals in which the amine is substituted with one or two $C_1$-$C_4$ alkyl radicals which may be identical or different, and alkyl($C_1$-$C_6$)sulphonyl radicals, two radicals $R_{66}$ may form, together with the nitrogen atom to which they are attached, a saturated or unsaturated ring, optionally substituted, comprising 5, 6, or 7 ring members, two radicals $R_{68}$ may form, together with the nitrogen atom to which they are attached, a saturated ring comprising 6 ring members, $R_{67}$, which may be identical or different, is chosen from halogen atoms chosen from bromine, chlorine, and fluorine, $C_1$-$C_6$ alkyl radicals, $C_1$-$C_6$ monohydroxyalkyl radicals, $C_2$-$C_6$ polyhydroxyalkyl radicals, $C_1$-$C_6$ alkoxy radicals, $C_1$-$C_4$ (di-)alkylamino radicals, hydroxycarbonyl radicals, $C_1$-$C_6$ alkylcarbonyl radicals, $C_1$-$C_6$ thioalkyl radicals, alkyl($C_1$-$C_6$)sulphonyl radicals, optionally substituted benzyl radicals, phenyl radicals optionally substituted with at least one radical chosen from methyl, hydroxyl, amino, and methoxy radicals, An chosen from anions and mixtures of anions, which may be organic or inorganic, z is an integer ranging from 1 to 3; if z is less than 3, then the unsubstituted carbon atoms carry a hydrogen atom, and k is an integer equal to 1 or 2, and in at least one embodiment, 1.

According to another embodiment, $L_1$ and/or $L_2$, which may be identical or different, may optionally be interrupted by at least one entity chosen from heteroatoms and groups comprising at least one heteroatom, for example, oxygen, nitrogen, sulphur, —CO—, and —$SO_2$—; with the proviso that $L_1$ and/or $L_2$ do not comprise a function chosen from nitro, nitroso, and peroxo functions (groups or bonds).

In yet another embodiment, $L_1$ and/or $L_2$, which may be identical or different, may optionally be substituted with at least one radical chosen from hydroxyl radicals, $C_1$-$C_2$ alkoxy radicals, $C_2$-$C_4$ (poly)-hydroxyalkoxy radicals, amino radicals substituted with at least one linear or branched $C_1$-$C_2$ alkyl groups optionally bearing at least one hydroxyl group.

According to a further embodiment, the radicals $R_{66}$ and $R_{68}$ in formulas (a) and (d), which may be identical or different, are chosen from $C_1$-$C_6$ alkyl radicals, $C_1$-$C_4$ monohydroxyalkyl radicals, $C_2$-$C_4$ polyhydroxyalkyl radicals, $C_2$-$C_4$ alkoxy($C_1$-$C_6$)alkyl radicals, and $C_2$-$C_6$ dimethylaminoalkyl radicals.

In a still further embodiment, the radicals $R_{66}$ and $R_{68}$, which may be identical or different, are chosen from methyl, ethyl, and 2-hydroxyethyl radicals.

According to another embodiment, the radical $R_{67}$ in formulas (b) and (c) are chosen from halogen atoms chosen from chlorine and fluorine, $C_1$-$C_6$ alkyl radicals, $C_1$-$C_4$ monohydroxyalkyl radicals, $C_1$-$C_4$ alkoxy radicals, hydroxycarbonyl radicals, $C_1$-$C_6$ thioalkyl radicals, amino radicals disubstituted with a $C_1$-$C_4$ alkyl radical.

In yet another embodiment, the radical $R_{67}$ in formulas (b) and (c) is chosen from chlorine, methyl radicals, ethyl radicals, 2-hydroxyethyl radicals, methoxy radicals, hydroxycarbonyl radiacls, and dimethylamino radicals.

In a further embodiment, z in formulas (b) and (c) is equal to 0.

According to at least one embodiment, the mixed dyes useful in hair dyeing compositions according to the present disclosure may be chosen from:

anthraquinones joined to two azo chromophores in azoimidazolium series:

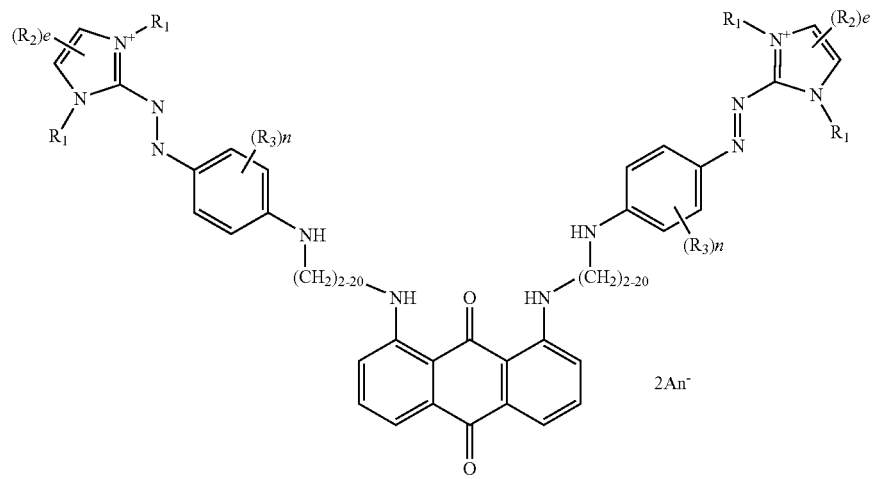

19
anthraquinones joined to an azo chromophore in azo-imidazotium series:
20
anthraquinones joined to two azo chromophores in 3-azo-pyridinium series:
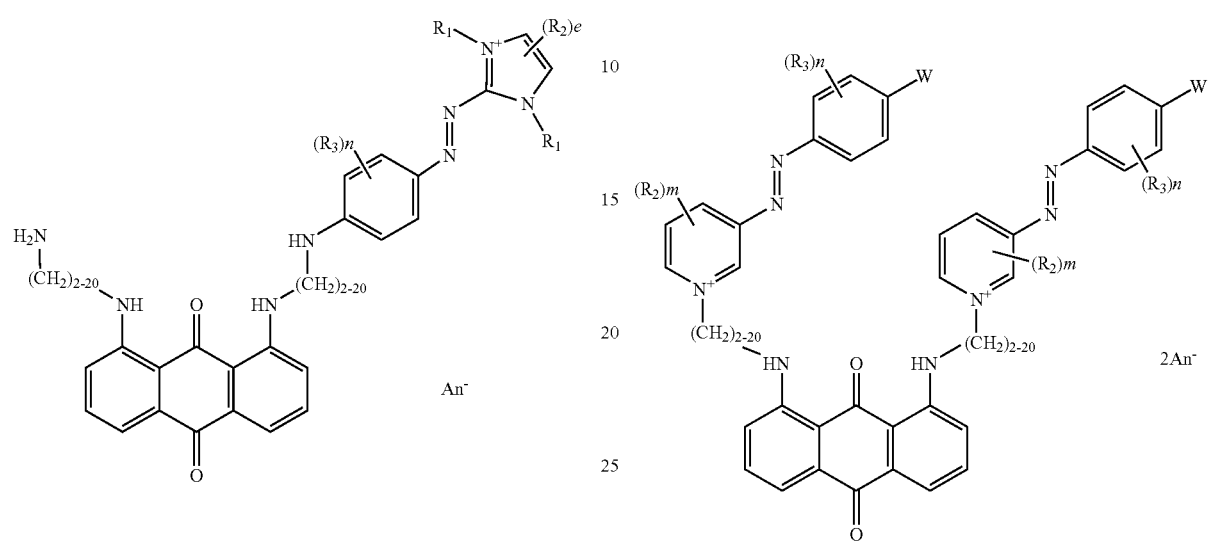
anthraquinones joined to two azo chromophores in azo-imidazolium series:
anthraquinones joined to two hydrazone chromophores in 4-pyridinium series:
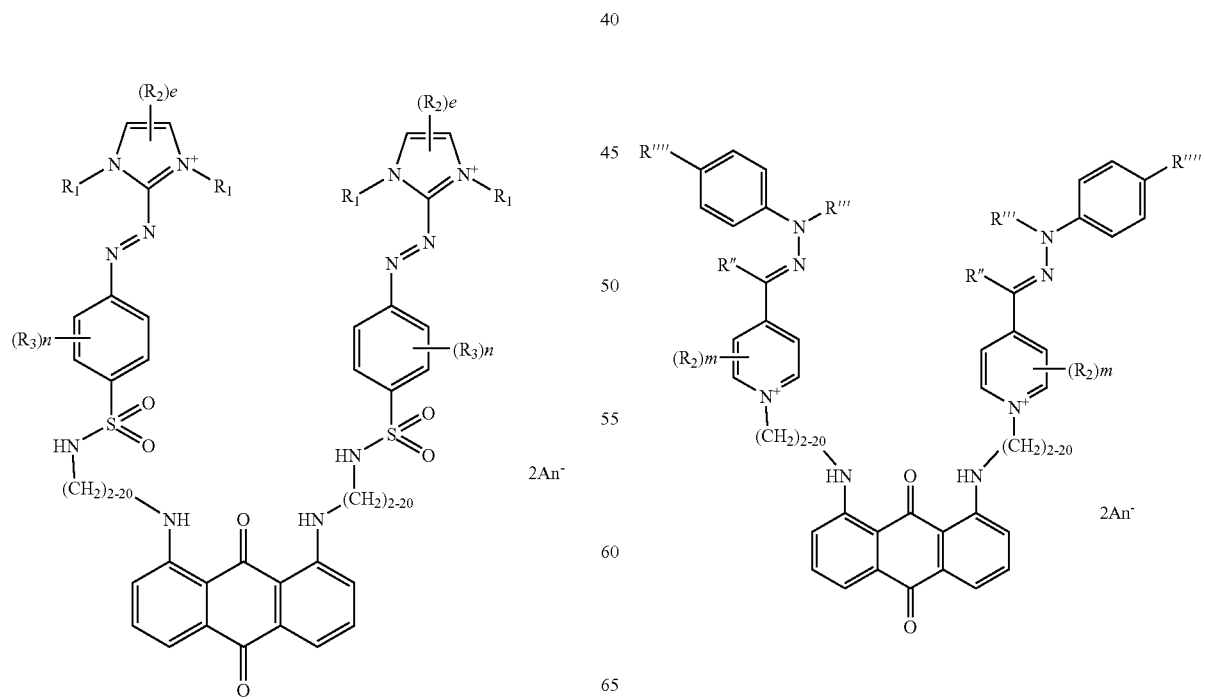

anthraquinones joined to two hydrazone chromophores in 4-pyridinium series—variant for which the linkage is cationic
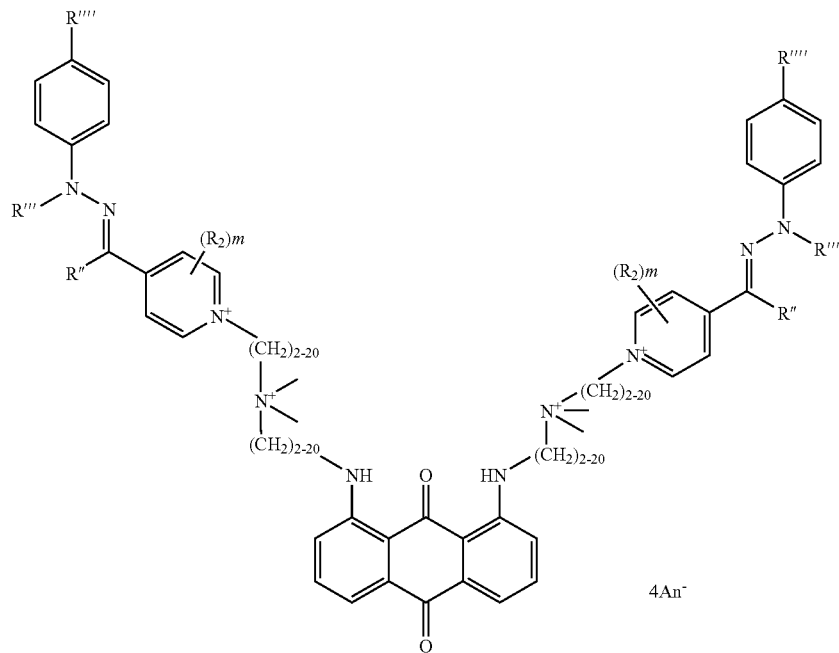
anthraquinones joined to a hydrazone chromophore in 4-pyridinium series—variant for which the linkage is cationic:
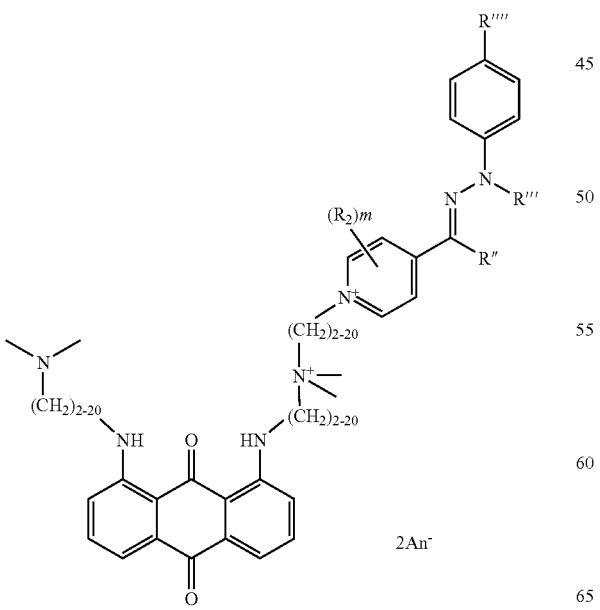

anthraquinones joined to a hydrazone chromophore in 4-quinolinium series—variant for which the linkage is cationic:

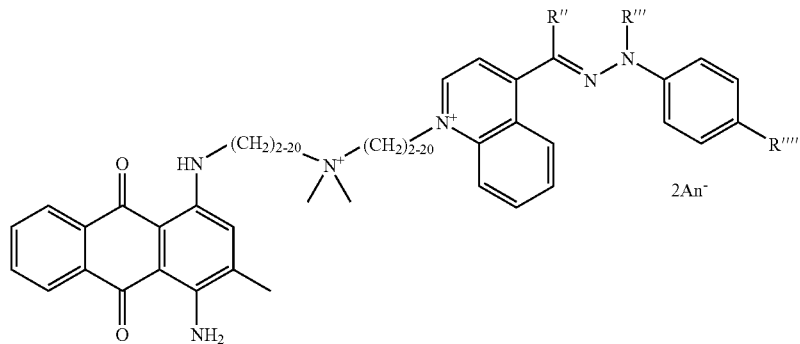

anthraquinones joined to a hydrazone chromophore in 4-pyridinium series—variant for which the linkage is cationic:

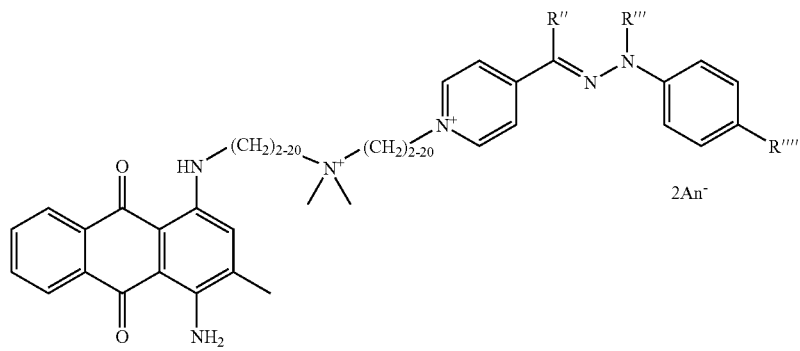

anthraquinones joined to an azo chromophore in azo-imidazolium series:

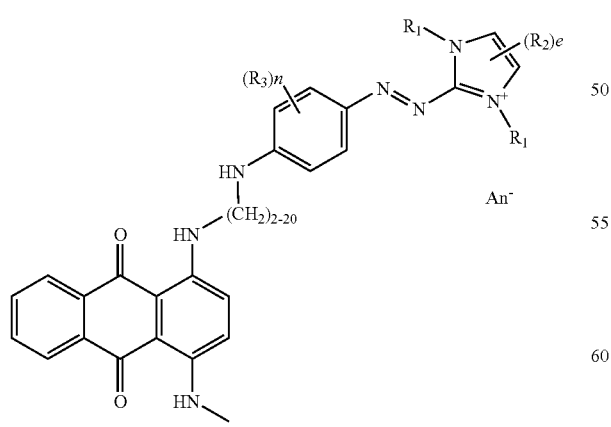

and the physiologically acceptable salts and solvates thereof.

In another embodiment, the mixed dyes that can be used in hair dyeing compositions in accordance with the present disclosure may be chosen from:

Anthraquinones joined to two azo chromophores in azo-imidazolium series:

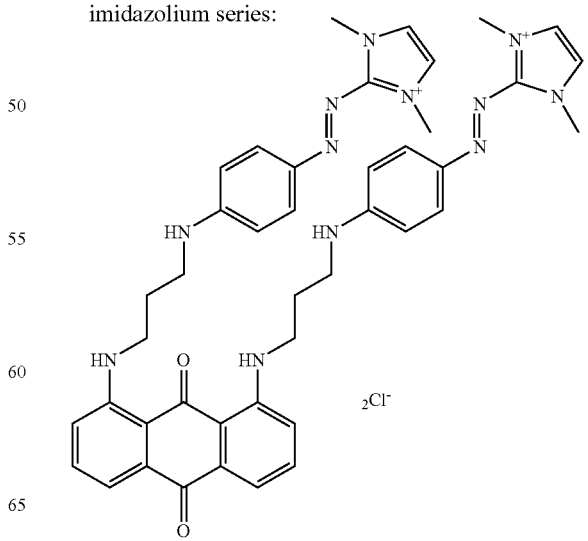

25
Anthraquinones joined to an azo chromophore in azo-imidazolium series:
26
Anthraquinones joined to two azo chromophores in 3-azo-pyridinium series:
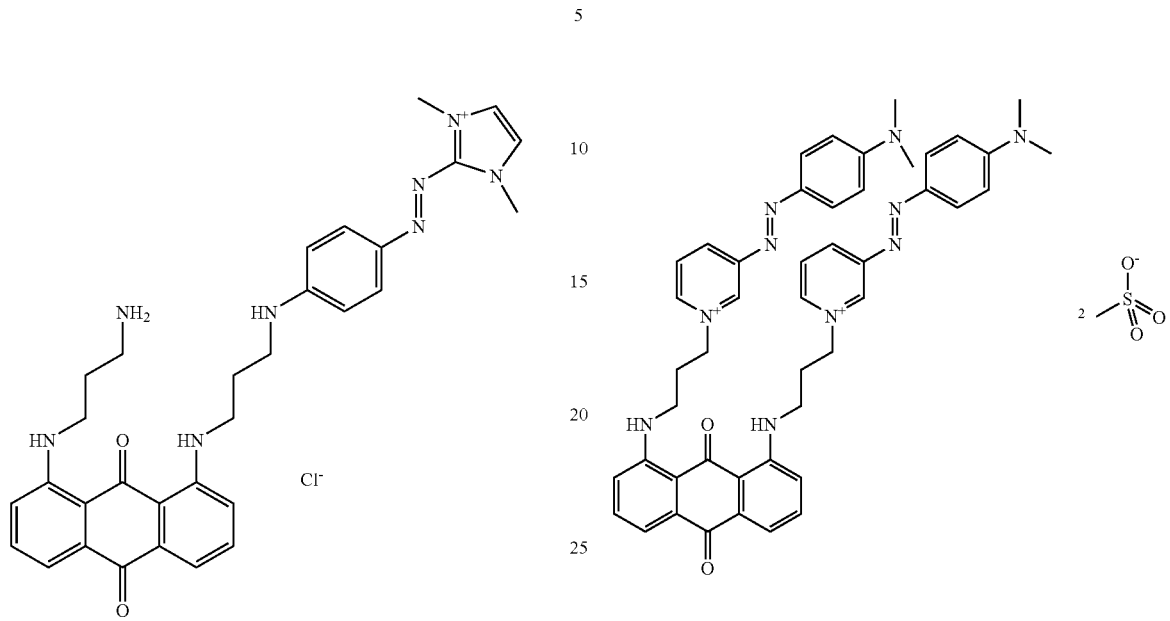
Anthraquinones joined to two azo chromophores in azo-imidazolium series:
Anthraquinones joined to two hydrazone chromophores in 4-pyridinium series:
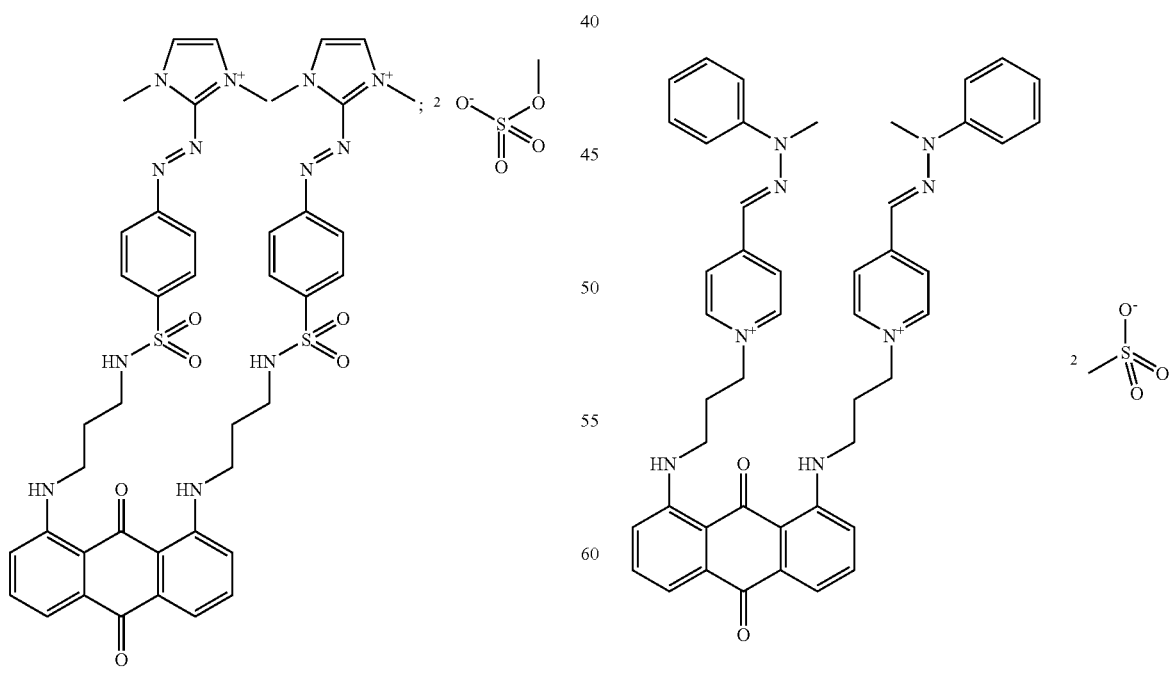

Anthraquinones joined to two hydrazone chromophores in 4-pyridinium series—variant for which the linkage is cationic
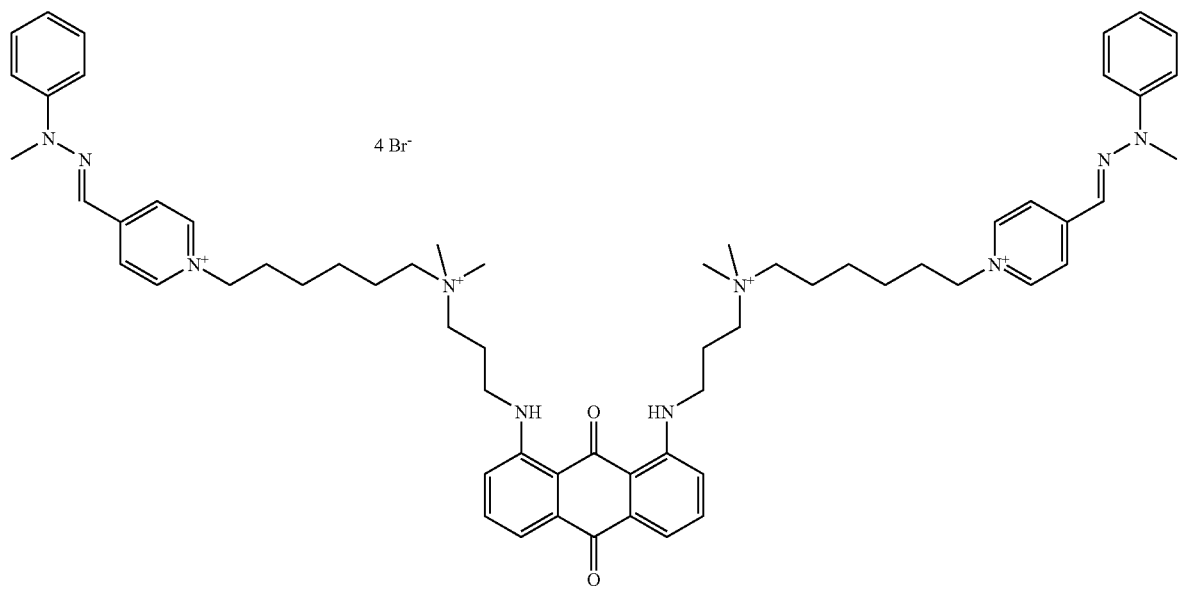
Anthraquinones joined to a hydrazone chromophore in 4-pyridinium series—variant for which the linkage is cationic
35
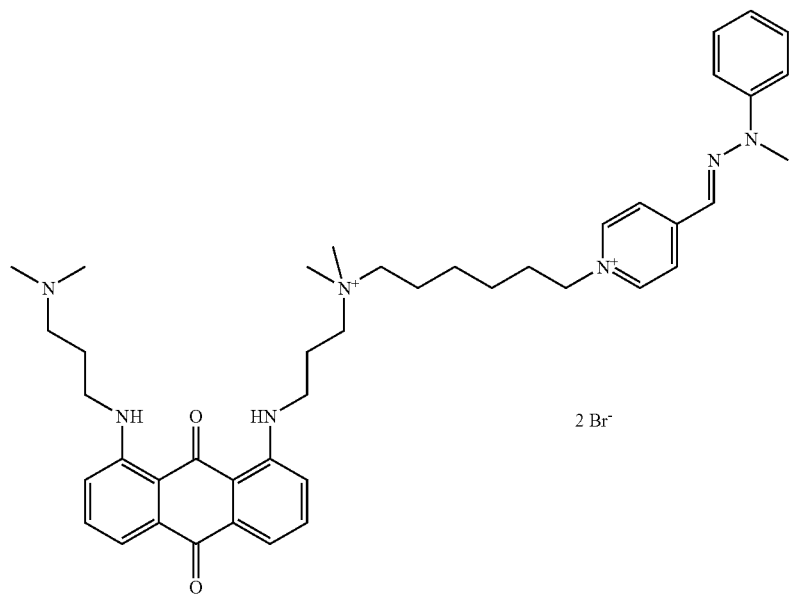

Anthraquinones joined to a hydrazone chromophore in 4-quinolinium series—variant for which the linkage is cationic:

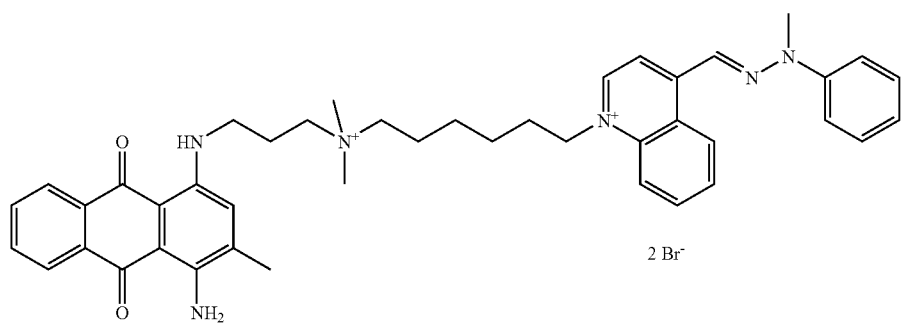

Anthraquinones joined to a hydrazone chromophore in 4-pyridinium series—variant for which the linkage is cationic:

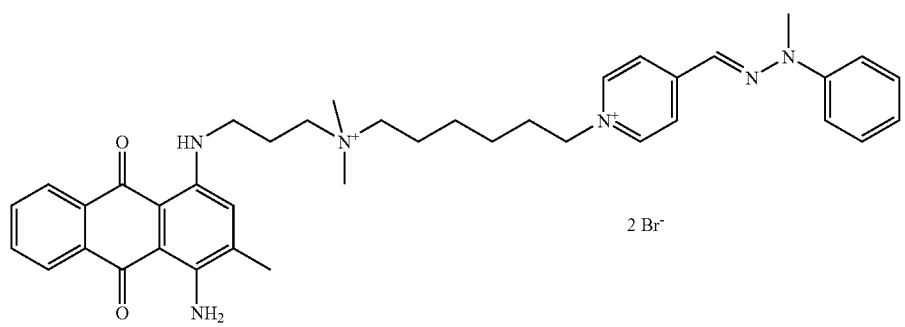

Anthraquinones joined to an azo chromophore in azo-imidazolium series:

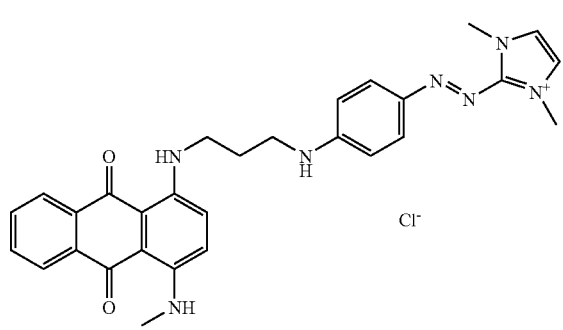

A great many methods of preparation generally known by a person skilled in the art may be used to obtain the compounds in accordance with the present disclosure, for example, the organic synthesis methods disclosed in *Advanced Organic Synthesis,* 5th edition, M. Smith and J. March, John Wiley & Sons Publ., 2001, *Color Chemistry,* 3rd edition, Wiley VCH Publ., 2003, H. Zollinger, *Color Chemistry,* Wiley VCH Publ., 2003, and *The Chemistry of Synthetic Dyes,* Academic Press, London, vol II, 1952.

Several general reactions may be used for the preparation of various molecules according to the present disclosure, including, but not limited to:
nucleophilic aromatic substitutions on molecules of the anthraquinone family,
nucleophilic substitutions by replacement of a leaving group,
The reactions may be chosen, for example, from:

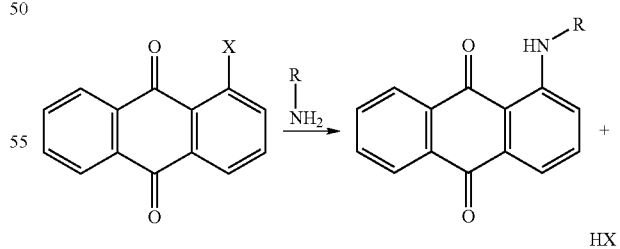

wherein X may be chosen, for example, from chloride and bromide (the substitution of a mesylate, of a tosylate, or of a fluoride also being possible).

The general reaction conditions may include bringing into contact with the amine, optionally introduced in excess of the stoichiometric ratio, at a ratio ranging, for example, from 1:1 to 100:1, and with the haloanthraquinone, without solvent or in the presence of a solvent, for instance, a polar solvent, such as DMF (N,N-dimethylformamide), DMPU (1,3-dimethyl-3,4,5,6-tetrahydro-2(1H)-pyrimidinone), and NMP (N-methylpyrrolidone), optionally in the presence of a base other than a primary or secondary amine, for example, triethylamine, pyridine, and calcium hydroxide, but also in the presence of catalysts such as the salts of transition metals, for example, copper(I) salts. The reaction time may range from 5 minutes to 5 days, for example, from 1 hour to 24 hours. The reaction temperature may range from room temperature to 200° C., for example, ranging from 60° C. to 130° C.

This type of reaction is described, for example, in Dyes and Pigments, 1981, p 125-132.

This reaction may be useful within the scope of the present disclosure and will be described in more detail later, in three examples of preparation of products.

nucleophilic substitutions by displacement of hydroxyl,

The displacement of one or both hydroxyl groups in alizarin by an amine is known and can be used for obtaining anthraquinones bis-aminated at 1,4 at lower cost, which are useful for the purpose of the present disclosure. The reaction conditions are described, for example, in *The Chemistry of Synthetic Dyes*, Academic Press, London, vol II, 1952.

The general reaction scheme is:

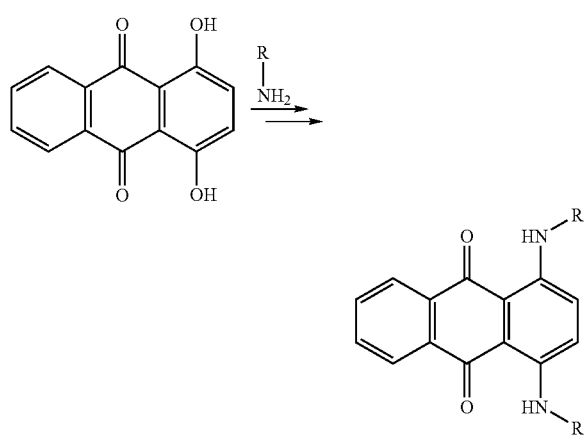

The two aforementioned reactions may be suitable for preparation of the products according to the present disclosure, including finished products (in which case R will have the chromophore of the cationic azo family or cationic hydrazone family or the group R' or R'-L$_2$), and synthetic intermediates, which may be precursors of interest for at least one products according to the present disclosure.

reactions of nucleophilic aromatic substitution on a cationic azo dye,

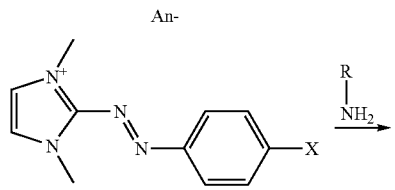

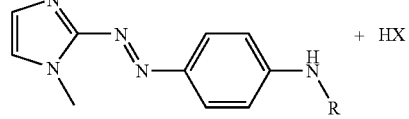

wherein X may be chosen, for example, from F, Cl, and OMe.

This reaction may be useful within the scope of the present disclosure as it permits simple joining of an azo chromophore to a linkage. More details will be given later, in the form of an example of application. The reaction may be carried out in solution, for example, in a polar solvent, such as alcohols and formamides, at a temperature ranging from 0° C. to 160° C., for example, from 40° C. to 120° C., the reaction being carried out for a time period ranging from 5 min to 5 days, for instance, from 1 h to 48 h.

This type of reaction is described, for example, in Dyes & Pigment, 31(3), 1996, p. 219-224 and U.S. Pat. No. 5,708,151.

reaction of diazotization for the preparation of an azo chromophore,

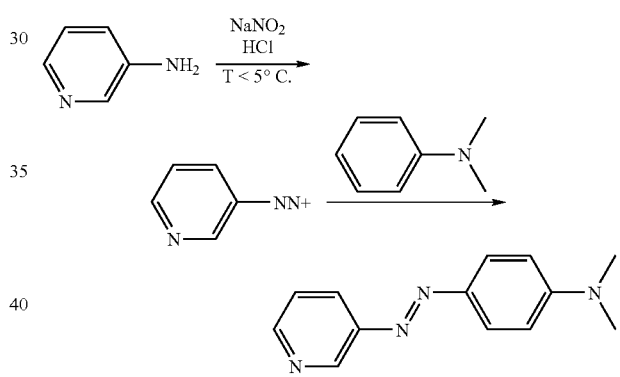

This reaction is a classical reaction used for the preparation of cationic azo compounds. One variant of this reaction comprises the use of aminopyridine oxides as protected forms of aminopyridines, and may be useful for the preparation of azo compounds in 2-azopyridinium series. A second variant comprises the intermediate formation of a diazonium salt from a primary aniline then condensing a heterocycle on this salt, as shown in the following scheme:

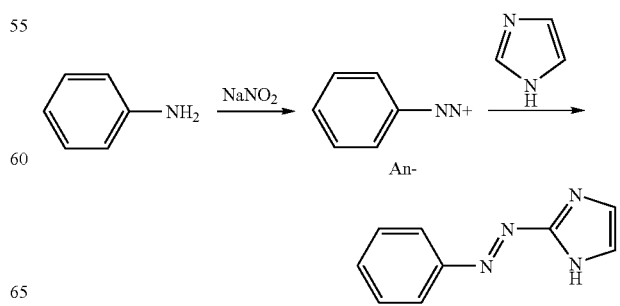

This reaction may also be useful in the present disclosure, as will be explained later and described in an example according to the present disclosure. Moreover, this reaction is also described in the publications disclosed herein and in numerous patents describing cationic azo dyes.

reaction of nucleophilic aromatic substitution with a hydrazine, followed by oxidation for the preparation of an azo chromophore,

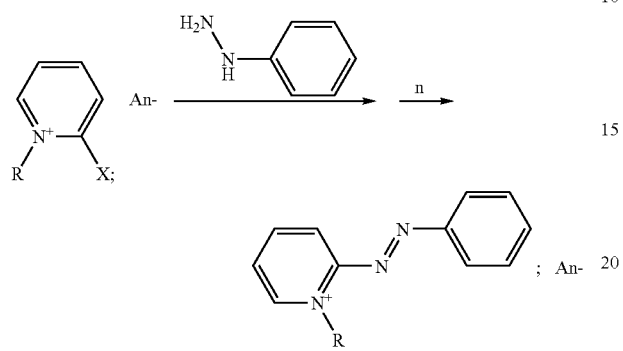

wherein X is chosen, for example, from Cl, Br, F, and OAlkyl.

This is an alternative method to the first two, which may be useful when the compounds used for this route are more easily accessible or alternatively in the case when the diazonium salts required for the methods described previously are unstable and unsuitable for preparation of the desired products.

condensation of a hydrazine on a carbonylated derivative for the preparation of a hydrazone chromophore,

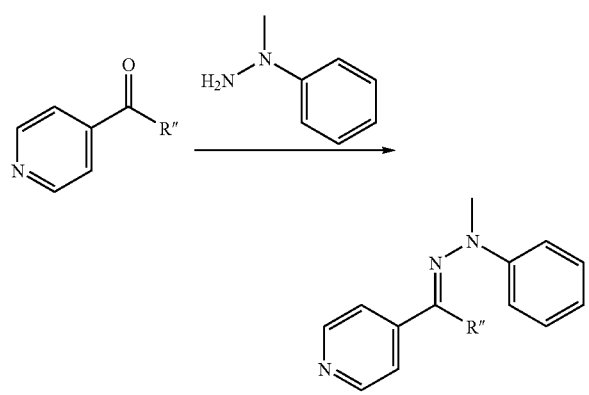

This reaction may be useful for the preparation of dyes of the hydrazone family, and may be useful in the present disclosure for the formation of these chromophores, generally when the latter are not commercially available.

This reaction may be carried out with very good yields in polar solvents such as alcohols, and, in at least one embodiment, in the presence of an acid reactant, such as carboxylic acids. The reaction may be carried out at a temperature ranging from 0° C. to 100° C., for example, from 10° C. to 80° C. The reaction time may range from 1 min to 48 h, for instance, from 5 min to 24 h.

This type of reaction is described, for example, in International Patent Application Publication No. WO 03/060015.

nucleophilic substitution of an amine on a sulphonyl halide

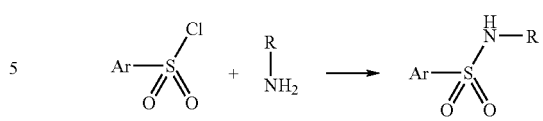

This reaction enables two groups to be joined together; and may be utilized within the scope of the present disclosure for joining the linkage $L_1$, for example, to a chromophore or to a chromophore precursor; which will be explained later in an example.

alkylation of a heteroaromatic ring by an alkyl halide or by a sulphonic ester (dialkyl sulphate, alkyl sulphonate),

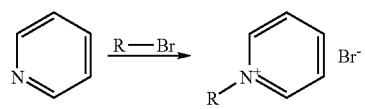

This reaction may permit the quaternization of azo or hydrazone groups, and the use of the heteroatoms of rings A as the anchoring point for the linkages $L_1$. It also may serve for quaternization of groups $L_1$ in the case when the latter are cationic, and finally, it may permit the introduction of an additional cationic function, for example, on a group R'.

This type of reaction is described, for example, in International Patent Application Publication No. WO 03/060015.

The sequences of reactions for obtaining these products are illustrated by the synthesis schemes shown below. Further details will be given for certain examples, for purposes of illustration.

Scheme 1

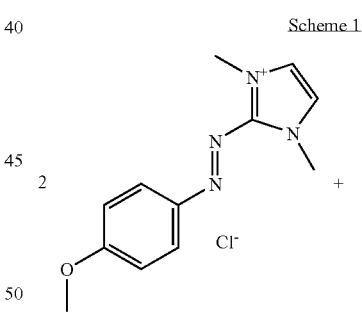

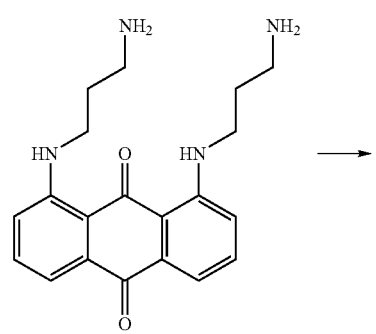

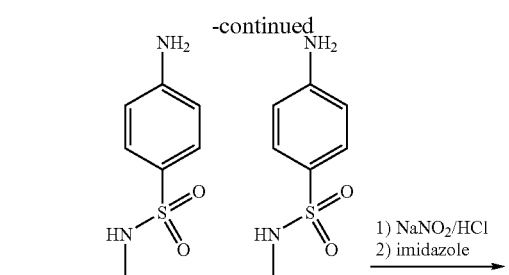
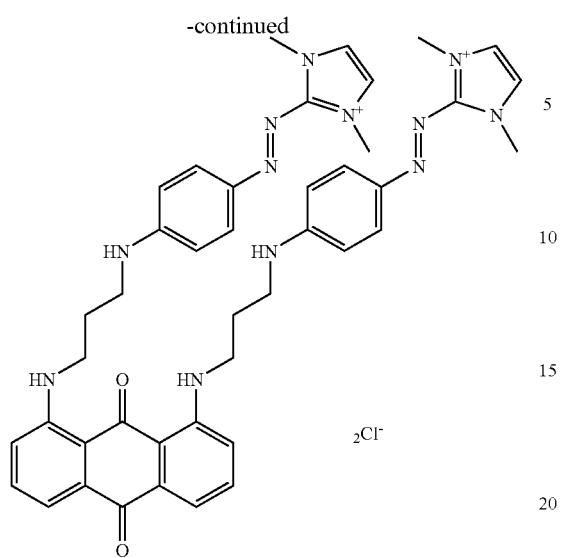
Scheme 2
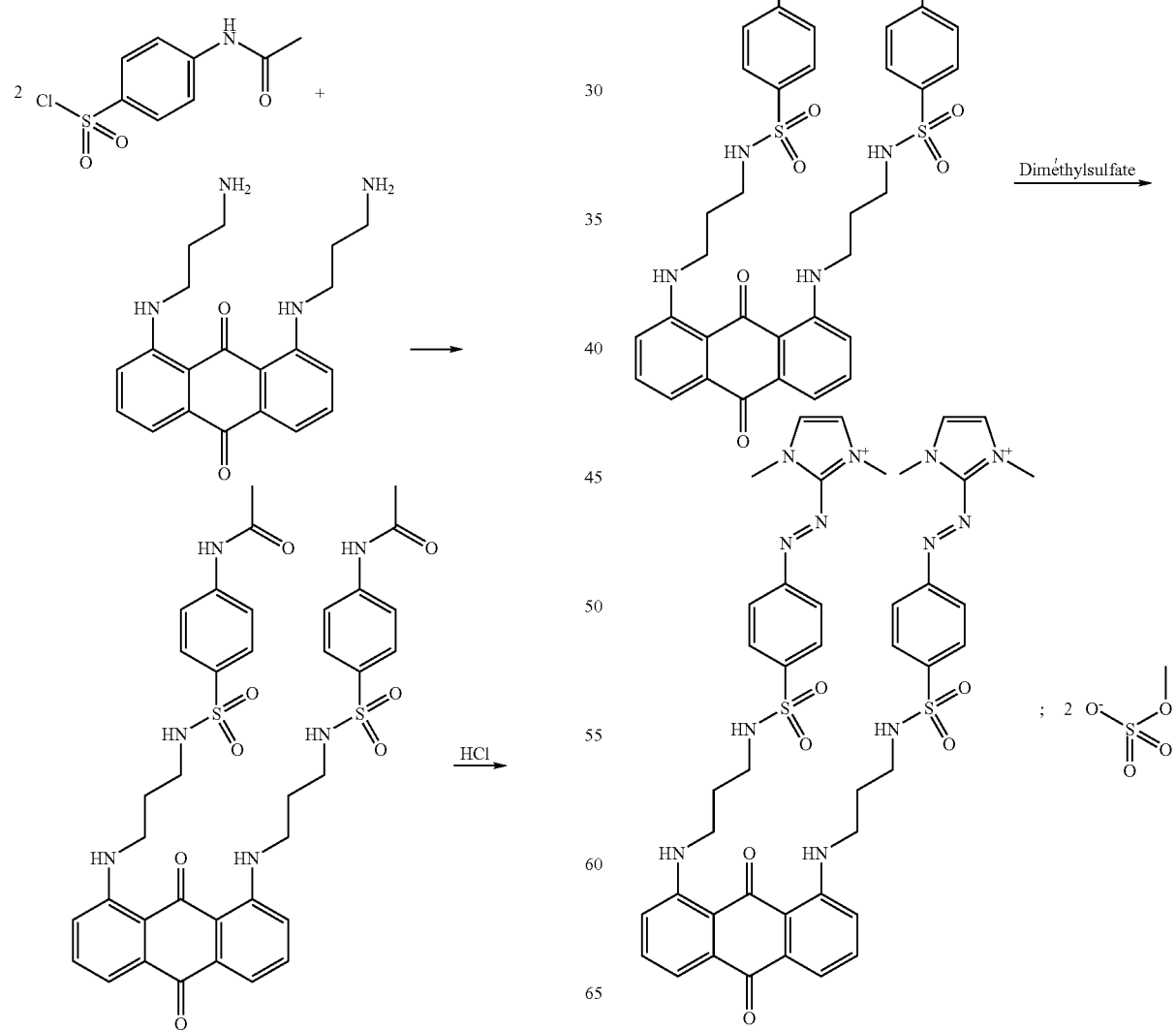

This synthesis strategy is an alternative to the method described previously and may be useful when there is no labile group on the azo dye for attachment.
Scheme 3
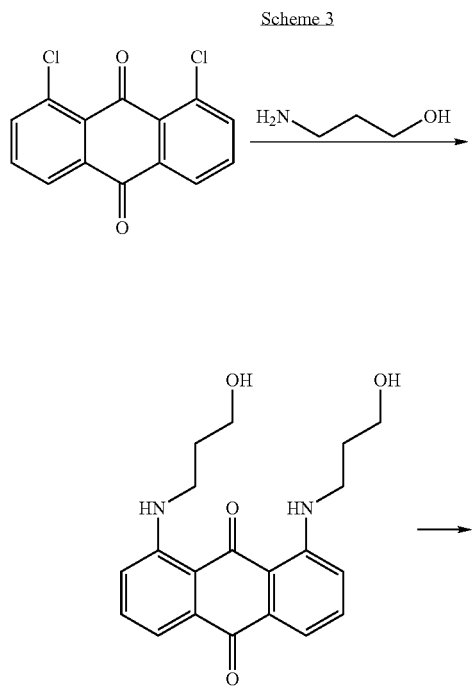
-continued
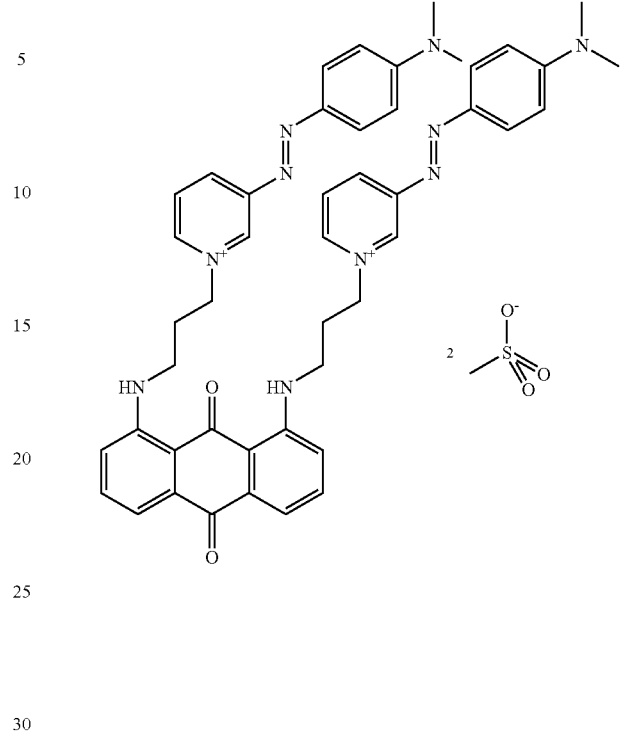
Scheme 4
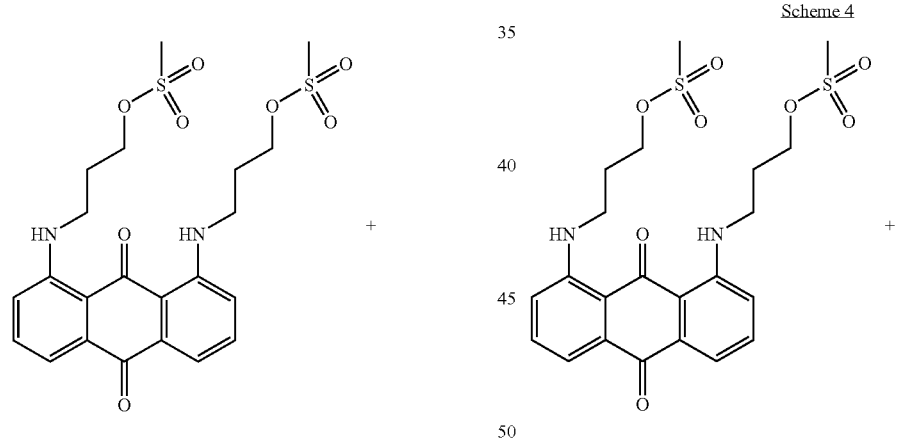
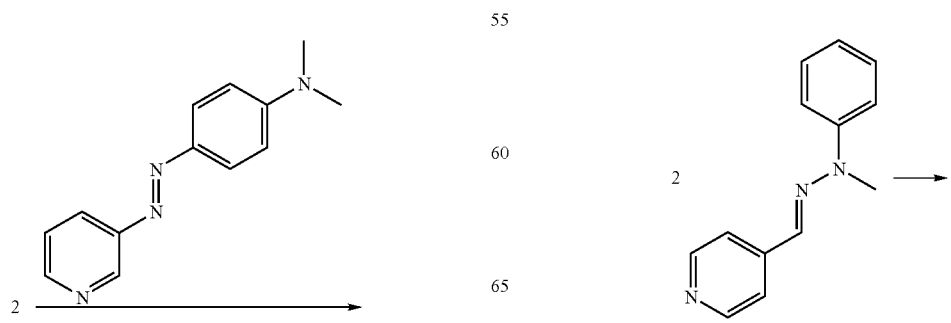

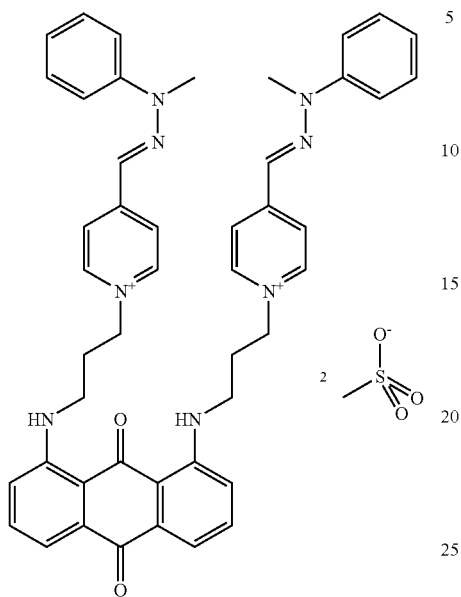
Scheme 5
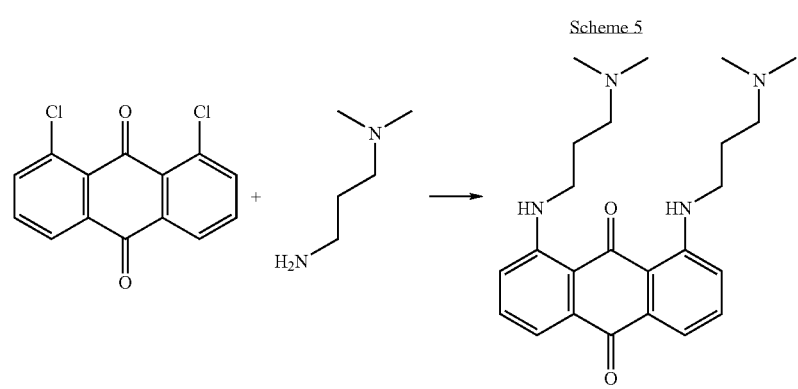
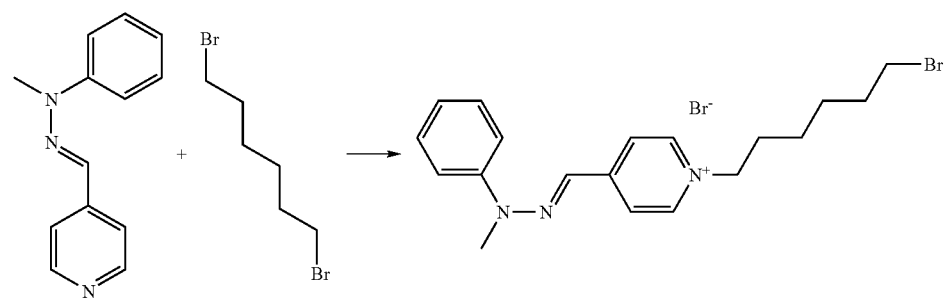

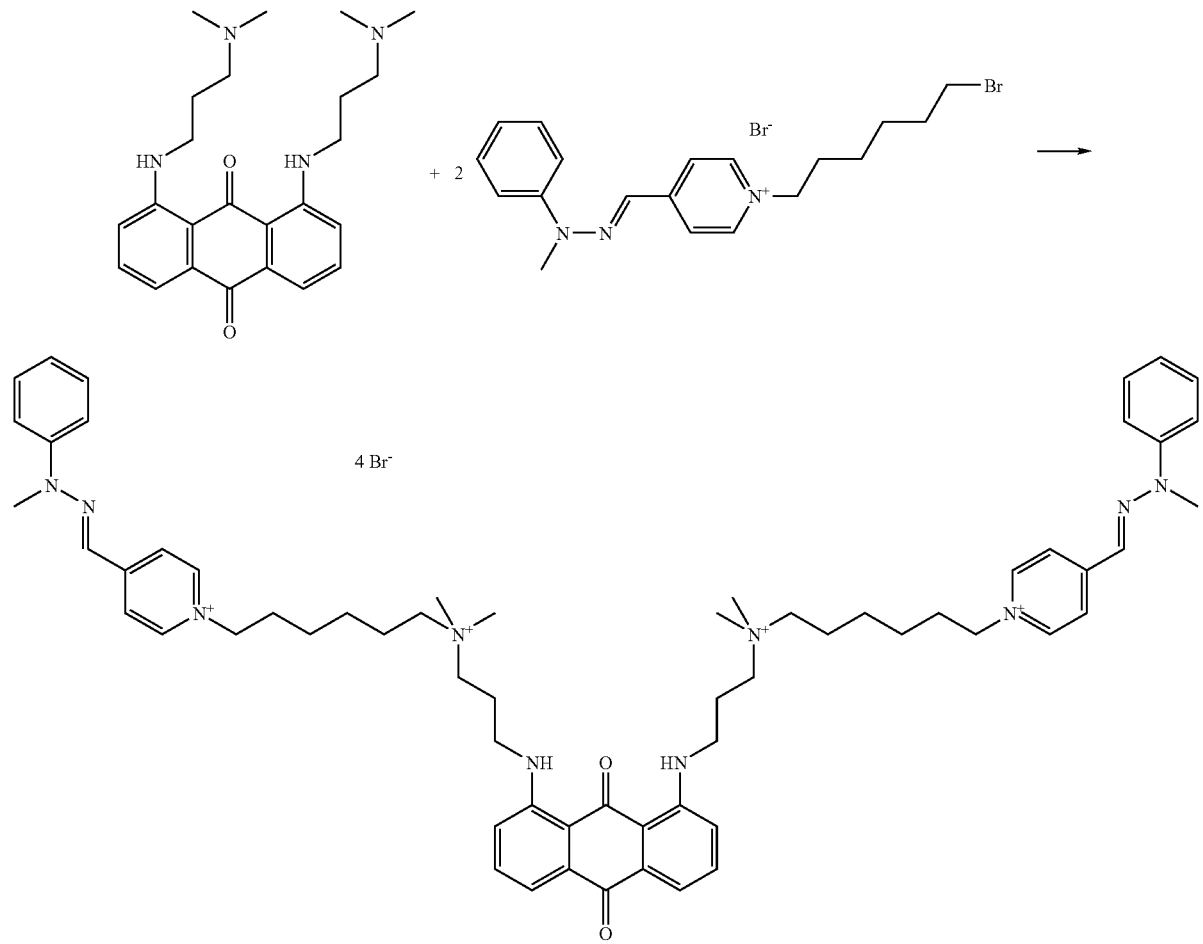
Scheme 6
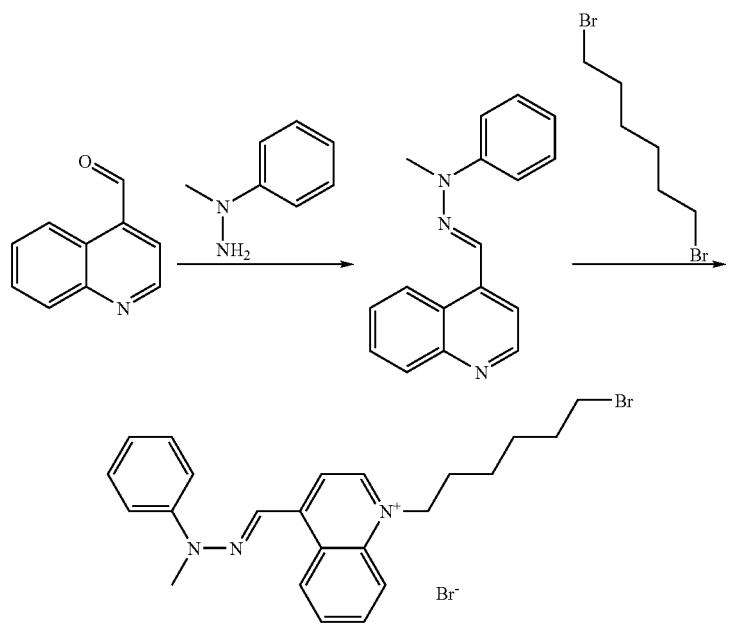

-continued
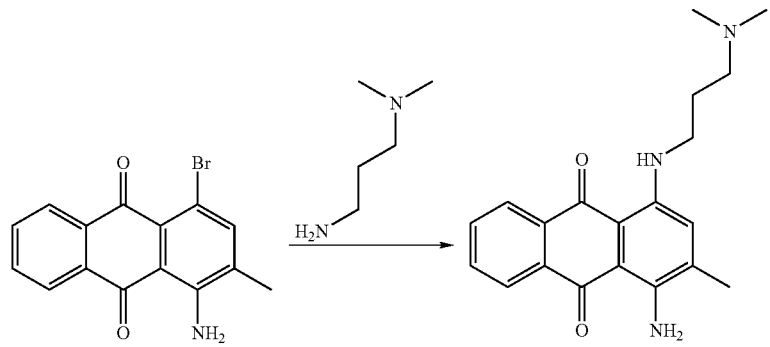
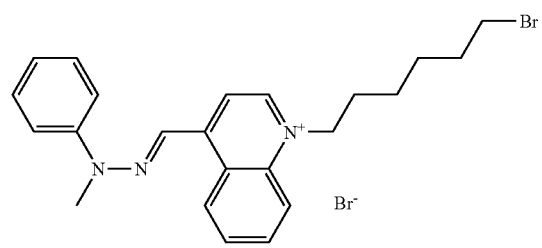
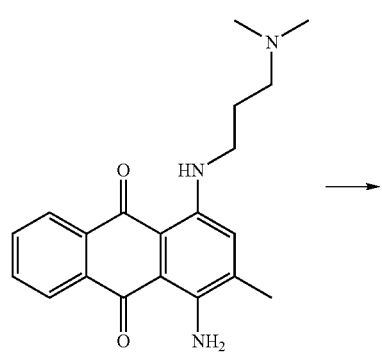
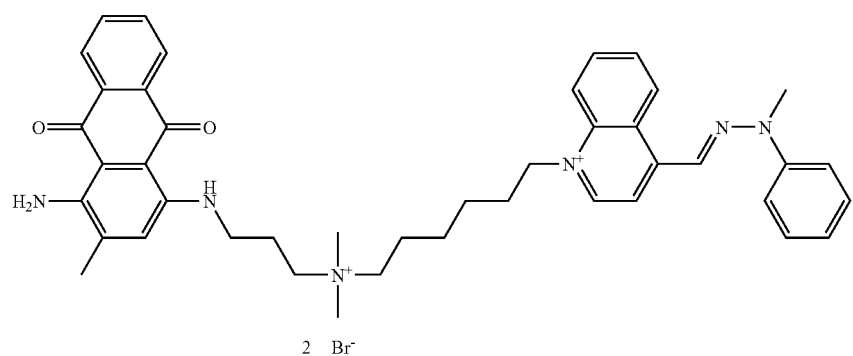

Scheme 7
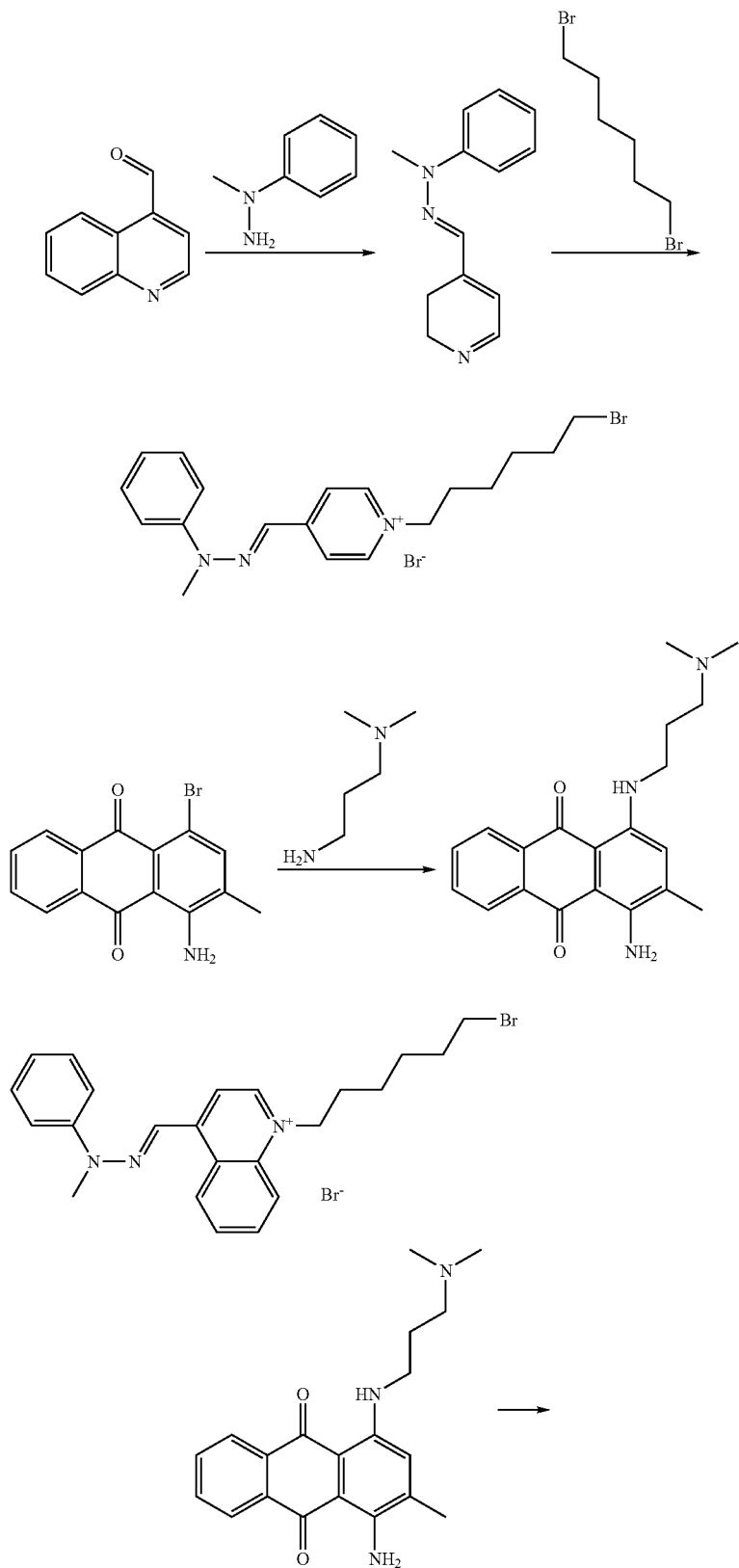

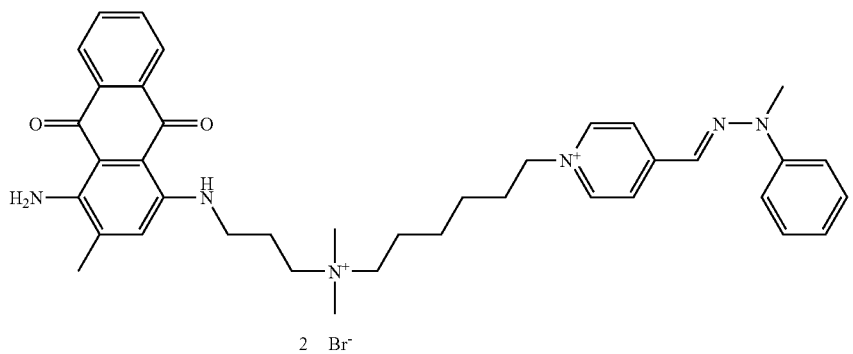

Also disclosed herein is a composition for the oxidation dyeing of keratin fibers, for example, human keratin fibers such as the hair, comprising, in a medium suitable for dyeing, at least one mixed dye as defined herein.

The at least one mixed dye chosen from compounds of formula (Ia) and (Ib) and their salts and solvates may be present in the dyeing composition in an amount ranging from 0.001 to 20 wt. %, for example, from 0.005 to 10 wt. %, or from 0.01 to 5 wt. %, relative to the total weight of the dyeing composition.

The dyeing composition according to the present disclosure may further comprise at least one additional direct dye different from the mixed dye of the present disclosure.

According to at least one embodiment, the additional direct dye may be chosen from the direct dyes traditionally employed in the area of the dyeing of keratin fibers, for example, human keratin fibers, for example, nitro dyes of the benzene series, the additional direct azo dyes, and direct methine dyes. These direct dyes may be chosen from non-ionic, anionic, and cationic dyes. In at least one embodiment, these additional direct dyes are cationic.

The at least one additional direct dye may be present in the dyeing composition in an amount, for each of them, ranging from 0.001 to 10 wt. % relative to the total weight of the dyeing composition.

The dyeing composition of the present disclosure may further comprise at least one oxidation base and/or at least one coupling agent, conventionally used for the dyeing of keratin fibers, for example, human keratin fibers.

Examples of suitable oxidation bases include, but are not limited to, para-phenylenediamines, bis-phenylalkylenediamines, para-aminophenols, bis-para-aminophenols, ortho-aminophenols, heterocyclic bases, and their addition salts.

The at least one oxidation base may be present in the dyeing composition in an amount ranging from 0.001 to 10 wt. % relative to the total weight of the dyeing composition, for example, from 0.005 to 6 wt. %.

Non-limiting examples of coupling agents include meta-phenylenediamines, meta-aminophenols, meta-diphenols, naphthalenic coupling agents, heterocyclic coupling agents, and their addition salts.

The at least one coupling agent may be present in the dyeing composition in an amount ranging from 0.001 to 10 wt. % relative to the total weight of the dyeing composition, for example, from 0.005 to 6 wt. %.

The addition salts of the oxidation bases and of the coupling agents that are useful within the scope of the present disclosure, may include, for example, the acid addition salts, such as hydrochlorides, hydrobromides, sulphates, citrates, succinates, tartrates, lactates, tosylates, benzenesulphonates, phosphates, and acetates and base addition salts such as soda, potash, ammonia, amines, and alkanolamines.

The medium suitable for dyeing, also called the dyeing support, is a cosmetic medium chosen, for example, from water and mixtures of water and at least one organic solvent for dissolving the compounds that would not be sufficiently soluble in water.

Examples of suitable organic solvents include, but are not limited to, linear or branched monoalcohols, optionally saturated, comprising from 2 to 10 carbon atoms, such as ethanol, isopropanol; aromatic alcohols such as benzyl alcohol, phenylethyl alcohol; polyols and ethers of polyols such as monomethyl, monoethyl, and monobutyl ethers of ethyleneglycol, propyleneglycol, and its ethers such as, for example, monomethylether of propyleneglycol, butyleneglycol, dipropyleneglycol, hexyleneglycol (2-methyl 2,4-pentanediol), neopentylglycol, and 3-methyl-1,5-pentanediol; and alkylethers of diethyleneglycol, for example, $C_1$-$C_4$ alkyl ethers, such as monoethylether and monobutylether of diethyleneglycol; and mixtures thereof.

The at least one solvent may be present in the dyeing composition in an amount ranging from 1 to 40 wt. % relative to the total weight of the dyeing composition, for example, from 5 to 30 wt. %.

The dyeing composition according to the present disclosure may further comprise at least one additive conventionally used in compositions for the dyeing of keratin fibers, for example, human keratin fibers such as the hair, such as anionic, cationic, non-ionic, and amphoteric zwitterionic surfactants and mixtures thereof; anionic, cationic, non-ionic, amphoteric, and zwifterionic polymers and mixtures thereof; mineral and organic thickening agents, for example, anionic, cationic, non-ionic, and amphoteric associative thickening agents; antioxidizing agents; penetrating agents; sequestering agents; perfumes; buffers; dispersants; conditioners such as volatile or non-volatile, modified or unmodified silicones; film-forming agents; ceramides and pseudo-ceramides; preservatives; opacifiers; and the like.

The at least one additive may be present in the dyeing composition in an amount, for each of them, ranging from 0.01 to 20 wt. % relative to the total weight of the dyeing composition.

The composition of the present disclosure may further comprise at least one oxidizing agent.

The oxidizing agents traditionally used for the oxidation dyeing of keratin fibers, for instance, human keratin fibers, include, but are not limited to, hydrogen peroxide, urea peroxide, bromates and ferricyanides of alkali metals, persalts such as perborates and persulphates of alkali metals and alkaline-earth metals, such as sodium, potassium, magnesium, and mixtures thereof, peracids and oxidase enzymes, for example, peroxidases, 2-electron oxido-reductases such as uricases, and 4-electron oxygenases such as laccases. In one embodiment, the at least one oxidizing agent is hydrogen peroxide.

The composition of the present disclosure may further comprise at least one alkaline agent which may be chosen from those conventionally used in the cosmetics industry, for example, ammonia, alkaline carbonates, alkanolamines such as the mono-, di-, and triethanolamines and their derivatives, the hydroxides of sodium and potassium and the compounds of formula (A):

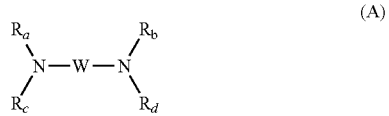

(A)

wherein
W is chosen from propylene residues optionally substituted with at least one entity chosen from hydroxyl groups and $C_1$-$C_4$ alkyl radicals; and
$R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

The pH of the dyeing composition of the present disclosure may range, for example, from 8 to 11.

It is to be understood that a person skilled in the art will ensure that the at least one additional compound is chosen such that the advantageous properties intrinsic to the composition according to the present disclosure will not be adversely affected, or not substantially so, by any addition envisaged.

The dyeing composition according to the present disclosure may be in various forms, such as liquids, creams, and gels, or in any other suitable form for carrying out the dyeing of keratin fibers, for example, human keratin fibers, such as the hair.

Also disclosed herein is a method for dyeing keratin fibers comprising applying a composition of the present disclosure to the fibers, which may be wet or dry.

In at least one embodiment, the method of dyeing comprises:
applying at least one composition comprising at least one mixed dye is applied to fibers, which may be wet or dry, optionally in the presence of at least one oxidizing agent,
leaving the composition on the fibers for a sufficient time to obtain the desired coloration,
optionally rinsing the fibers,
washing and rinsing the fibers, and
drying the fibers or leaving the fibers to dry.

According to one embodiment, the composition applied to the keratin fibers does not comprise an oxidizing agent. This method may be used, for example, when the dyeing composition comprises at least one mixed dye according to the present disclosure and optionally at least one additional direct dye.

According to another embodiment, the method may be carried out with at least one oxidizing agent. This method may be suitable regardless of the nature of the dyes present (mixed dye, additional direct dye, oxidation bases and/or coupling agents). Such a method can provide lightening of the treated fiber.

According to this embodiment, the at least one oxidizing agent may be added to the dyeing composition at the moment of use, or alternatively, it may be applied in an oxidizing composition comprising it, applied simultaneously with or sequentially to the dyeing composition comprising the at least one mixed dye. In the latter case, the oxidizing agent is present in a composition different from that comprising the at least one mixed dye.

According to yet another embodiment, the composition comprising the at least one mixed dye is mixed, for example, at the moment of use, with a composition comprising, in a medium suitable for dyeing, at least one oxidizing agent, this oxidizing agent being present in a sufficient amount to obtain the desired lightening. The mixture obtained may then be applied to the keratin fibers.

After a sufficient waiting time for obtaining the desired coloration, ranging, for example, from 3 to 50 minutes, or from 5 to 30 minutes, the keratin fibers may be rinsed, washed with shampoo, rinsed again, and dried or left to dry.

In at least one embodiment, the composition may be applied and left to act at a temperature ranging from 15 to 80° C., for example, from 15 to 40° C.

The oxidizing composition may also comprise at least one of various additives conventionally used in compositions for dyeing keratin fibers, for example, human keratin fibers, and as defined above.

In another embodiment, the pH of the oxidizing composition comprising the oxidizing agent is such that after mixing with the dyeing composition, the pH of the resulting composition applied to the keratin fibers (i.e., the ready-to-use composition) ranges, for example, from 7 to 12, for example, from 8 to 11. The pH may be adjusted to the desired value by means of at least one agent chosen from acidifying agents and alkalizing agents.

Examples of acidifying agents include, but are not limited to, mineral and organic acids such as hydrochloric acid, orthophosphoric acid, sulphuric acid, and acetic acid.

Suitable alkalizing compounds may be chosen from the previously provide herein.

The ready-to-use composition, i.e., the composition which is finally applied to the keratin fibers, may be in various forms, such as liquids, creams, and gels, or in any other form suitable for dyeing keratin fibers, for example, human keratin fibers, such as the hair.

Further disclosed herein is a device (kit) comprising at least one compartment, wherein at least one first compartment contains at least one dyeing composition comprising at least one mixed dye in accordance with the present disclosure, optionally at least one direct dye different from the mixed dye, optionally at least one oxidation base, and optionally at least one coupling agent, and at least one second compartment comprises at least one oxidizing agent.

In at least one embodiment, the at least one mixed dye, optionally the at least one additional direct dye, optionally the at least one oxidation base, and optionally the at least one coupling agent may be in the same compartment or in several compartments; wherein one compartment may contain a single type of dye (for example, mixed dyes, additional direct dyes, and oxidation dyes) or a combination of several of them.

This kit may be equipped with means for supplying the desired mixture onto the fibers to be treated, such as the kits described in French Patent No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Synthesis Examples

Example 1

Anthraquinone Joined to Two Azo Chromophores in Azo-imidazolium Series—Dye

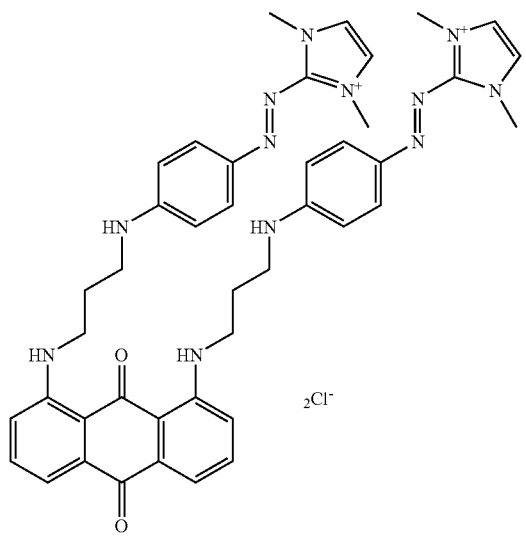

Route of Synthesis

First stage: preparation of 1,8-bis[(3-aminopropyl)amino]anthra-9,10-quinone

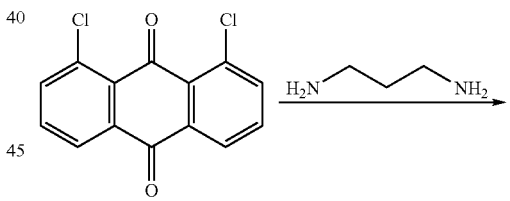

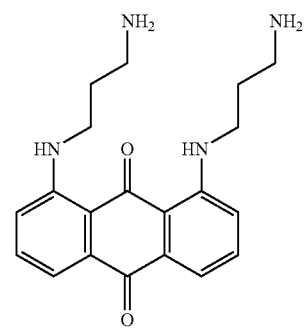

A mixture of 1,8-dichloroanthra-9,10-quinone and an excess of 1,3-propanediamine was stirred and heated at 90° C. for 24 hours. It was cooled and then poured into isopropyl ether. The solution obtained was washed with dilute soda solution, dried over sodium sulphate, and concentrated under vacuum. The violet product obtained in the form of paste was purified by chromatography on silica gel (ethyl acetate, ethanol, and triethylamine). A violet powder was collected. The results of analysis were consistent with the structure of 1,8-bis[(3-aminopropyl)amino]anthra-9,10-quinone.

Second stage: double substitution of an MeO group on 2-[(4-methoxyphenyl)diazenyl]-1,3-dimethyl-1H-imidazol-3-ium chloride by the amino group of 1,8-bis[(3-aminopropyl)amino]anthra-9,10-quinone:

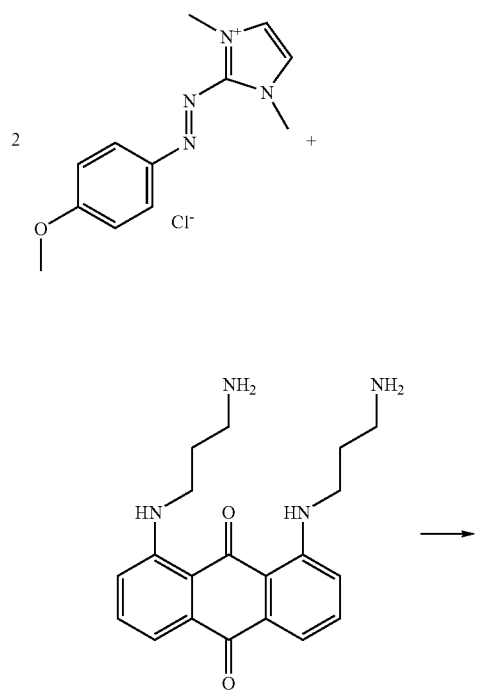

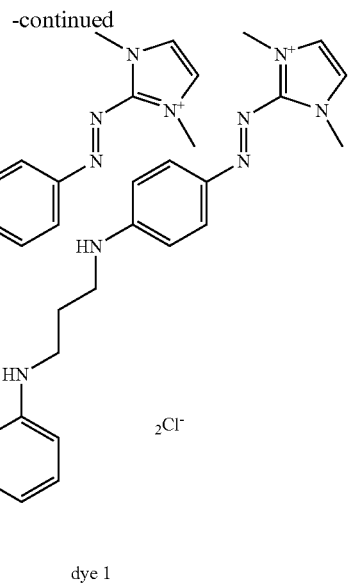

dye 1

1.89 g of 2-[(4-methoxyphenyl)diazenyl]-1,3-dimethyl-1H-imidazol-3-ium chloride and 1,8-bis[(3-aminopropyl)amino]anthra-9,10-quinone (stoichiometric ratio of two to one) were mixed together in solution in a mixture of pentanol (7 mL) and dichloromethane (70 mL), the mixture thus obtained was heated at 80° C. (the dichloromethane was gradually distilled) for 24 hours, then precipitated after cooling by further addition of dichloromethane (800 mL). After draining, rinsing with dichloromethane and drying, 1.3 g of reddish brown powder was collected. The results of analysis were consistent with the structure of the expected product (dye 1).

Example 2

Anthraquinone Dye Bound to Two Hydrazone Chromophores in 4-pyridinium Series—Variant in which the Linkage is Cationic—Dye 2

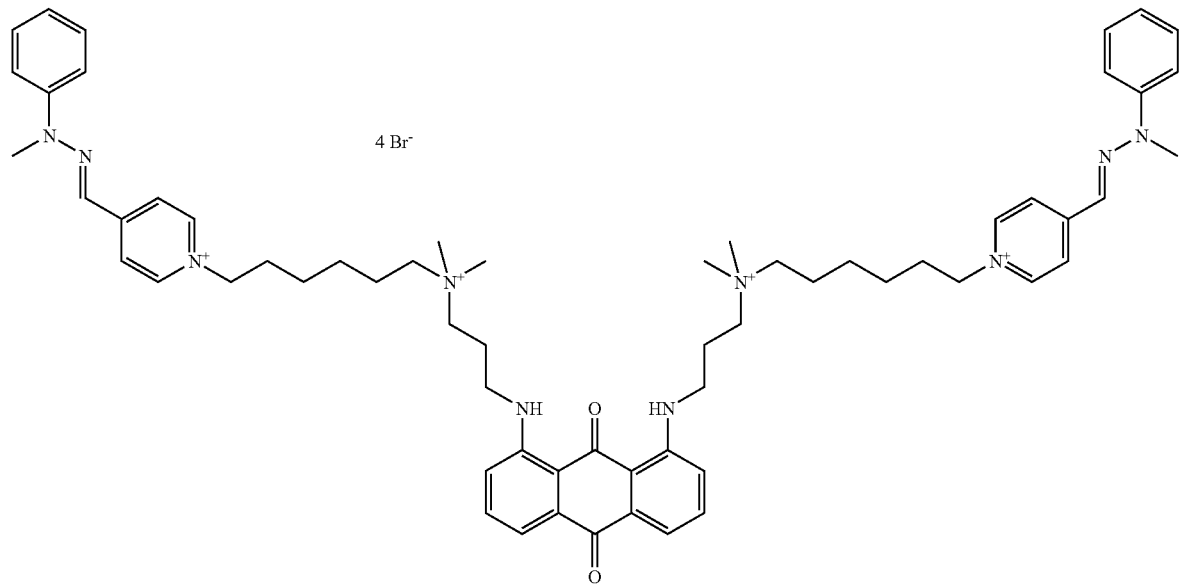

First stage: preparation of 1,8-bis[(3-dimethylaminopropyl)amino]anthra-9,10-quinone Second stage: formation of 1-(6-bromohexyl)-4-{(E)-[methyl(phenyl)hydrazono]methyl}pyridinium bromide

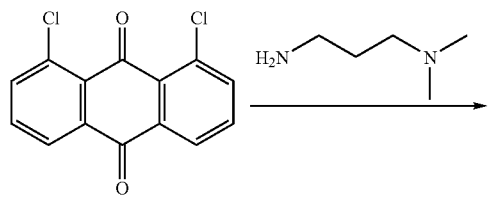

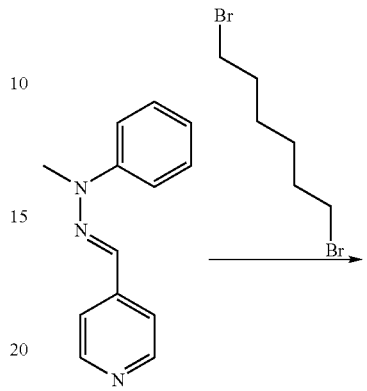

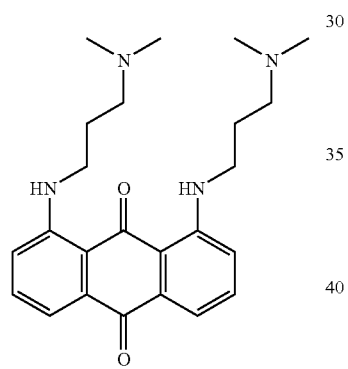

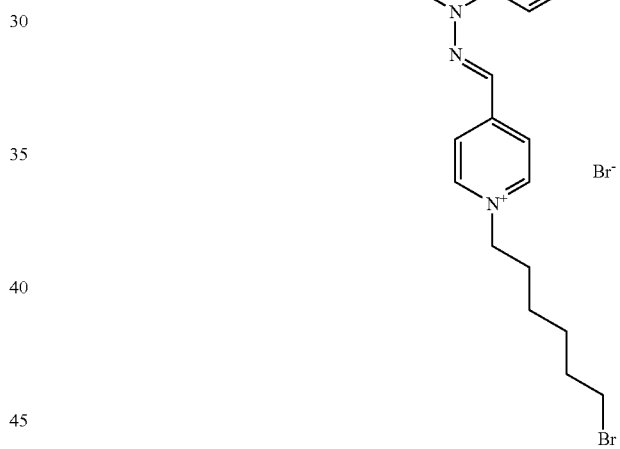

A mixture of 25 g of 1,8-dichloroanthra-9,10-quinone and 150 g of N,N-dimethylamino-1,3-propylenediamine was stirred and heated at 90° C. for 24 hours. It was cooled then poured into 1 L of isopropyl ether. The solution obtained was washed with dilute soda solution, dried over sodium sulphate, and concentrated under vacuum. The violet product obtained in the form of paste (31 g) was purified by chromatography on silica gel (ethyl acetate, ethanol, and triethylamine) then crystallization in petroleum ether. 23.5 g of violet crystals were collected. The results of analysis were consistent with the structure of 1,8-bis[(3-dimethylaminopropyl)amino]anthra-9,10-quinone.

Methyl(phenyl)hydrazone of isonicotinaldehyde (80.1 g) was dissolved in 250 mL of toluene. The mixture was heated to 80° C., then a solution of 1,6-dibromohexane (473 g) in 750 mL of toluene was added in 10 minutes. After 4.5 hours the reaction mixture was cooled, then filtered. The precipitate obtained was washed with 200 mL of toluene then 100 mL of petroleum ether. It was dissolved in 1 L of dichloromethane then extracted with water. The organic phase was washed 4 times with water, dried over magnesium sulphate, filtered, then concentrated. A brown oil was obtained, which was taken up in 50 mL of toluene. A yellow precipitate was obtained, which was separated by filtration, then dried to give 95.1 g of the expected product in the form of a yellow powder.

Analyses showed that it corresponded to the expected compound (1-(6-bromohexyl)-4-{(E)-[methyl(phenyl)hydrazono]methyl}pyridinium bromide).

Third stage: reaction between the two compounds prepared according to the previous two stages

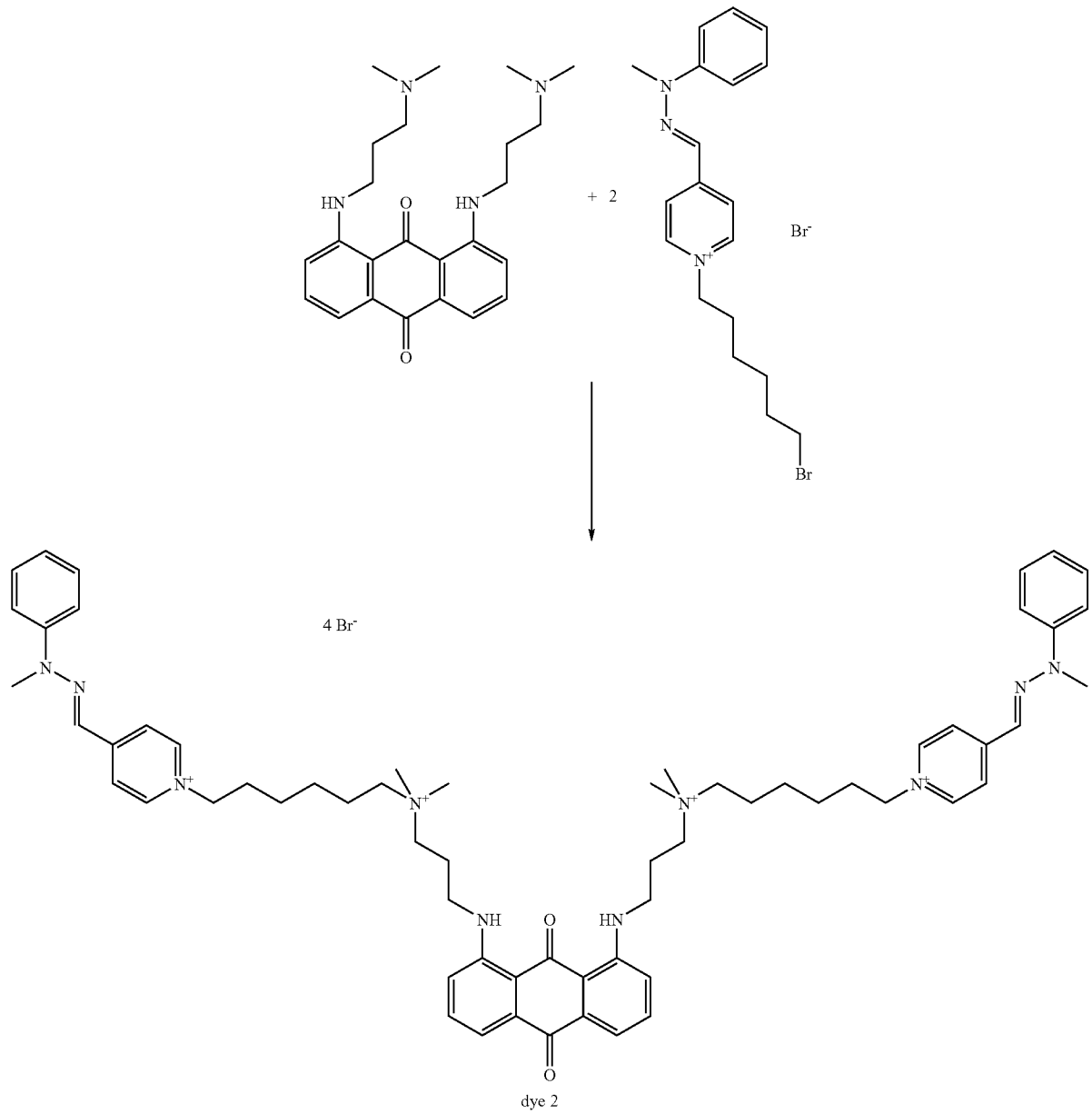

dye 2

1-(6-Bromohexyl)-4-{(E)-[methyl(phenyl)hydrazono]methyl}pyridinium bromide (28.78 g) and 1,8-bis[(3-dimethylaminopropyl)amino]anthra-9,10-quinone (11.73 g) were dissolved in 250 mL of N,N-dimethylformamide. The reaction mixture thus formed was stirred and heated at 70° C for 24 h. It was cooled then poured into 3 L of acetone and the expected product was precipitated. After filtration, 35.2 g of a black powder containing more than 85% of the expected product was collected. More intensive purification was carried out by liquid-liquid chromatography (n-butanol/water). In this way, 17.5 g of pure product (shiny black powder) was collected. Analyses showed that it corresponded to the expected product (dye 2).

This purification also yielded a smaller proportion of a product corresponding to the product of monosubstitution (see dye 3)

Example 3

Anthraquinone Dye Bound to a Hydrazone Chromophore in 4-pyridinium Series—Variant in which the Linkage is Cationic—Dye 3

The purification carried out during preparation of dye 2 also gave the following product in the form of black powder (0.5 g). Analyses showed that it corresponded to the structure of dye 3:

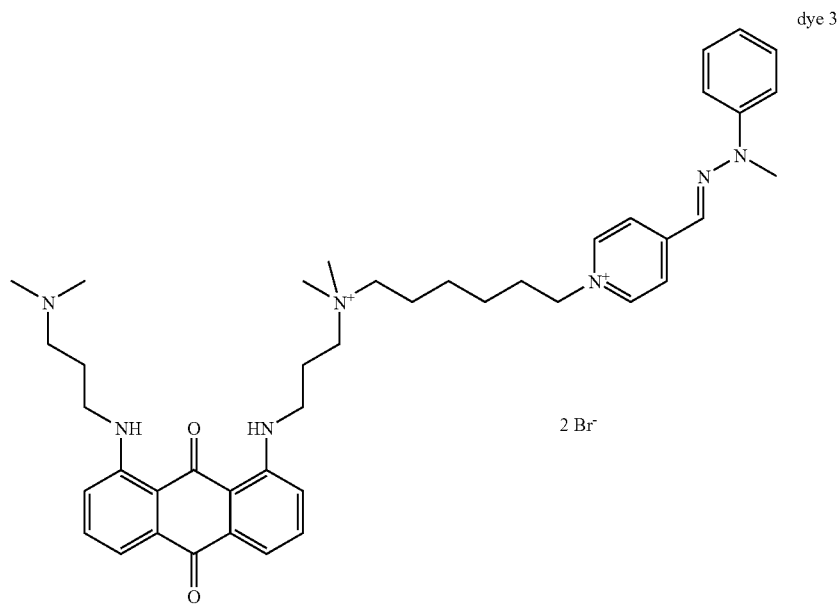
dye 3
2 Br⁻
Example 4
Anthraquinone Dye Bound to a Hydrazone Chromophore—Variant in which the Linkage is Cationic—Dye 4
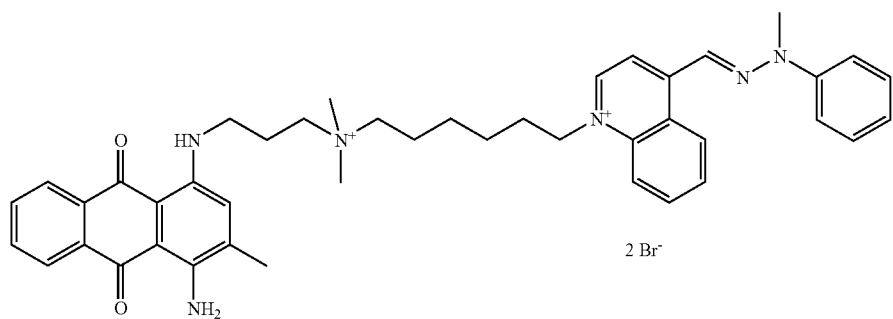
2 Br⁻
Route of Synthesis
First stage: preparation of 1-amino-4-{[3-(dimethylamino)propyl]amino}-2-methylanthra-9,10-quinone
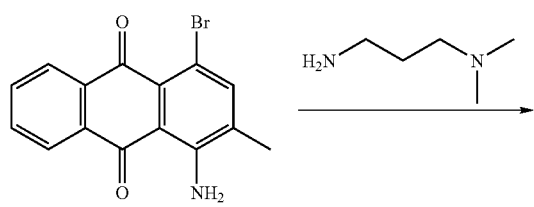
-continued
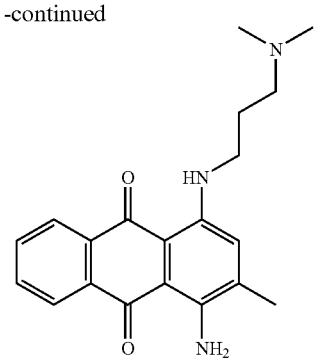

Synthesis Conditions

1-Amino-4-bromo-3-methylanthra-9,10-quinone 6.32 g, 50 ml of NMP (N-methylpyrrolidone) then N,N-dimethylamino-1,3-propylenediamine 25 mL were introduced in succession in a 250-mL flask. The mixture was stirred and heated at 80° C. for 18 h.

After control by TLC (pure AcOEt: RF 0; water/EtOH/AcOH 2:2:1: RF 0.6) showing that reaction was complete, the reaction mixture was poured into 1 L of water.

The precipitate that formed was dissolved in aqueous hydrochloric acid solution (0.25M, 150 mL), which was washed with dichloromethane (150 mL), filtered, then neutralized with soda (10N) to precipitate the expected product. The precipitate thus obtained was filtered and washed with water, taken up in dichloromethane (1.5 L), dried over sodium sulphate, and concentrated under vacuum.

3.24 g of blue-violet powder was obtained; analyses showed that the product complied with (1-amino-4-{[3-(dimethylamino)propyl]amino}-2-methylanthra-9,10-quinone).

Second stage: preparation of quinoline-4-carbaldehyde methyl(phenyl)hydrazone

Third stage: preparation of 1-(6-bromohexyl)-4-{(E)-[methyl(phenyl)hydrazono]methyl}quinolinium bromide

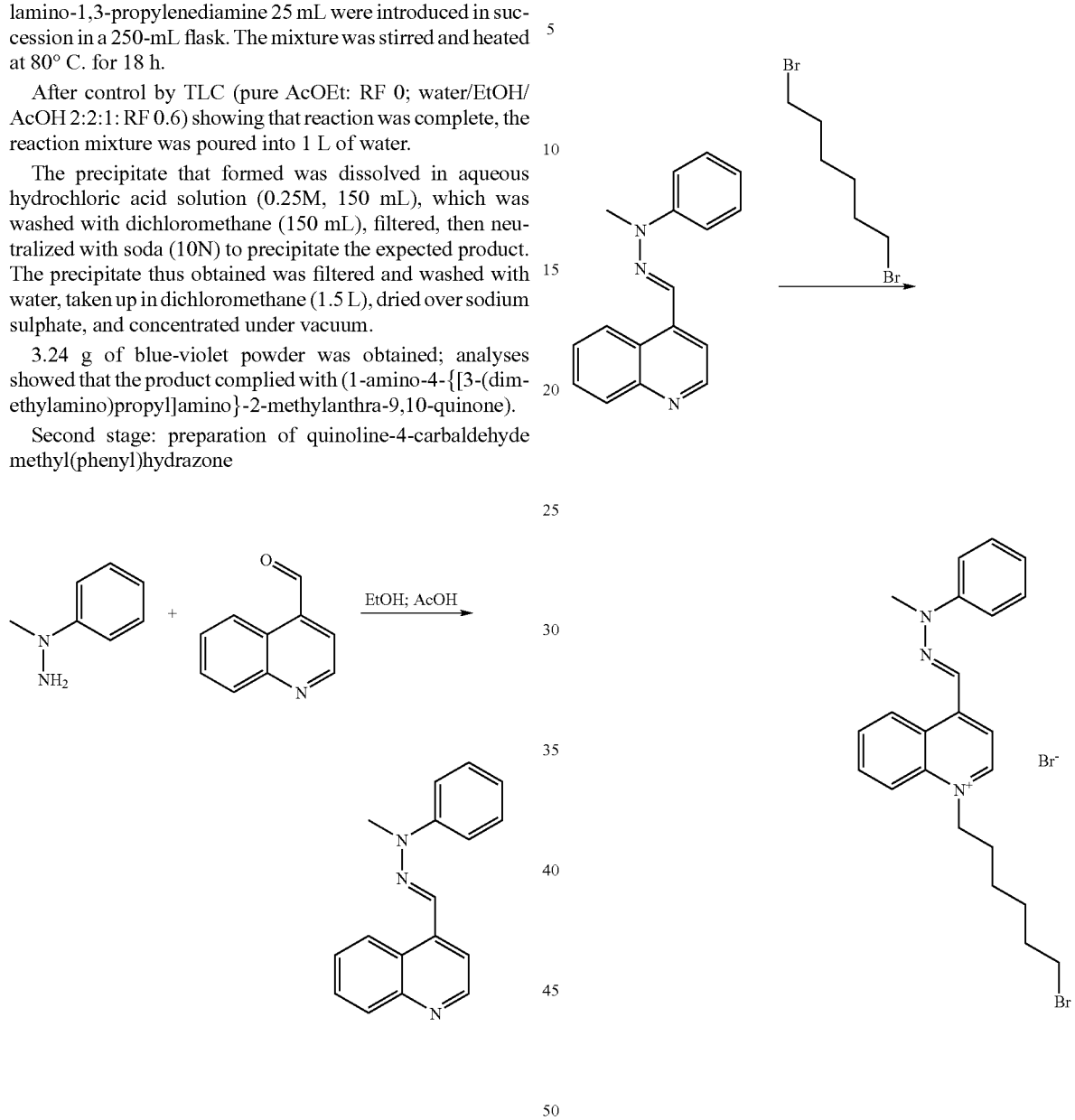

Synthesis Conditions 4.12 g of N-methylphenylhydrazine, 27 mL of ethanol then 0.5 mL of acetic acid were placed in a 250-mL three-necked flask equipped with a thermometer and a condenser. The reaction mixture was stirred and cooled to 10° C. 5.30 g of quinoline 4-carboxaldehyde was then added, in 5 minutes. The mass of the reaction mixture increased, and it was then stirred at 70° C. for 24 h.

After control by TLC (AcOEt/heptane 4:6 RF 0.4) which showed that the reaction had gone to completion, the reaction mixture was poured while hot on 1 L of water/ice mixture. An orange precipitate formed. It was drained, washed with water, then with petroleum ether, and dried under vacuum. 8.03 g of orange powder was obtained. Analyses showed that the product complied with the expected product (quinoline-4-carbaldehyde methyl(phenyl)hydrazone).

Synthesis Conditions

In a 250-mL three-necked flask equipped with a condenser, 90 mL of dibromohexane was stirred and heated at 30° C. then 7.5 g of quinoline-4-carbaldehyde methyl(phenyl)hydrazone was added gradually. The mixture, which became homogeneous after a few minutes, was heated at 80° C. for 5 h.

After control by TLC (CH$_2$Cl$_2$/MeOH 8:2 RF 0.6), which showed that the reaction had gone to completion, the product was drained while hot, washed twice with toluene, drained, and washed with petroleum ether before drying. 9.2 g of product was thus obtained in the form of orange powder, which analyses showed corresponded to the expected product (1-(6-bromohexyl)4-{(E)-[methyl(phenyl)hydrazono]methyl}quinolinium bromide).

Fourth Stage:

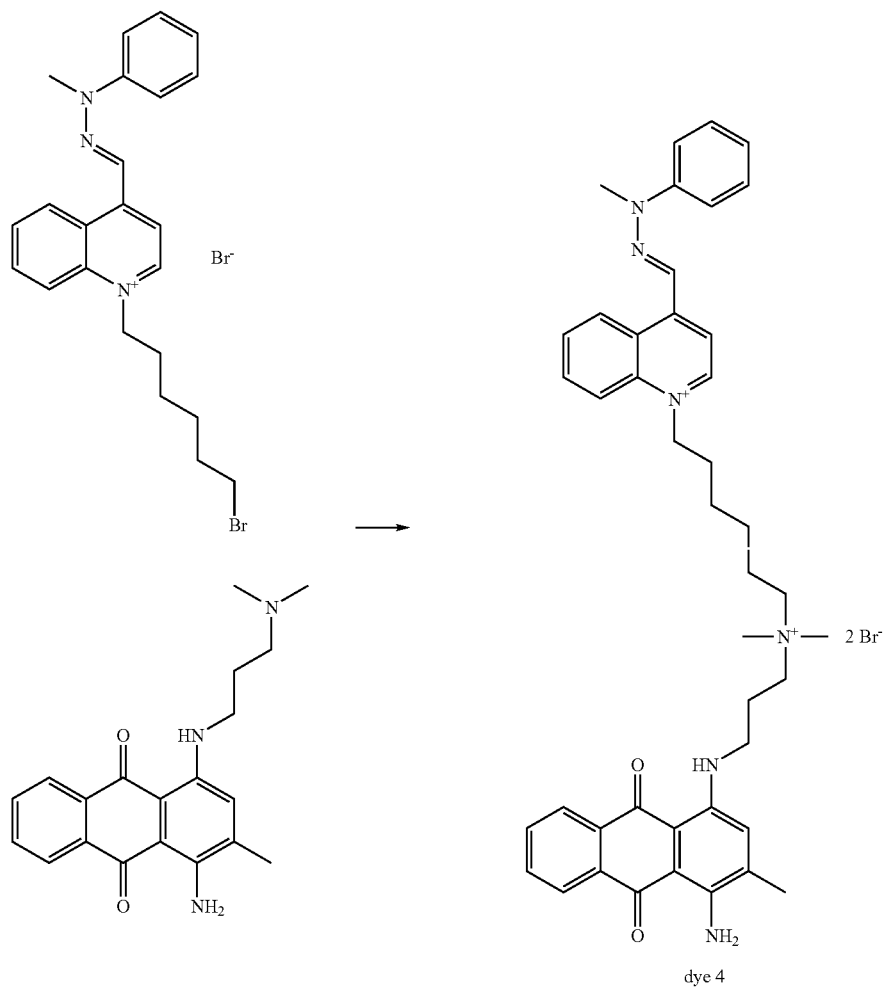

Synthesis Conditions 1-(6-Bromohexyl)-4-{(E)-[methyl(phenyl)hydrazono]methyl}quinolinium bromide (1.5 g) was dissolved in 25 mL of DMF (dimethylformamide), 1-amino-4-{[3-(dimethylamino)propyl]amino}-2-methylanthra-9,10-quinone (1.0 g) was added and the mixture was stirred and heated for 48 h at 80° C., in a flask equipped with a condenser and a calcium chloride trap. After cooling and precipitation of the reaction mixture in acetone, the product was purified by liquid-liquid chromatography (n-butanol/water). 2.2 g of product was collected in the form of black powder. Analyses showed that it corresponded to the expected product (dye 4).

Example 5

Anthraquinone Dye Bound to a Hydrazone Chromophore—Variant in which the Linkage is Cationic—Dye 5

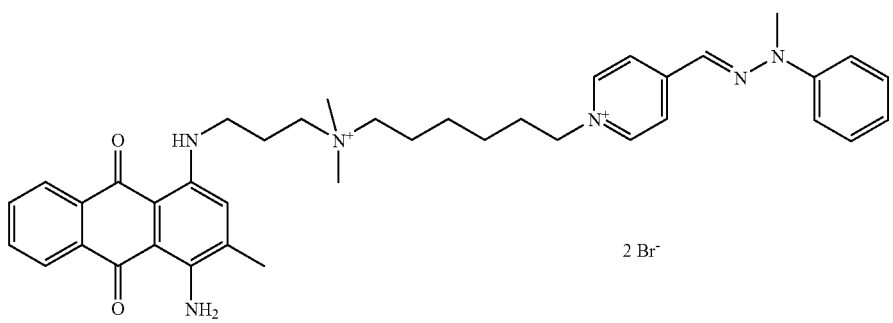

Route of Synthesis

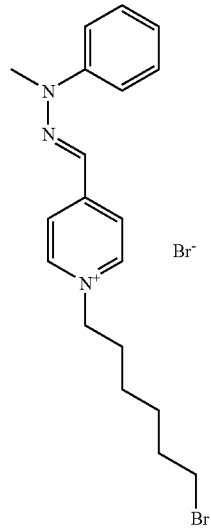

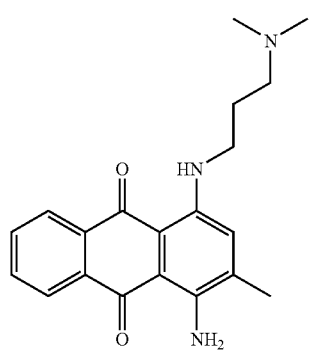

-continued

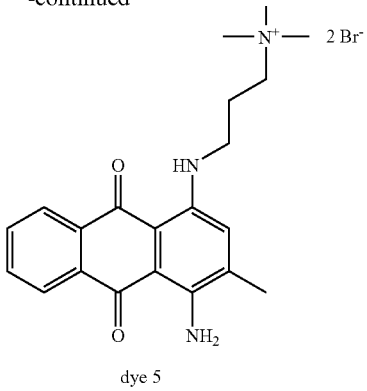

dye 5

Synthesis Conditions 1-(6-bromohexyl)-4-{(E)-[methyl(phenyl)hydrazono]methyl}pyridinium bromide (1.37 g) was dissolved in 25 mL of DMF (dimethylformamide), 1-amino-4-{[3-(dimethylamino)propyl]amino}-2-methylanthra-9,10-quinone (1.00 g) was added and the mixture was stirred and heated for 18 h at 80° C., in a flask equipped with a condenser and a calcium chloride trap. The solvent was removed by vacuum distillation, the paste obtained was mixed with dichloromethane. The solid thus formed was drained and washed several times with dichloromethane. 1.96 g of dark green powder was collected. Analyses showed that it corresponded to the expected product (dye 5).

Example 6

Anthraquinone Dye Bound to an Azo Chromophore—Dye 6

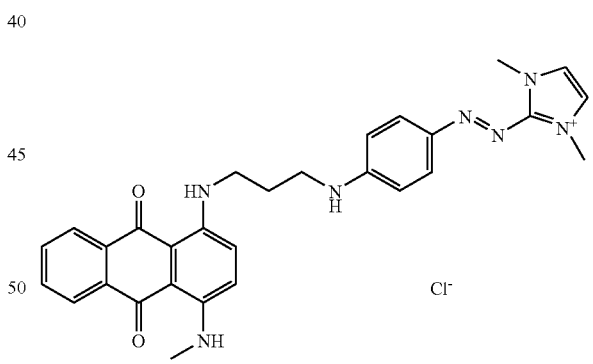

Route of Synthesis:

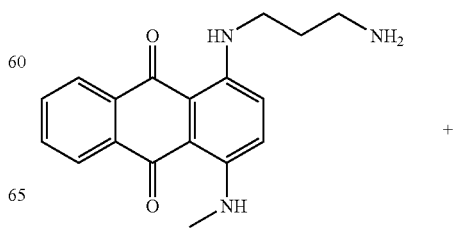

+

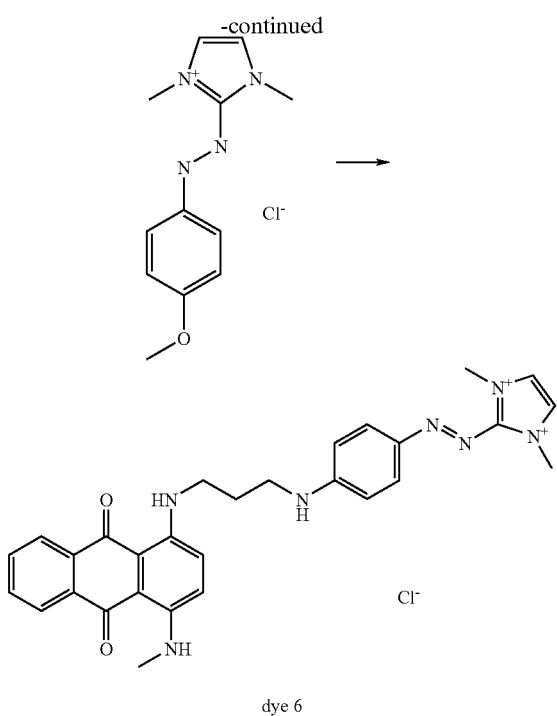

dye 6

Synthesis Conditions

-[(3-Aminopropyl)amino]-4-(methylamino)anthra-9,10-quinone hydrochloride (2.00 g) and 2-[(4-methoxyphenyl)diazenyl]-1,3-dimethyl-1H-imidazol-3-ium chloride (1.78 g) were mixed with 50 mL of methanol and 50 mL of isopropanol. Diisopropylethylamine (1.50 g) was then added and the mixture was stirred and heated under reflux for 24 h. After evaporation of the methanol and addition of isopropanol, a brick-red precipitate was collected (2.2 g after filtration and drying). Analyses showed that the product corresponded to the expected product (dye 6).

Examples of Dyeing

The following dyeing compositions were prepared:

| Dye | $10^{-3}$ mol |
| --- | --- |
| Dyeing support | (*) |
| Demineralized water qsf | 100 g |

(*): dyeing support (1) pH 7 or (2) pH 9.5

Dyeing support (1) pH7:

| 96° ethanol | 20.8 g |
| --- | --- |
| Pentasodium salt of diethylene-triamine-pentaacetic acid, 40% aqueous solution | 0.48 g M.A |
| $C_8$-$C_{10}$ Alkyl polyglucoside, 60% aqueous solution | 3.6 g M.A |
| Benzyl alcohol | 2.0 g |
| Polyethylene glycol with 8 ethylene oxide units | 3.0 g |
| $Na_2HPO_4$ | 0.28 g |
| $KH_2PO_4$ | 0.46 g |

Dyeing support (2) pH9.5:

| 96° ethanol | 20.8 g |
| --- | --- |
| Pentasodium salt of diethylene-triamine-pentaacetic acid, 40% aqueous solution | 0.48 g M.A |
| $C_8$-$C_{10}$ Alkyl polyglucoside, 60% aqueous solution | 3.6 g M.A |
| Benzyl alcohol | 2.0 g |
| Polyethylene glycol with 8 ethylene oxide units | 3.0 g |
| $NH_4Cl$ | 4.32 g |
| Ammonia at 20% of $NH_3$ | 2.94 g |

For dyeing in non-lightening conditions (without oxidizing agent), these compositions were applied to the hair directly.

An oxidizing medium was used for dyeing in lightening conditions. In this case, at the moment of use, each composition was mixed with an equal weight of hydrogen peroxide at 20 volumes (6 wt. %). A final pH of 7 or 9.5 was obtained.

Each mixture obtained was applied to locks of grey hair comprising 90% white hairs, with a bath ratio of 6:1. After waiting 30 minutes, the locks of hair were rinsed, washed with a standard shampoo, rinsed again, and then dried.

The following results of dyeing were obtained:

| | pH 7 (without oxidizing agent) | pH 9.5 (without oxidizing agent) | pH 7 (with oxidizing agent) | pH 9.5 (with oxidizing agent) |
| --- | --- | --- | --- | --- |
| Dye 1 | brownish red | brownish red | brownish red | brownish red |
| Dye 2 | golden brown | golden brown | golden brown | Golden brown |
| Dye 4 | brown | Brown | brown | brown |
| Dye 5 | greenish brown | greenish brown | greenish brown | greenish brown |

The dyed locks of hair were tested for resistance to washing, which involved 12 shampooings (with a standard shampoo) and assessment of color after these 12 shampooings. The locks of hair were still colored after 12 shampooings.

What is claimed is:

1. A mixed cationic direct dye comprising at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage.

2. The dye according to claim 1, wherein the at least one anthraquinone chromophore and the at least one cationic chromophore absorb in the visible range from 400 to 800 nm.

3. The dye according to claim 1, wherein the mixed dye comprises from two to three chromophores.

4. The dye according to claim 1, wherein the at least one cationic chromophore comprises at least one quaternized nitrogen atom.

5. The dye according to claim 1, chosen from compounds of formulas (Ia) and (Ib):

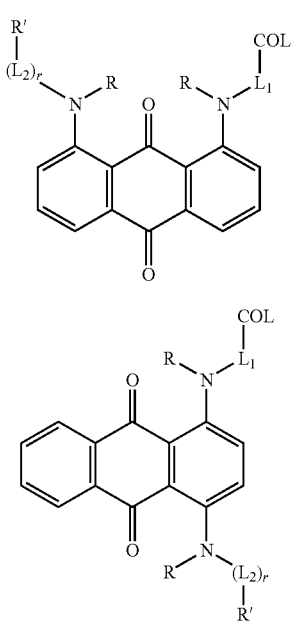

(Ia)

(Ib)

wherein:

$L_1$ is a linkage, which may be cationic or non-cationic, binding the first nitrogen atom of the anthraquinone to the group CCL by means of an atom chosen from carbon, oxygen, and nitrogen, which may be optionally quaternized;

$L_2$ is a linkage, which may be cationic or non-cationic, binding the second nitrogen of the anthraquinone to the group R' by means of an atom chosen from carbon, oxygen, and nitrogen, which may be optionally quaternized;

r is equal to 0 or 1;

the groups R, which may be identical or different, are chosen from hydrogen and optionally substituted $C_1$-$C_4$ alkyl radicals;

at least one of the groups R may be optionally inserted in a saturated or unsaturated ring, which may be optionally aromatic, comprising from 5 to 7 ring members, with $L_1$ or $L_2$;

R' is chosen from:
hydrogen,
linear or branched $C_1$-$C_{12}$ hydrocarbon chains, which may be optionally substituted, optionally interrupted or terminated by at least one group chosen from: amino groups, optionally substituted mono- or di-alkylamino groups, optionally substituted alkyl and arylammonium groups, heterocycles comprising 5 or 6 ring members, which may be saturated or unsaturated, comprising at least one quaternized nitrogen atom inserted in said heterocycle, and
COL groups;

COL is a coloring radical belonging to the cationic azo or cationic hydrazone family, when COL is a cationic azo radical, it is chosen from radicals of formula (IIa):

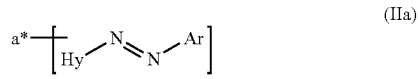

(IIa)

when COL is a cationic hydrazone radical, it is chosen from radicals of formula (IIb):

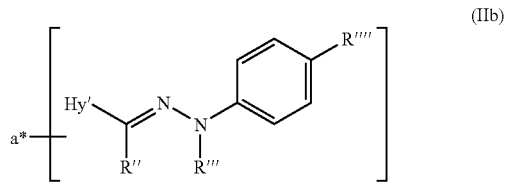

(IIb)

a* is a bond joining COL to $L_1$;

Hy is chosen from cationic heterocycles of formulas (IIIa) and (IIIb):

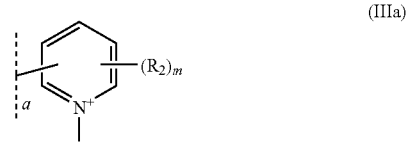

(IIIa)

(IIIb)

Hy' is chosen from cationic heterocycles of formula (IIIa)

$R_1$, which may be identical or different, is chosen from linear or branched $C_1$-$C_{16}$ hydrocarbon chains, which may be saturated or unsaturated, which may form at least one carbon ring comprising from 3 to 7 ring members, optionally condensed with the aromatic ring, optionally substituted, optionally interrupted by at least one group chosen from heteroatoms chosen from oxygen, nitrogen, and sulphur, and carbonyl groups; $R_1$ does not comprise a function chosen from nitro, nitroso, peroxide, and diazo functions; $R_1$ is directly attached to the nitrogen atom, which may be optionally quaternized, of the heteroaromatic ring by means of a carbon atom;

$R_2$, which may be identical or different, are chosen from:
linear or branched $C_1$-$C_{16}$ hydrocarbon chains, which may be saturated or unsaturated, aromatic or non-aromatic, and which may form at least one carbon ring comprising from 3 to 6 ring members, which may be optionally substituted, optionally interrupted by at least one entity chosen from heteroatoms and groups bearing at least one heteroatom, and combinations thereof;
hydroxyl groups,
$C_1$-$C_4$ alkyl-oxy groups and $C_2$-$C_4$ (poly)-hydroxy-alkoxy groups,
alkoxycarbonyl grousp $R_{11}$O—CO—, wherein $R_{11}$ is chosen from $C_1$-$C_4$ alkyl radicals, alkylcarbonyloxy radicals $R_{12}CO$—O—, wherein $R_{12}$ is chosen from $C_1$-$C_4$ alkyl radicals, amino groups and amino groups substituted with one or two $C_1$-$C_4$ alkyl radicals, which may be identical or different, optionally bearing at least one hydroxyl group, wherein the two alkyl radicals may optionally form, together with the nitrogen atom to which they are attached, a heterocycle comprising 5 or 6 ring members optionally bearing another heteroatom identical to or different from nitrogen, alkylcarbonylamino groups $R_{13}CO$—$NR_{14}$—, wherein the radicals $R_{13}$ and $R_{14}$, which may be identical or different, are chosen from $C_1$-$C_4$ alkyl radicals, carbamoyl groups $(R_{15})_2N$—CO, wherein the radicals $R_{15}$, which may be identical or different, are chosen from hydrogen and $C_1$-$C_4$ alkyl radicals, ureido groups $(R_{16})_2N$—CO—$NR_{17}$—, wherein the radicals $R_{16}$ and $R_{17}$, which may be identical or different, are chosen from hydrogen and $C_1$-$C_4$ alkyl radicals, sulphonamide groups $(R_{18})_2N$—$SO_2$—, wherein the radicals $R_{18}$, which may be identical or different, are chosen from hydrogen and $C_1$-$C_4$ alkyl radicals, alkylsulphonylamino groups $R_{19}SO_2$—$NR_{20}$—, wherein the radicals $R_{19}$ and $R_{20}$, which may be identical or different are chosen from hydrogen and $C_1$-$C_4$ alkyl radicals, guanidinium groups $(R_{21})_2N$—$C(=NH_2^+)$—$NR_{22}$—, wherein the radicals $R_{21}$ and $R_{22}$, which may be identical or different, are chosen from hydrogen and $C_1$-$C_4$ alkyl radicals, alkylsulphonyl groups $R_{23}$—$SO_2$—, wherein $R_{23}$ is chosen from $C_1$-$C_4$ alkyl radicals;

nitro groups, cyano groups, halogen atoms, and optionally substituted phenyl groups;

two radicals $R_2$, carried by adjacent carbon atoms, may form, together with the carbon atom to which each is attached, a condensed optionally substituted aromatic ring;

m is an integer ranging from 0 to 4; when m is less than 4, the carbon atom(s) of the unsubstituted heterocycle bear a hydrogen atom;

e is an integer ranging from 0 to 2; when e is less than 2, the carbon atom(s) of the unsubstituted heterocycle carry a hydrogen atom;

Q is chosen from $NR_1$, O, and S;

the bond a of formulas (IIIa) and (IIIb) joins the group Hy to the azo group —N=N—Ar of formula (IIa) or the group Hy' to the hydrazone group —CR"=N—NR'" of formula (IIb);

in formulas (IIIa) and (IIIb), when two radicals $R_2$ carried by two adjacent carbon atoms form an aromatic ring, bond a may join group Hy to the azo group —N=N—Ar of formula (IIa) or group Hy' to the hydrazone group —CR"=N—NR'" of formula (IIb) by means of said aromatic ring;

Ar is an aromatic ring chosen from:

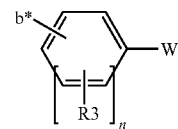

wherein:

b* is a bond joining Ar to NR'" of formula (IIb) or to the azo function of formula (IIa);

n is an integer ranging from 0 to 4; when n is less than 4, the carbon atom(s) of the unsubstituted aromatic ring carry a hydrogen atom;

$R_3$, which may be identical or different, is chosen from:

$C_1$-$C_{16}$ alkyl radicals, which may be optionally substituted, optionally interrupted by at least one entity chosen from heteroatoms and groups comprising at least one heteroatom, and combinations thereof;

hydroxyl groups, $C_1$-$C_4$ alkoxy groups and $C_2$-$C_4$ (poly)-hydroxyalkoxy groups;

alkoxycarbonyl groups $R_{31}O$—CO—, wherein $R_{31}$, is chosen from $C_1$-$C_4$ alkyl radicals;

alkylcarbonyloxy radicals $R_{32}CO$—O—, wherein $R_{32}$ is chosen from $C_1$-$C_4$ alkyl radicals;

alkylcarbonyl radicals $R_{33}$—CO—, wherein $R_{33}$ is chosen from $C_1$-$C_4$ alkyl radicals;

amino groups and amino groups substituted with one or two $C_1$-$C_4$ alkyl radicals, which may be identical or different, optionally bearing at least one hydroxyl group; wherein the two alkyl radicals may optionally form, together with the nitrogen atom to which they are attached, a heterocycle comprising from 1 to 3 heteroatoms chosen from N, O, and S, comprising from 5 to 7 ring members, which may be saturated or unsaturated, aromatic or non-aromatic, and optionally substituted;

alkylcarbonylamino groups $R_{34}CO$—$NR_{35}$—,wherein the radical $R_{34}$ is chosen from $C_1$-$C_4$ alkyl radicals and the radical $R_{35}$ is chosen from hydrogen and $C_1$-$C_4$ alkyl radicals;

aminocarbonyl groups $(R_{36})_2N$—CO—, wherein the radicals $R_{36}$ which may be identical or different, are chosen from hydrogen and $C_1$-$C_4$ alkyl radicals;

ureido groups $N(R_{37})_2$—CO—$NR_{38}$—, wherein the radicals $R_{37}$ and $R_{38}$, which may be identical or different, are chosen from hydrogen and $C_1$-$C_4$ alkyl radicals;

aminosulphonyl groups $(R_{39})_2N$—$SO_2$—, wherein the radicals $R_{39}$, which may be identical or different, are chosen from hydrogen and $C_1$-$C_4$ alkyl radicals;

alkylsulphonylamino groups $R_{40}SO_2$—$NR_{41}$—, wherein the radicals $R_{40}$ and $R_{41}$, which may be identical or different, are chosen from hydrogen and $C_1$-$C_4$ alkyl radicals;

thiol groups HS—;

alkylthio groups $R_{42}S$—, wherein the radical $R_{42}$ is chosen from $C_1$-$C_4$ alkyl radicals;

alkylsulphinyl groups $R_{43}$—SO—, wherein $R_{43}$ is chosen from $C_1$-$C_4$ alkyl radicals;

alkylsulphonyl groups $R_{44}$—$SO_2$—, wherein $R_{44}$ is chosen from $C_1$-$C_4$ alkyl radicals;

nitro groups;

cyano groups; and halogen atoms;

when n is greater than or equal to 2, two adjacent radicals $R_3$ may form, together with the carbon atoms to which they are attached, a secondary ring, aromatic or non-aromatic, comprising 6 ring members, and optionally substituted;

W is chosen from:
  hydrogen,
  halogen atoms chosen from bromine, chlorine, and fluorine,
  —$NR_5R_6$, —$OR_7$, —$NR_4$-Ph-$NR_5R_6$, —$NR_4$-Ph-$OR_7$, —O-Ph-$OR_7$, —O-Ph-$NR_5R_6$, —$SO_2$—$NR_5R_6$, and —$SO_2$—$R_5$ groups; wherein:
    $R_4$ and $R_7$, which may be identical or different, are chosen from hydrogen, $C_1$-$C_{20}$, for example, $C_1$-$C_{16}$ optionally substituted alkyl radicals, $C_1$-$C_{30}$ optionally substituted aralkyl radicals, and optionally substituted aryl radicals;
    $R_5$ and $R_6$, which may be identical or different, are chosen from hydrogen, $C_1$-$C_{20}$, for example, $C_1$-$C_{16}$, optionally substituted alkyl radicals, optionally substituted phenyl radicals, optionally substitued $C_1$-$C_{30}$ aryl and aralkyl radicals, alkylcarbonyl radicals $R_{45}$—CO—, wherein $R_{45}$ is chosen from $C_1$-$C_4$ alkyl radicals optionally substituted;
    $R_5$ and $R_6$ may optionally form, together with the nitrogen atom to which they are attached, a heterocycle comprising from 1 to 3 heteroatoms chosen from N, O, and S, comprising from 5 to 7 ring members, saturated or unsaturated, aromatic or non-aromatic, and optionally substituted;
    $R_5$ and $R_6$, independently of one another may form, together with the carbon atom of the aromatic ring adjacent to that to which —$NR_5R_6$ is attached, a saturated heterocycle comprising 5 or 6 ring members; and
    Ph is an optionally substituted phenyl radical;

R" is chosen from:
  hydrogen,
  $C_1$-$C_{16}$ alkyl radicals, which may be optionally substituted, optionally interrupted by at least one group chosen from heteroatoms and groups comprising at least one heteroatom, and combinations thereof; and
  $C_6$-$C_{30}$ aryl and aralkyl radicals, the aryl portion being optionally substituted with at least one group, which may be identical or different, chosen from chlorine, amino groups, hydroxyl groups, $C_1$-$C_2$ alkoxy groups, amino groups mono- or disubstituted with two alkyl radicals, which may be identical or different, optionally bearing at least one hydroxyl group;

R''' is chosen from
  hydrogen,
  $C_1$-$C_{16}$ alkyl radicals, which may be optionally substituted, optionally interrupted by at least one entity chosen from heteroatoms and groups comprising at least one heteroatom, and combinations thereof;
  $C_6$-$C_{30}$ aryl and aralkyl radicals, the aryl portion optionally being substituted with at least one group, which may be identical or different, chosen from chlorine, amino groups, hydroxyl groups, $C_1$-$C_2$ alkoxy groups, amino groups mono- or disubstituted with two alkyl radicals which may be identical or different, optionally bearing at least one hydroxyl group;

R"" is chosen from hydrogen, halogen atoms chosen from bromine, chlorine, and fluorine, and —$OR_7$ groups;

bond a* is located in a position chosen from:
  on one of the nitrogen atoms, optionally quaternized, of formulas (IIIa) and (IIIb),
  on one of the carbon atoms of the heterocycles of formulas (IIIa) and (IIIb),
  on one of the carbon atoms of the aromatic ring of Ar,
  on the carbon atom bearing R" or R''',
  on the nitrogen atom bearing the radicals $R_5$ and $R_6$, and
  on the oxygen atom bearing $R_7$,
  in which case the radical $R_1$, $R_2$, $R_3$, R", R''', $R_5$, $R_6$, or $R_7$ in question is replaced by a single bond joining $L_1$ to COL;

when R' is the radical COL, $L_2$ is identical to $L_1$ and is joined in the same way to R' as $L_1$ to COL;

the aromatic rings of the anthraquinone chromophores of formula (Ia) and (Ib) may be optionally substituted;

the electroneutrality of the dye is ensured by at least one cosmetically acceptable anion An-, which may be identical or different.

6. The dye according to claim 5, wherein the groups R, which may be identical or different, are chosen from hydrogen and $C_1$-$C_2$ alkyl radicals.

7. The dye according to claim 5, wherein R' is chosen from:
  hydrogen,
  optionally substituted $C_1$-$C_4$ alkyl radicals,
  linear or branched $C_1$-$C_6$ hydrocarbon chains, which may be optionally substituted, and optionally interrupted or terminated by at least one group chosen from amino groups and optionally substituted mono- or di-alkylamino groups, and
  the radical COL.

8. The dye according to claim 5, wherein $R_1$, which may be identical or different, is chosen from linear or branched $C_1$-$C_{10}$ hydrocarbon chains, which may be saturated or unsaturated, and which may form at least one carbon ring comprising 5 or 6 ring members, optionally condensed with the aromatic ring, and optionally substituted.

9. The dye according to claim 5, wherein $R_2$, which may be identical or different, are chosen from:
  linear or branched $C_1$-$C_{10}$ hydrocarbon chains, which may be saturated or unsaturated, and which may form at least one carbon ring comprising 5 or 6 ring members, optionally substituted with at least one group, which may be identical or different, chosen from hydroxyl and $C_1$-$C_2$ alkoxy groups;
  hydroxyl groups,
  $C_1$-$C_4$ alkyl-oxy groups,
  alkoxycarbonyl groups $R_{11}$O—CO—, wherein $R_{11}$ is chosen from $C_1$-$C_2$ alkyl radicals,
  alkylcarbonyloxy radicals $R_{12}$CO—O—, wherein $R_{12}$ is chosen from $C_1$-$C_2$ alkyl radicals;
  amino groups and amino groups substituted with one or two $C_1$-$C_4$ alkyl radicals, which may be identical or different, optionally bearing at least one hydroxyl group, wherein the two alkyl radicals may optionally form, together with the nitrogen atom to which they are attached, a heterocycle comprising 5 or 6 ring members optionally bearing another heteroatom identical to or different from nitrogen,
  alkylcarbonylamino groups $R_{13}$CO—$NR_{14}$—, wherein the radicals $R_{13}$ and $R_{14}$, which may be identical or different, are chosen from $C_1$-$C_2$ alkyl radicals;
  carbamoyl groups $(R_{15})_2$N—CO, wherein the radicals $R_{15}$, which may be identical or different, are chosen from hydrogen and $C_1$-$C_2$ alkyl radicals;

ureido groups $(R_{16})_2N$—CO—$NR_{17}$—, wherein the radicals $R_{16}$ and $R_{17}$, which may be identical or different, are chosen from hydrogen and $C_1$-$C_4$ alkyl radicals;

sulphonamide groups $(R_{18})_2N$—$SO_2$—, wherein the radicals $R_{18}$, which may be identical or different, are chosen from hydrogen and $C_1$-$C_4$ alkyl radicals;

guanidinium groups $(R_{21})_2N$—C(=$NH_2^+$)—$NR_{22}$—, wherein the radicals $R_{21}$ and $R_{22}$, which may be identical or different, are chosen from hydrogen and $C_1$-$C_4$ alkyl radicals;

alkylsulphonyl groups $R_{23}$—$SO_2$—, wherein $R_{23}$ is chosen from $C_1$-$C_4$ alkyl radicals;

cyano groups;

halogen atoms; and optionally substituted phenyl groups.

10. The dye according to claim 9, wherein the radicals $R_2$, which may be identical or different, are chosen from methyl, ethyl, 2-hydroxyethyl, 2-methoxyethyl, methylsulphonyl ($CH_3SO_2$—), methylcarbonylamino ($CH_3CONH$—), hydroxyl, amino, methylamino, dimethylamino, 2-hydroxyethylamino, bis(2-hydroxyethyl)amino, methoxy, ethoxy, and phenyl radicals.

11. The dye according to claim 9, wherein the radicals of formulas (IIIa) and (IIIb) bear two radicals $R_2$, and these radicals $R_2$ form, together with the carbon atoms to which they are attached, a secondary ring, which is aromatic and comprises 6 ring members, optionally substituted with at least one group, which may be identical or different, chosen from hydroxyl groups, $C_1$-$C_4$ alkyl groups, $C_1$-$C_4$ alkoxy groups, amino groups, and amino groups substituted with one or two $C_1$-$C_4$ alkyl radicals, which may be identical or different, and optionally bearing at least one group chosen from hydroxyl and methylcarbonylamino groups.

12. The dye according to claim 11, wherein the two radicals $R_2$ form, together with the carbon atoms to which they are attached, a secondary ring, which is aromatic and comprises 6 ring members, optionally substituted with at least one group chosen from hydroxyl, methoxy, ethoxy, amino, 2-hydroxyethylamino, dimethylamino, and bis-(hydroxyethyl)amino groups.

13. The dye according to claim 5, wherein m is an integer ranging from 0 to 2.

14. The dye according to claim 5 wherein e ranges from 0 to 2.

15. The dye according to claim 14, wherein e is equal to 0.

16. The dye according to claim 5, wherein the radicals $R_3$, which may be identical or different, are chosen from:

optionally substituted $C_1$-$C_{16}$ alkyl radicals, hydroxyl groups, $C_1$-$C_2$ alkoxy groups and $C_2$-$C_4$ (poly)-hydroxyalkoxy groups;

alkoxycarbonyl groups $R_{31}O$—CO—, wherein $R_{31}$ is chosen from $C_1$-$C_4$ alkyl radicals;

alkylcarbonyloxy radicals $R_{32}CO$—O—, wherein $R_{32}$ is chosen from $C_1$-$C_4$ alkyl radicals;

alkylcarbonyl radicals $R_{33}$—CO—, wherein $R_{33}$ is chosen from $C_1$-$C_4$ alkyl radicals;

amino groups and amino groups substituted with one or two $C_1$-$C_4$ alkyl radicals, which may be identical or different, optionally bearing at least one hydroxyl group; wherein the two alkyl radicals may optionally form, together with the nitrogen atom to which they are attached, a heterocycle comprising from 1 to 3 heteroatoms chosen from N, O, and S, comprising from 5 to 7 ring members, saturated or unsaturated, aromatic or non-aromatic, and optionally substituted;

alkylcarbonylamino groups $R_{34}CO$—$NR_{35}$—, wherein the radical $R_{34}$ is chosen from $C_1$-$C_4$ alkyl radicals and the radical $R_{35}$ is chosen from hydrogen and $C_1$-$C_4$ alkyl radicals;

aminocarbonyl groups $(R_{36})_2N$—CO—, wherein the radicals $R_{36}$, which may be identical or different, are chosen from hydrogen and $C_1$-$C_4$ alkyl radicals;

ureido groups $N(R_{37})_2$—CO—$NR_{38}$—, wherein the radicals $R_{37}$ and $R_{38}$, which may be identical or different, are chosen from hydrogen and $C_1$-$C_4$ alkyl radicals;

aminosulphonyl groups $(R_{39})_2N$—$SO_2$—, wherein the radicals $R_{39}$, which may be identical or different, are chosen from hydrogen and $C_1$-$C_4$ alkyl radicals;

alkylsulphonylamino groups $R_{40}SO_2$—$NR_{41}$—, wherein the radicals $R_{40}$ and $R_{41}$, which may be identical or different, are chosen from hydrogen and $C_1$-$C_4$ alkyl radicals;

thiol groups HS—;

alkylthio groups $R_{42}S$—, wherein the radical $R_{42}$ is chosen from $C_1$-$C_4$ alkyl radicals;

alkylsulphonyl groups $R_{44}$—$SO_2$—, wherein $R_{44}$ is chosen from $C_1$-$C_4$ alkyl radicals;

cyano groups; and halogen atoms.

17. The dye according to claim 16, wherein the radicals $R_3$, which may be identical or different, are chosen from:

$C_1$-$C_4$ alkyl radicals optionally substituted with at least one radical, which may be identical or different, chosen from hydroxyl radicals, $C_1$-$C_2$ alkylcarbonylamino radicals, and amino radicals substituted with two $C_1$-$C_2$ alkyl radicals, which may be identical or different, optionally bearing at least one group, which may be identical or different, chosen from hydroxyl and $C_1$-$C_2$ alkoxy radicals; wherein these two alkyl radicals may optionally form, together with the nitrogen atom to which they are attached, a heterocycle comprising 5 or 6 ring members, which may be saturated or unsaturated, and optionally aromatic;

$C_2$-$C_4$ hydroxyalkoxy radicals;

halogen atoms chosen from chlorine and fluorine;

amino radicals and amino radicals substituted with one or two $C_1$-$C_2$ alkyl radicals, which may be identical or different, optionally bearing at least one hydroxyl group;

methylcarbonylamino radicals;

methylsulphonylamino radicals;

hydroxyl radicals;

$C_1$-$C_2$ alkoxy radicals; and methylsulphonyl radicals.

18. The dye according to claim 17, wherein the radicals $R_3$, which may be identical or different, are chosen from:

methyl, ethyl, propyl, and 2-hydroxyethyl radicals, methoxy and ethoxy radicals, 2-hydroxyethyloxy and 3-hydroxypropyloxy radicals, 2-methoxyethyl radicals;

methylsulphonylamino radicals;

amino, methylamino, dimethylamino, and 2-hydroxyethylamino radicals;

methylcarbonylamino radicals;

hydroxyl radicals;

chlorine atoms; and methylsulphonyl radicals.

19. The dye according to claim 5, wherein when the coefficient n is greater than or equal to 2, then two adjacent radicals $R_3$ form, together with the carbon atoms to which they are attached, a secondary aromatic ring comprising 6 ring members, optionally substituted with at least one group, which may be identical or different, chosen from hydroxyl radicals, $C_1$-$C_4$ alkyl radicals, $C_1$-$C_4$ alkoxy radicals, $C_2$-$C_4$ (poly)-hydroxyalkoxy radicals, $C_1$-$C_4$ alkylcarbonylamino radicals, amino radicals, amino radicals substituted with one or two radicals, which may be identical or different, and $C_1$-$C_4$ alkyl radicals optionally bearing at least one hydroxyl group.

20. The dye according to claim 19, wherein two adjacent radicals $R_3$ form, together with the carbon atoms to which they are attached, a secondary aromatic ring comprising 6 ring members, optionally substituted with at least one group chosen from hydroxyl, methoxy, ethoxy, 2-hydroxyethyloxy, amino, methylcarbonylamino, (di)2-hydroxyethylamino, —NH-Ph, —NH-Ph-$NH_2$, —NH-Ph-$NHCOCH_3$, —NH-Ph-OH, and —NH-Ph-$OCH_3$ groups.

21. The dye according to claim 5, wherein n is an integer ranging from 0 to 2.

22. The dye according to claim 5, wherein $R_4$ and $R_7$, which may be identical or different, are chosen from:
hydrogen;
$C_1$-$C_6$ alkyl radicals optionally substituted with at least one group, which may be identical or different chosen from hydroxyl and $C_1$-$C_2$ alkoxy radicals; and
aryl and aralkyl radicals, the aryl portion being optionally substituted with at least one group, which may be identical or different, chosen from chlorine, hydroxyl groups, $C_{1-C2}$ alkoxy groups, amino groups, amino groups mono- or disubstituted with two $C_1$-$C_4$ alkyl radicals, which may be identical or different, optionally bearing at least one hydroxyl group.

23. The dye according to claim 22, wherein the radicals $R_4$ and $R_7$ are chosen from:
hydrogen;
optionally substituted $C_1$-$C_3$ alkyl radicals; and
phenyl radicals, optionally substituted with at least one radical, which may be identical or different, chosen from hydroxyl radicals, $C_1$-$C_2$ alkoxy radicals, amino radicals, and amino radicals substituted with at least one $C_1$-$C_4$ alkyl group optionally bearing at least one hydroxyl group.

24. The dye according to claim 22, wherein the radicals $R_4$ and $R_7$ are chosen from:
hydrogen;
methyl, ethyl, and 2-hydroxyethyl radicals; and
phenyl radicals, optionally substituted with at least one radicals, which may be identical or different, chosen from hydroxyl, methoxy, amino, (di)methylamino, and (di)(2-hydroxyethyl)amino radicals.

25. The dye according to claim 5, wherein $R_5$ and $R_6$, which may be identical or different, are chosen from:
hydrogen;
alkylcarbonyl radicals $R_{45}$—CO—, wherein $R_{45}$ is chosen from optionally substituted $C_1$-$C_4$ alkyl radicals,
$C_1$-$C_6$ alkyl radicals, optionally substituted with at least one group, which may be identical or different, chosen from hydroxyl, $C_1$-$C_2$ alkoxy, amino, and $C_1$-$C_4$ (di-) alkyl amino groups; wherein the alkyl radical may be further substituted with at least one group, which may be identical or different, chosen from $C_1$-$C_4$ alkylsulphonyl, $C_1$-$C_4$ alkylsulphinyl, and $C_1$-$C_4$ alkylcarbonyl groups, and
aryl and aralkyl radicals, the aryl portion being optionally substituted with an entity chosen from chlorine, hydroxyl groups, $C_1$-$C_4$ alkoxy groups, amino groups, amino groups mono- or di-substituted with two radicals, which may be identical or different, chosen from $C_1$-$C_4$ alkyl radicals optionally bearing at least one hydroxyl group.

26. The dye according to claim 25, wherein the radicals $R_5$ and $R_6$, which may be identical or different, are chosen from:
hydrogen;
methylcarbonyl, ethylcarbonyl, and propylcarbonyl radicals;
optionally substituted $C_1$-$C_3$ alkyl radicals, such as methyl, ethyl, 2-hydroxyethyl, and 2-methoxyethyl radicals; and
phenyl radicals, optionally substituted with at least one radical, which may be identical or different, chosen from hydroxyl radicals, $C_1$-$C_2$ alkoxy radicals, amino radicals, and amino radicals substituted with at least one $C_1$-$C_4$ alkyl group optionally bearing at least one hydroxyl group.

27. The dye according to claim 26, wherein the radicals $R_5$ and $R_6$, which may be identical or different, are chosen from:
hydrogen;
methyl, ethyl, and 2-hydroxyethyl radicals;
methylcarbonyl, ethylcarbonyl, and propylcarbonyl radicals; and
phenyl radicals, optionally substituted with at least one radical chosen from hydroxyl, methoxy, amino, dimethylamino, and bis-(2-hydroxyethyl)amino radicals.

28. The dye according to claim 5, wherein the radicals $R_5$ and $R_6$ form, together with the nitrogen atom to which each is attached, a heterocycle comprising from 1 to 2 heteroatoms, chosen from N, O, and S, comprising from 5 to 7 ring members, saturated or unsaturated, aromatic or non-aromatic, and optionally substituted.

29. The dye according to claim 28, wherein the heterocycle comprising from 5 to 7 ring members is chosen from piperidine heterocycles, piperazine heterocycles, homopiperazine heterocycles, pyrrole heterocycles, imidazole heterocycles, and pyrazole heterocycles type optionally substituted with at least one radical, which may be identical or different, chosen from hydroxyl radicals, $C_1$-$C_2$ alkoxy radicals, amino radicals, and amino radicals substituted with at least one $C_1$-$C_4$ alkyl group optionally bearing at least one hydroxyl group.

30. The dye according to claim 29, wherein the radicals $R_5$ and $R_6$ form, together with the nitrogen atom to which each is attached, a heterocycle comprising from 5 to 7 ring members chosen from piperidine, 2-(2-hydroxy ethylpiperidine), 4-(aminomethyl)piperidine, 4-(2-hydroxyethyl) piperidine, 4-(dimethylamino)piperidine, piperazine, 1-methyl piperazine, 1-(2-hydroxyethyl)piperazine, 1-(2-aminoethyl)piperazine, 1-hydroxyethylethoxy piperazine, homopiperazine, 1-methyl-1,4-perhyd rodiazepine, pyrrole, 1,4-dimethylpyrrole, 1-methyl-4-ethylpyrrole, and 1-methyl-4-propyl pyrrole heterocycles.

31. The dye according to claim 5, wherein the radicals $R_5$ and $R_6$ may form, together with the carbon atom of the aromatic ring optionally substituted with a hydroxyl and adjacent to that to which —$NR_5R_6$, is attached, a saturated heterocycle comprising 5 or 6 ring members or saturated condensed heterocycles comprising 5 or 6 ring members.

32. The dye according to claim 31, wherein when W is —$NR_5R_6$, and the bond b* is in the position para to —$NR_5R_6$, then with the aromatic nucleus optionally substituted with a hydroxyl it has the following structure:

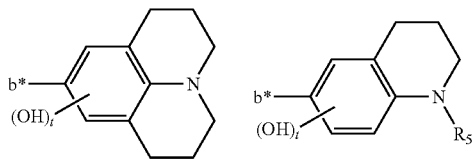

where t is equal to 0 or 1.

33. The dye according to claim 5, wherein R" is chosen from hydrogen and optionally substituted $C_1$-$C_{10}$ alkyl radicals.

34. The dye according to claim 5, wherein R'" is chosen from hydrogen and optionally substitued $C_1$-$C_{10}$ alkyl radicals.

35. The dye according to claim 5, wherein bond a* is located in a position chosen from:
   on one of the nitrogen atoms, quaternized or not, of formulas (IIIa) and (IIIb),
   on the nitrogen atom bearing the radicals $R_5$ and $R_6$, and
   on one of the atoms of the group $R_5$, $R_6$, or $R_7$.

36. The dye according to claim 5, wherein at least one of $L_1$ and $L_2$, is a non-cationic linkage.

37. The dye according to claim 36, wherein $L_1$ and $L_2$, which may be identical or different, are chosen from:
   $C_1$-$C_{20}$ alkylene radicals, which may be optionally substituted, optionally interrupted by a saturated or unsaturated (hetero)cycle, aromatic or non-aromatic, comprising from 3 to 7 ring members, optionally substituted, optionally condensed; said alkylene radical being optionally interrupted by at least one entity chosen from heteroatoms and groups comprising at least one heteroatom, and combinations thereof; wherein the linkage $L_1$ and/or $L_2$ does not comprise a function chosen from an azo, nitro, nitroso, and peroxo functions; and
   $L_2$ may also be a covalent bond, when R' is different from COL.

38. The dye according to claim 37, wherein $L_1$ and $L_2$, which may be identical or different, are chosen from alkylene radicals chosen from methylene, ethylene, linear or branched propylene, linear or branched butylene, linear or branched pentylene, and linear or branched hexylene radicals, optionally substituted and/or interrupted by at least one entity chosen from heteroatoms and groups comprising at least one heteroatom, and combinations thereof; the linkage $L_1$ and/or $L_2$ not comprising a function chosen from azo, nitro, nitroso, and peroxo functions.

39. The dye according to claim 38, wherein $L_1$ and $L_2$, which may be identical or different, are chosen from alkylene radicals substituted with at least one group, which may be identical or different, chosen from hydroxyl, $C_1$-$C_2$ alkoxy, $C_1$-$C_2$ dialkylamino, alkyl($C_1$-$C_4$carbonyl, and alkyl($C_1$-$C_4$sulphonyl radicals.

40. The dye according to claim 37, wherein the cycle or heterocycle, saturated or unsaturated, aromatic or non-aromatic, which may interrupt the alkylene radical of the linkage $L_1$ and/or $L_2$ is chosen from phenylene, naphthylene, phenanthrylene, triazinyl, pyrimidinyl, pyridinyl, pyridazinyl, quinoxalinyl, and cyclohexyl.

41. The dye according to claim 36, wherein $L_1$ and $L_2$, which may be identical or different, are chosen from the following radicals:

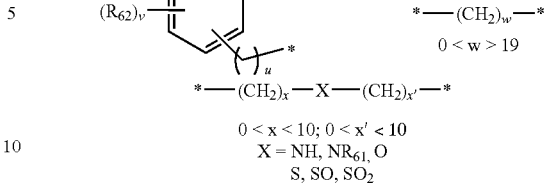

wherein:
   u is equal to 0 or 1;
   v is an integer ranging from 0 to 4;
   $R_{61}$ is chosen from $C_1$-$C_4$ alkyl radicals optionally substituted with at least one radical, which may be identical or different, chosen from hydroxyl, $C_1$-$C_2$ alkoxy, $C_2$-$C_4$ (poly)-hydroxyalkoxy, amino, $C_1$-$C_2$ (di-) alkylamino, and aryl radicals, which may be optionally substituted
   $R_{62}$ has the same definition as $R_3$; and
   * is the end of the linkages $L_1$ and/or $L_2$;

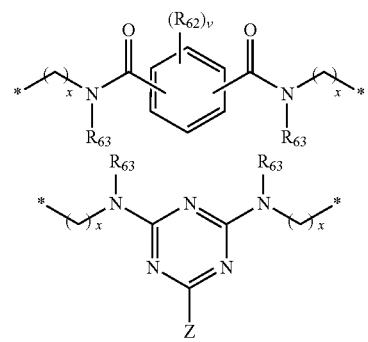

wherein:
   x is an integer ranging from 0 to 6;
   v is an integer ranging from 0 to 4;
   Z is chosen from OH and $NR_{64}R_{65}$;
   $R_{62}$ has the same definition as $R_3$;
   $R_{63}$, which may be identical, are chosen from hydrogen and $C_1$-$C_4$ alkyl radicals;
   $R_{64}$ and $R_{65}$, which may be identical or different, are chosen from hydrogen and $C_1$-$C_8$ alkyl radicals optionally substituted with at least one radical, which may be identical or different, chosen from hydroxyl, $C_1$-$C_2$ alkoxy, $C_2$-$C_4$ (poly)-hydroxyalkoxy, amino, $C_1$-$C_2$ (di-) alkylamino, and aryl radicals, which may be optionally substituted, and
   * is the end of the linkages $L_1$ and/or $L_2$; and

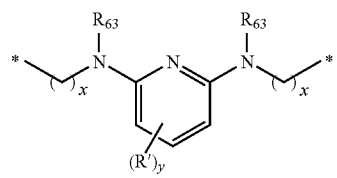

wherein:
   x is an integer ranging from 0 to 6;
   y is an integer ranging from 0 to 3;

R' has the same definition as $R_3$;

$R_{63}$, which may be identical or different, are chosen from hydrogen and $C_1$-$C_4$ alkyl radicals; and

* is the end of the linkages $L_1$ and/or $L_2$.

42. The dye according to claim 5, wherein at least one of the linkages $L_1$ and $L_2$, which may be identical or different, is a linkage bearing at least one cationic charge.

43. The dye according to claim 42, wherein $L_1$ and $L_2$, which may identical or different, are chosen from $C_2$-$C_{40}$ alkylene radicals, bearing at least one cationic charge, optionally substituted and/or optionally interrupted by at least one (hetero)cycle, which may be saturated or unsaturated, aromatic or non-aromatic, identical or different, comprising from 5 to 7 ring members, and/or optionally interrupted by at least one entity chosen from heteroatoms and groups comprising at least one heteroatom, and their combinations; wherein the linkage $L_1$ and/or $L_2$ does not comprise a function chosen from azo, nitro, nitroso, and peroxo functions.

44. The dye according to claim 43, wherein at least one of $L_1$ and $L_2$, which may be identical or different, is cationic and is chosen from $C_2$-$C_{20}$ alkylene radicals:

interrupted by at least one group chosen from groups of the following formulas:

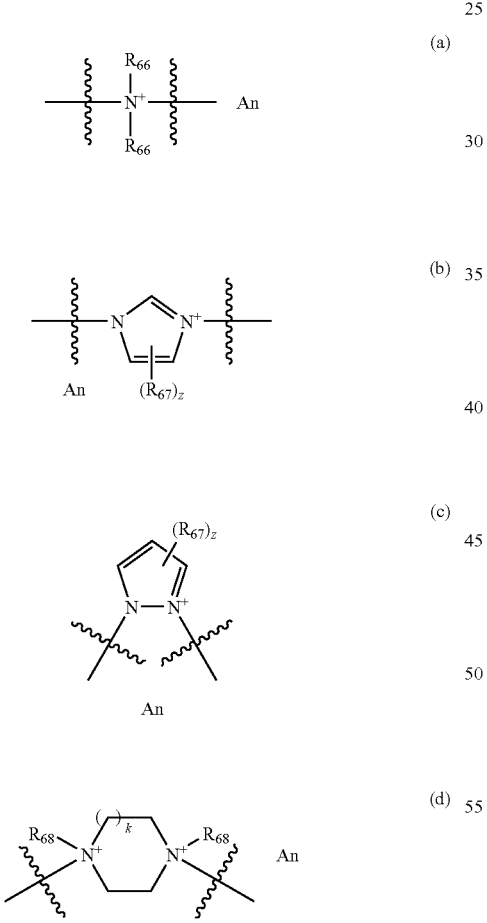

wherein:

$R_{66}$ and $R_{68}$, which may be identical or different, are chosen from $C_1$-$C_8$ alkyl radicals; $C_1$-$C_6$ monohydroxyalkyl radicals; $C_2$-$C_6$ polyhydroxyalkyl radicals; $C_1$-$C_6$ alkoxy($C_1$-$C_6$)alkyl radicals; optionally substituted aryl radicals; optionally substituted aralkyl radicals; $C_1$-$C_6$ aminoalkyl radicals; $C_1$-$C_6$ aminoalkyl radicals, the amine of which is substituted with one or two $C_1$-$C_4$ alkyl radicals which may be identical or different; and alkyl($C_1$-$C_6$)sulphonyl radicals, two radicals $R_{66}$ may form, together with the nitrogen atom to which they are attached, a saturated ring comprising 6 ring members, $R_{67}$, which may be identical or different, is chosen from halogen atoms chosen from bromine, chlorine, and fluorine, $C_1$-$C_6$ alkyl radicals, $C_1$-$C_6$ monohydroxyalkyl radicals, $C_2$-$C_6$ polyhydroxyalkyl radicals, $C_1$-$C_6$ alkoxy radicals, $C_1$-$C_4$ (di-)alkylamino radicals, hydroxycarbonyl radicals, $C_1$-$C_6$ alkylcarbonyl radicals, $C_1$-$C_6$ thioalkyl radicals, alkyl($C_{1-C6}$)thio radicals, alkyl($C_1$-$C_6$)sulphonyl radicals, optionally substitued benzyl radicals, phenyl radicals optionally substituted with at least one radical chosen from methyl, hydroxyl, amino, and methoxy radicals, An is chosen from anions and mixtures of anions, which may be organic or inorganic z is an integer ranging from 1 to 3; if z is less than 3, then the unsubstituted carbon atoms bear a hydrogen atom, k is an integer equal to 1 or 2;

optionally interrupted by at least one entity chosen from heteroatoms and groups comprising at least one heteroatom, and their combinations; with the proviso that the linkage $L_1$ and/or $L_2$ does not comprise a function chosen from nitro, nitroso, and peroxo groups and bonds;

optionally substituted with at least one radical chosen from hydroxyl radicals, $C_1$-$C_2$ alkoxy radicals, $C_2$-$C_4$ (poly)-hydroxyalkoxy radicals, and amino radicals substituted with at least one linear or branched $C_1$-$C_2$ alkyl group optionally bearing at least one hydroxyl group.

45. The dye according to claim 44, wherein the radicals $R_{66}$ and $R_{68}$ of formulas (a) and (d), which may be identical or different, are chosen from $C_1$-$C_6$ alkyl radicals, $C_1$-$C_4$ monohyd roxyalkyl radicals, $C_2$-$C_4$ polyhyd roxyalkyl radicals, $C_2$-$C_4$ alkoxy($C_1$-$C_6$)alkyl radicals, and $C_2$-$C_6$ dimethylaminoalkyl radicals.

46. The dye according to claim 45, wherein the radicals $R_{66}$ and $R_{68}$, which may be identical or different, are chosen from methyl, ethyl, and 2-hydroxyethyl radicals.

47. The dye according to claim 44, wherein the radical $R_{67}$ of formulas (b) and (c) is chosen from halogen atoms chosen from chlorine and fluorine, $C_1$-$C_6$ alkyl radicals, $C_1$-$C_4$ monohydroxyalkyl radicals, $C_1$-$C_4$ alkoxy radicals, hydroxycarbonyl radicals, $C_1$-$C_6$ thioalkyl radicals, and amino radicals disubstituted with a $C_1$-$C_4$ alkyl radical.

48. The dye according to claim 47, wherein the radical $R_{67}$ of formulas (b) and (c) is chosen from chlorine, methyl radicals, ethyl radicals, 2-hydroxyethyl radicals, methoxy radicals, hydroxycarbonyl radicals, and dimethylami no radicals.

49. The dye according to claim 44, wherein z in formulas (b) and (c) is equal to 0.

50. The dye according to claim 5, chosen from:

anthraquinones joined to two azo chromophores in azo-imidazolium series:

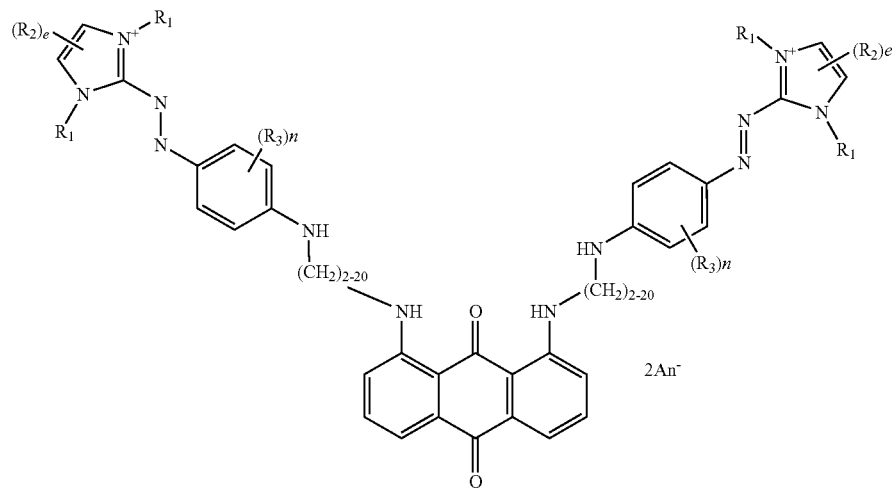
anthraquinones joined to an azo chromophore in azo-imidazolium series:
anthraquinones joined to two azo chromophores in azo-imidazoli series:
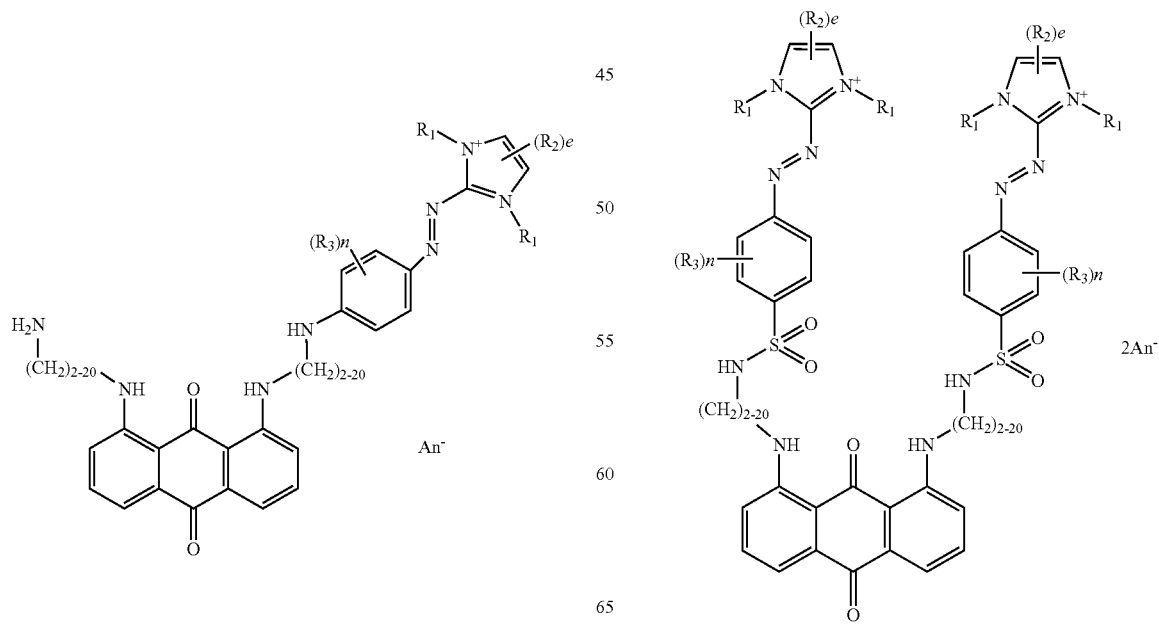

anthraquinones joined to two azo chromophores in 3-azo-pyridinium series:
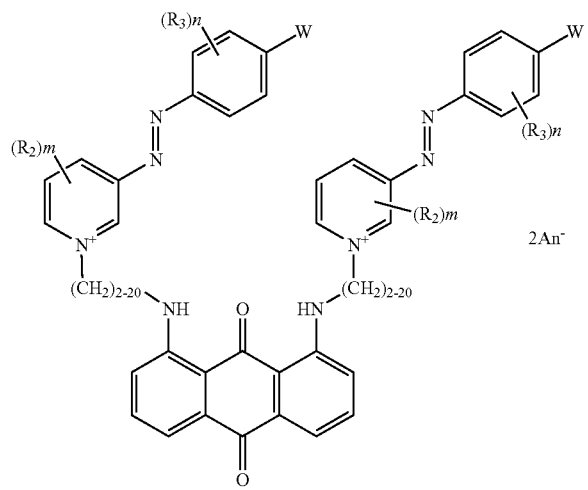
anthraquinones joined to two hydrazone chromophores in 4-pyridinium series:
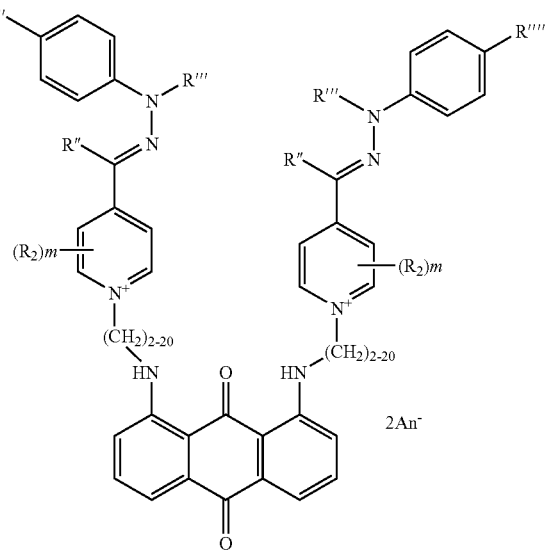
anthraquinones joined to two hydrazone chromophores in 4-pyridinium series in which the linkage is cationic:
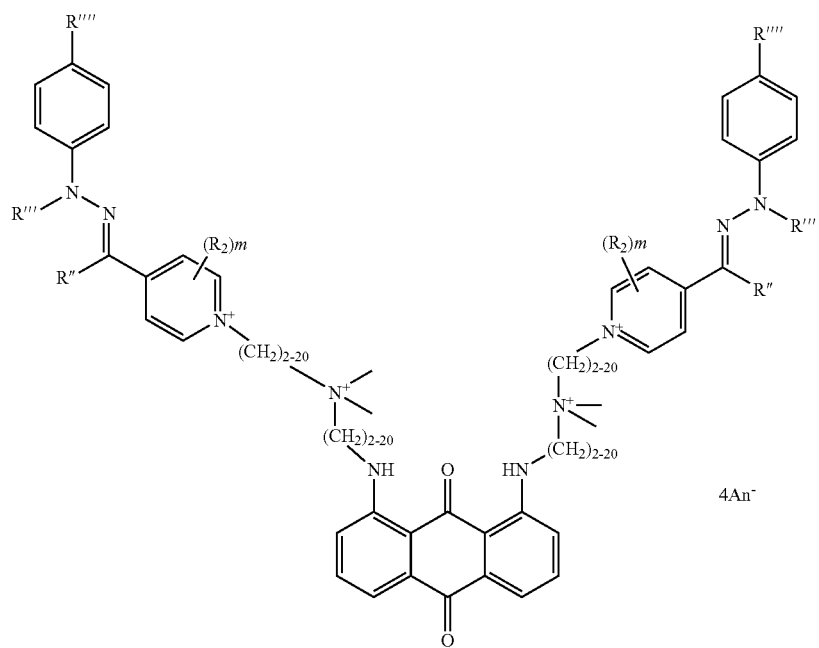

anthraquinones joined to a hydrazone chromophore in 4-pyridinium series in which the linkage is cationic:

anthraquinones joined to an azo chromophore in azo-imidazolium series:

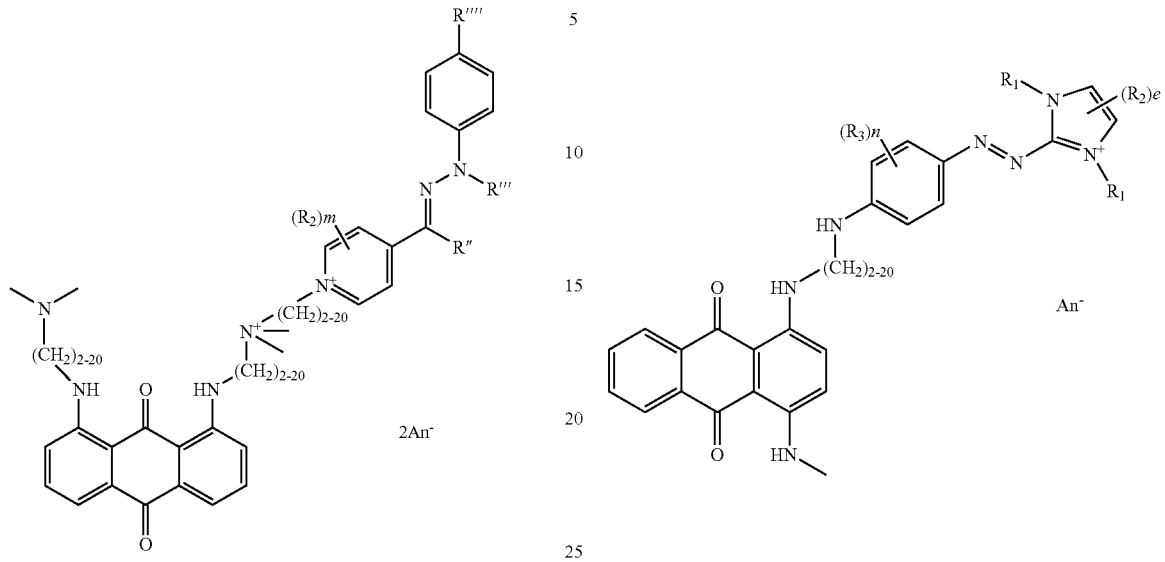

anthraquinones joined to a hydrazone chromophore in 4-quinolinium series in which the linkage is cationic:

and their physiologically acceptable salts and solvates.

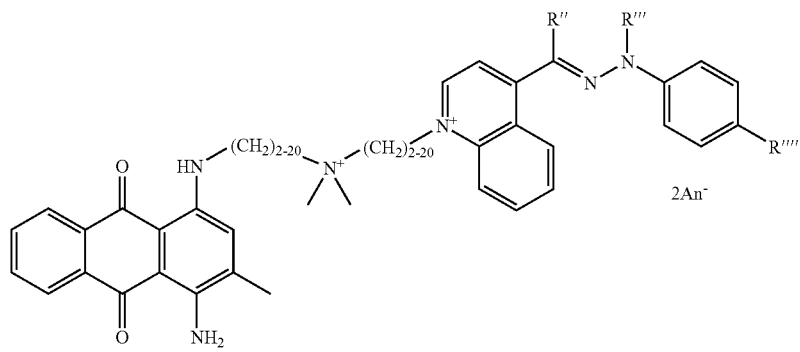

anthraquinones joined to a hydrazone chromophore in 4-pyridinium series in which the linkage is cationic:

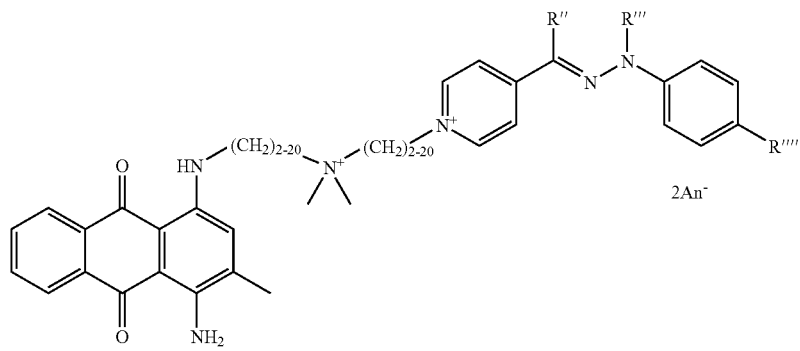

51. The dye according to claim 1, chosen from:
anthraquinones joined to two azo chromophores in azo-imidazolium series:
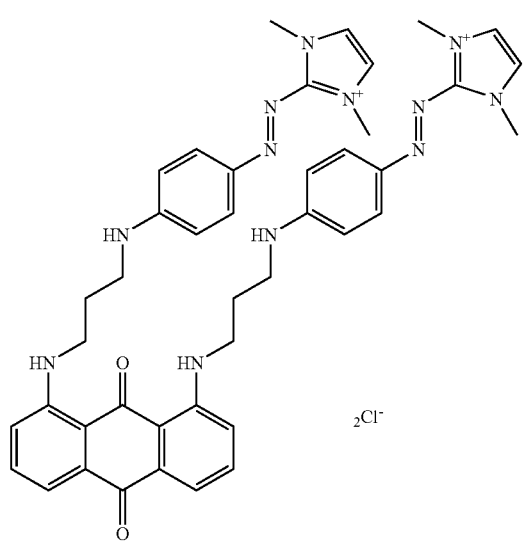
anthraquinones joined to an azo chromophore in azo-imidazolium series:
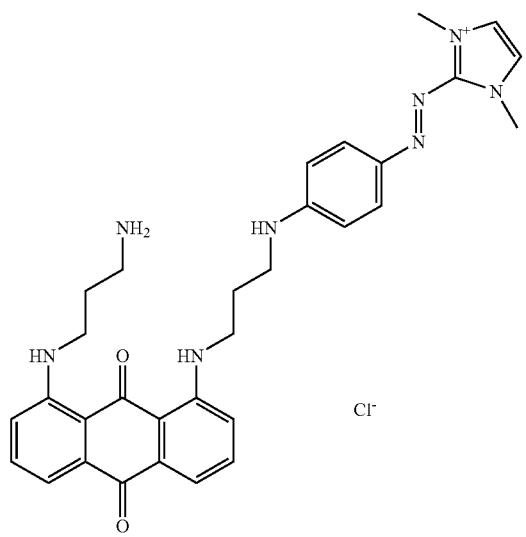
anthraquinones joined to two azo chromophores in azo-imidazolium series:
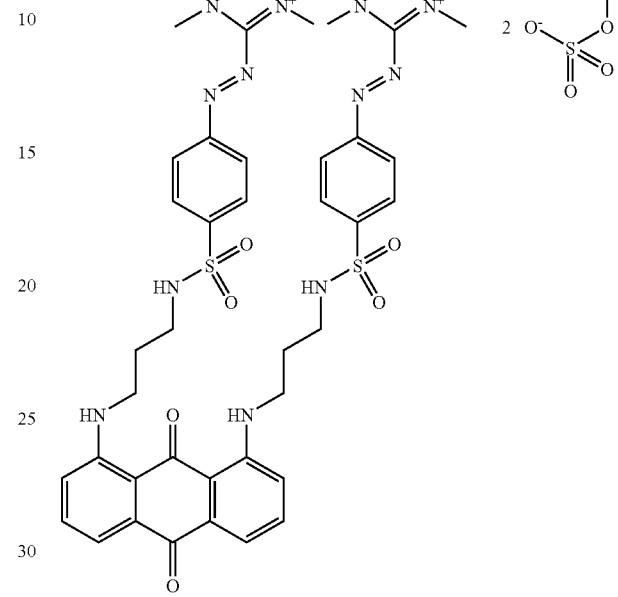
anthraquinones joined to two azo chromophores in 3-azo-pyridinium series:
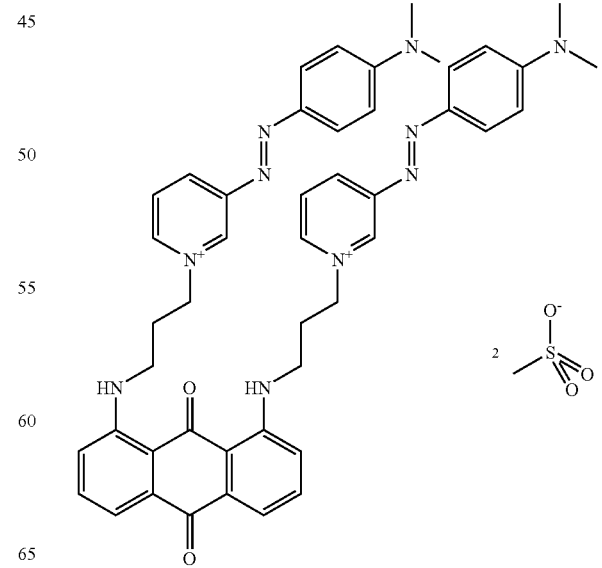

anthraquinones joined to two hydrazone chromophores in 4-pyridinium series:
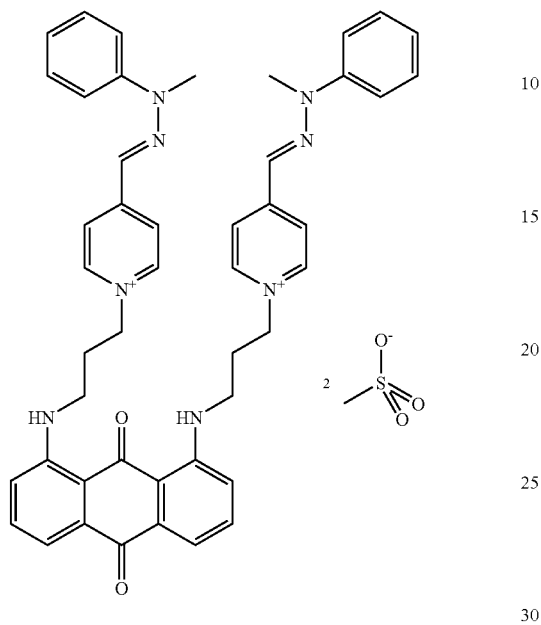
anthraquinones joined to two hydrazone chromophores in 4-pyridinium series in which the linkage is cationic
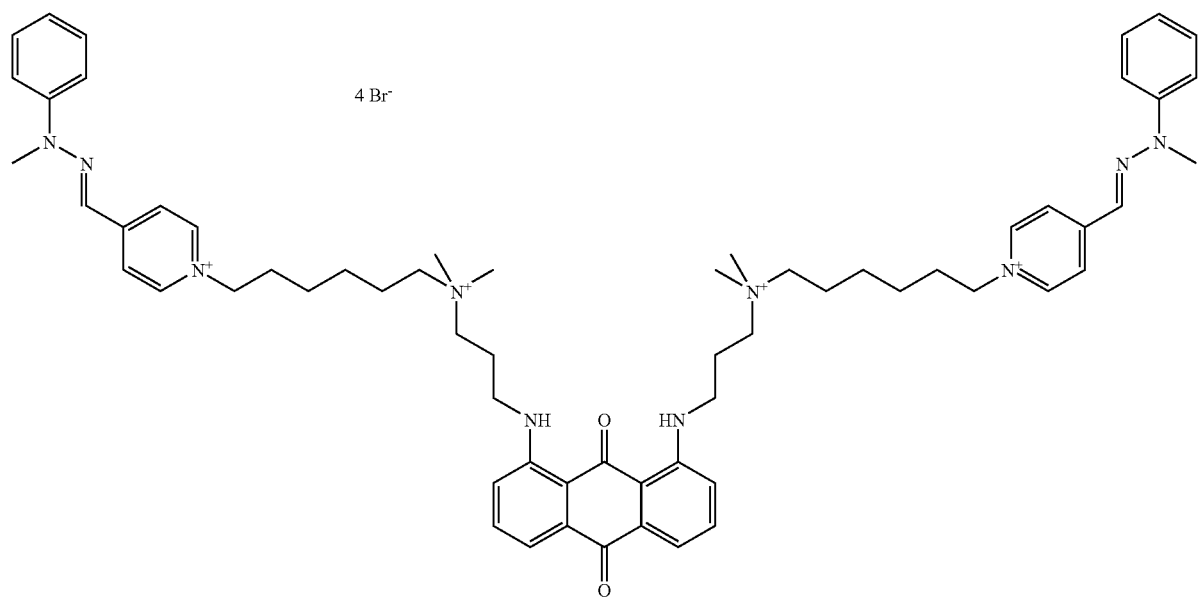

anthraquinones joined to a hydrazone chromophore in 4-pyridinium series in which the linkage is cationic
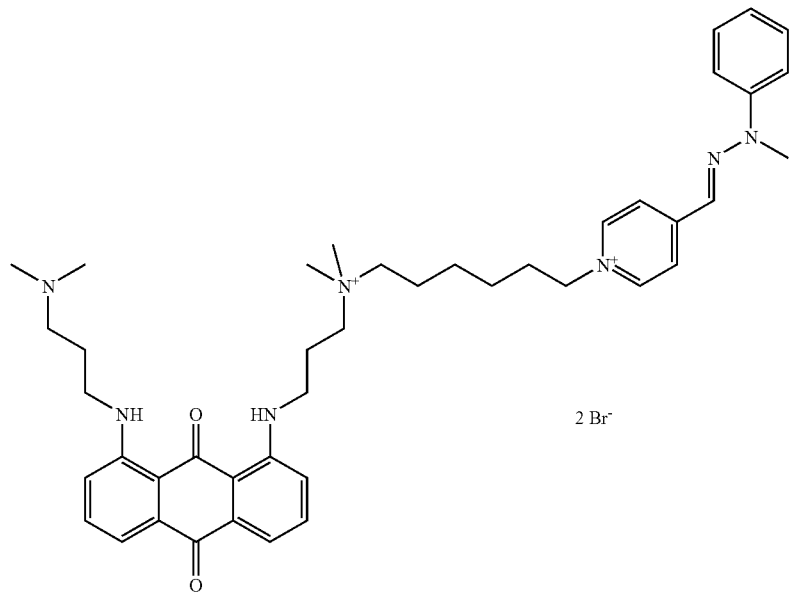
anthraquinones joined to a hydrazone chromophore in 4-quinolinium series in which the linkage is cationic:
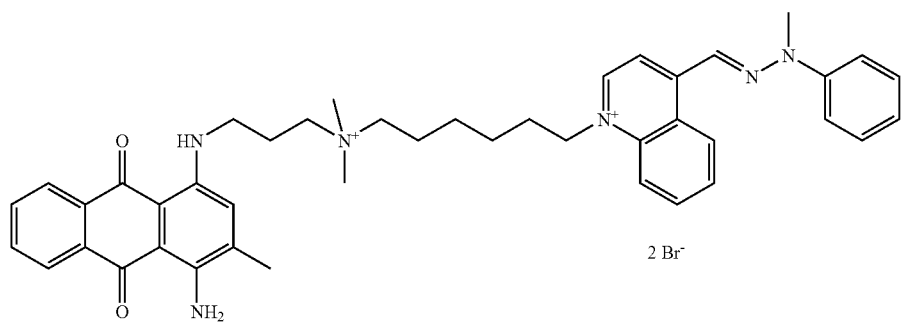
anthraquinones joined to a hydrazone chromophore in 4-pyridinium series in which the linkage is cationic:
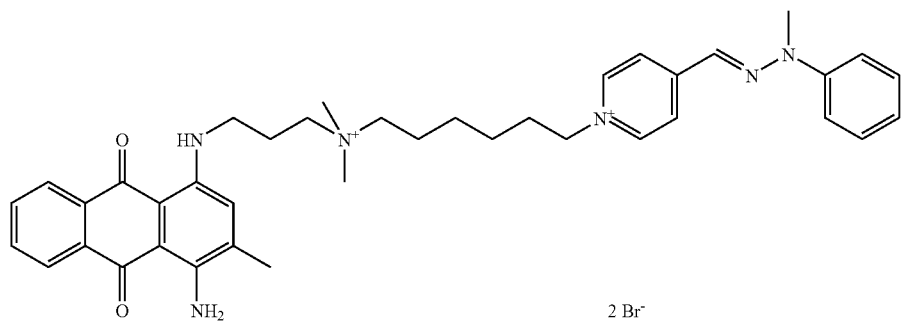

and
  anthraquinones joined to an azo chromophore in azo-imidazolium series:

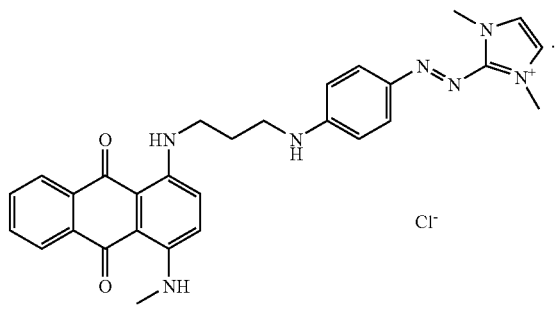

52. A dyeing composition comprising, in a medium suitable for the dyeing of keratin fibers, at least one mixed dye comprising at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage.

53. The composition according to claim 52, wherein the at least one mixed dye is present in the composition in an amount ranging from 0.001 to 20 wt. % relative to the total weight of the composition.

54. The composition according to claim 53, wherein the at least one mixed dye is present in the composition in an amount ranging from 0.005 to 10 wt. % relative to the total weight of the composition.

55. The composition according to claim 54, wherein the at least one mixed dye is present in the composition in an amount ranging from 0.01 to 5 wt. % relative to the total weight of the composition.

56. The composition according to claim 52, further comprising at least one additional direct dye other than the at least one mixed dye.

57. The composition according to claim 56, wherein the at least one additional direct dye is present in the composition in an amount ranging from 0.001 to 10 wt. % relative to the total weight of the dyeing composition.

58. The composition according to claim 52, further comprising at least one oxidation base chosen from paraphenylenediamines, bis-phenylalkylenediamines, para-aminophenols, ortho-aminophenols, heterocyclic bases, and their addition salts.

59. The composition according to claim 52, further comprising at least one coupling agent chosen from metaphenylenediamines, meta-aminophenols, metadiphenols, naphthalenic coupling agents, heterocyclic coupling agents, and their addition salts.

60. The composition according to claim 58, wherein the at least oxidation base is present in the composition in an amount, for each of them, ranging from 0.001 to 10 wt. % relative to the total weight of the composition.

61. The composition according to claim 59, wherein the at least one coupling agent is present in the composition in an amount, for each of them, ranging from 0.001 to 10 wt. % relative to the total weight of the composition.

62. The composition according to claim 52, further comprising at least one oxidizing agent.

63. The composition according to claim 62, wherein the at least one oxidizing agent is chosen from hydrogen peroxide, peroxides of alkali metals and alkaline-earth metals, urea peroxide, bromates and ferricyanides of alkali metals, persalts, enzymes chosen from peroxidases and oxido-reductases comprising two or with four electrons.

64. The composition according to claim 63, wherein the at least one oxidizing agent is hydrogen peroxide.

65. The composition according to claim 52, wherein the pH of the composition ranges from 8 to 11.

66. A method of dyeing of keratin fibers, comprising:
  applying a dyeing composition to the keratin fibers, which may be wet or dry, optionally in the presence of at least one oxidizing agent,
  leaving the dyeing composition on the keratin fibers for a sufficient time to obtain a desired coloration,
  optionally rinsing the fibers,
  washing and rinsing the fibers, and
  drying the fibers or leaving them to dry,
    wherein the dyeing composition comprises, in a medium suitable for the dyeing of keratin fibers, at least one mixed dye comprising at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage.

67. A multi-compartment kit comprising at least one first compartment contains at least one dyeing composition comprising at least one mixed dye, and optionally at least one additional direct dye different from the at least one mixed dye, optionally at least one oxidation base, optionally at least one coupling agent, and at least one second compartment containing at least one oxidizing agent,
  wherein the at least one mixed dye comprises at least one anthraquinone chromophore and at least one cationic chromophore chosen from cationic azo chromophores and cationic hydrazone chromophores, wherein the at least one anthraquinone chromophore is bound to the at least one cationic chromophore by means of at least one linkage.

* * * * *

UNITED STATES PATENT AND TRADEMARK OFFICE
CERTIFICATE OF CORRECTION

PATENT NO.         : 7,582,122 B2
APPLICATION NO.    : 11/510698
DATED              : September 1, 2009
INVENTOR(S)        : Nicolas Daubresse et al.

It is certified that error appears in the above-identified patent and that said Letters Patent is hereby corrected as shown below:

In claim 5, column 69, line 34, "CCL" should read --COL--.

In claim 5, column 70, line 66, "grousp" should read --groups--.

In claim 5, column 72, line 13, "integerranging" should read --integer ranging--.

In claim 9, column 75, line 11, "alkylsuiphonyl" should read --alkylsulphonyl--.

In claim 16, column 76, line 21, "alkylsuiphonyl" should read --alkylsulphonyl--.

In claim 17, column 76, line 48, "methylsuiphonyl" should read --methylsulphonyl--.

In claim 22, column 77, line 26, "$C_{1-C2}$" should read --$C_1$-$C_2$--.

In claim 24, column 77, line 45, "radicals," should read --radical,--.

In claim 30, column 78, line 54, "1-methyl-1,4-perhyd rodiazepine," should read --1-methyl-1,4-perhydrodiazepine,--.

In claim 39, column 79, line 57, "alkyl($C_1$-$C_4$carbonyl," should read --alkyl($C_1$-$C_4$)carbonyl,--.

In claim 39, column 79, lines 57-58, "alkyl($C_1$-$C_4$sulphonyl" should read --alkyl($C_1$-$C_4$)sulphonyl--.

In claim 41, column 80, line 6, "0<w>19" should read --0<w<19--.

In claim 44, column 82, line 11, "$R_{67}$ ," should read --$R_{67}$,--.

In claim 44, column 82, line 18, "alkyl($C_{1-C6}$)thio" should read --alkyl($C_1$-$C_6$)thio--.

UNITED STATES PATENT AND TRADEMARK OFFICE
CERTIFICATE OF CORRECTION

PATENT NO. : 7,582,122 B2
APPLICATION NO. : 11/510698
DATED : September 1, 2009
INVENTOR(S) : Nicolas Daubresse et al.

It is certified that error appears in the above-identified patent and that said Letters Patent is hereby corrected as shown below:

In claim 45, column 82, lines 43-44, "monohyd roxyalkyl" should read --monohydroxyalkyl--.

In claim 45, column 82, line 44, "polyhyd roxyalkyl" should read --polyhydroxyalky--.

In claim 48, column 82, line 61, "dimethylami no" should read --dimethylamino--.

In claim 50, column 84, lines 35-36, "azo-imidazoli" should read --azo-imidazolium--.

In claim 51, column 91, line 35, "cationic" should read --cationic:--.

In claim 51, column 93, line 2, "cationic" should read --cationic:--.

Signed and Sealed this

Twenty-second Day of December, 2009

David J. Kappos
*Director of the United States Patent and Trademark Office*